(12) United States Patent
Ba et al.

(10) Patent No.: US 10,208,167 B2
(45) Date of Patent: Feb. 19, 2019

(54) CYCLODEXTRINS WITH ONE OR MORE POLY(ETHYLENE GLYCOL) UNITS, INCLUSION COMPOUNDS AND DRUG DELIVERY VEHICLES INCLUDING THE SAME, AND METHODS OF MAKING AND USING THE SAME

(71) Applicants: Yong Ba, Monrovia, CA (US); Kim Trang Huu Nguyen, El Monte, CA (US)

(72) Inventors: Yong Ba, Monrovia, CA (US); Kim Trang Huu Nguyen, El Monte, CA (US)

(73) Assignee: The Board of Trustees of the California State University, Long Beach, CA (US)

(*) Notice: Subject to any disclaimer, the term of this patent is extended or adjusted under 35 U.S.C. 154(b) by 0 days.

(21) Appl. No.: 15/286,454

(22) Filed: Oct. 5, 2016

(65) Prior Publication Data

US 2017/0106100 A1    Apr. 20, 2017

Related U.S. Application Data

(60) Provisional application No. 62/241,610, filed on Oct. 14, 2015.

(51) Int. Cl.
| | |
|---|---|
| *C08B 37/16* | (2006.01) |
| *C08G 81/00* | (2006.01) |
| *A61K 47/26* | (2006.01) |
| *C08G 65/331* | (2006.01) |
| *A61K 47/60* | (2017.01) |
| *A61K 47/69* | (2017.01) |

(52) U.S. Cl.
CPC .............. *C08G 81/00* (2013.01); *A61K 47/26* (2013.01); *A61K 47/60* (2017.08); *A61K 47/6951* (2017.08); *C08B 37/0012* (2013.01); *C08B 37/0015* (2013.01); *C08G 65/331* (2013.01); *C08G 2650/38* (2013.01)

(58) Field of Classification Search
None
See application file for complete search history.

(56) References Cited

U.S. PATENT DOCUMENTS

| | | | | |
|---|---|---|---|---|
| 7,141,540 B2* | 11/2006 | Wang | ....................... | B82Y 5/00 514/1 |
| 2007/0015729 A1* | 1/2007 | Geckeler | .................. | B82Y 5/00 514/58 |

OTHER PUBLICATIONS

Gyanwali et al., "Synthetic Methods to Prepare Amphiphilic and Biocompatible Cyclodextrin Derivatives" Published 2011 by the American Chemical Society, 2 pages (Year: 2011).*

Mahony et al., "A click chemistry route to 2-functionalised PEGylated and cationic β-cyclodextrins: co-formulation opportunities for siRNA delivery" Organic anc Biomolecular Chemistry (2012) vol. 10 pp. 4954-4960 (Year: 2012).*

Zhou et al., "Hemodextrin: a self-assembled cyclodextrin-porphyrin construct that binds dioxygen" Biophysical Chemistry (2003) vol. 105 pp. 639-648 (Year: 2003).*

Harris et al., "Poly(ethylene glycols) as Soluble, Recoverable, Phase-Transfer Catalysts" Journal of Organic Chemistry (1982) vol. 47 pp. 4789-4791 (Year: 1982).*

Convertine et al., "pH-Responsive Polymeric Micelle Carriers for siRNA Drugs" Biomacromolecules (2010) vol. 11 pp. 2904-2911 (Year: 2010).*

Shao et al., "Jellyfish-Shaped Amphiphilic Dendrimers: Synthesis and Formation of Extremely Uniform Aggregates" Macromolecules vol. 47 pp. 916-921 (Year: 2014).*

Jedlinski et al., "Polymerization of lactones, 17a) Synthesis of ethylene glycol-L-lactide block copolymers" Macromolecular Chemistry vol. 194 pp. 1681-1689 (Year: 1993).*

Du et al., "CPT loaded nanoparticles based on beta-cyclodextrin-grafted poly(ethylene glycol)/poly (L-glutamic acid) diblock copolymer and their inclusion complexes with CPT" Colloids and Surfaces B: Biointerfaces vol. 113, pp. 230-236 (Year: 2014).*

Nikolaos A. Peppas et al.; "Poly(ethylene glycol)-Containing Hydrogels in Drug Delivery"; Journal of Controlled Release; 1999; vol. 62; pp. 81-87; Elsevier Science B.V.

Massimo Fresta et al.; "Ocular Tolerability and In Vivo Bioavailability of Poly(ethylene glycol) (PEG)-Coated Polyethyl-2-Cyanoacrylate Nanosphere-Encapsulated Acyclovir"; Journal of Pharmaceutical Science; Mar. 2001; vol. 90, No. 3; pp. 288-297; Wiley-Liss, Inc., the American Pharmaceutical Association.

Petr Bures et al.; "Surface Modifications and Molecular Imprinting of Polymers in Medical and Pharmaceutical Applications"; Journal of Controlled Release; 2001; vol. 72; pp. 25-33; Elsevier Science B.V.

Mark E. Davis et al.; "Cyclodextrin-Based Pharmaceutics: Past, Present and Future"; Nature Reviews; Dec. 2004; vol. 3; pp. 1023-1035; Nature Publishing Group.

F. Hirayama et al.; "Cyclodextrin-Based Controlled Drug Release System"; Advanced Drug Delivery Reviews; 1999; vol. 36; pp. 125-141; Elsevier Science B.V.

(Continued)

*Primary Examiner* — Eric Olson
(74) *Attorney, Agent, or Firm* — Andrew D. Fortney; Central California IP Group, P.C.

(57) ABSTRACT

A compound comprising a cyclodextrin and a monoalkoxy polyethylene glycol linked thereto through an ether bond (a "pegylated cyclodextrin") is disclosed, as are drug delivery vehicles and pharmaceutical formulations including the same, and methods for making the compound and the drug delivery vehicle and for delivering the drug to a patient in need thereof. The method of making includes the steps of creating either a tosylated monoalkoxy polyethylene glycol or a tosylated cyclodextrin, and either reacting the tosylated monoalkoxy polyethylene glycol with a deprotonated cyclodextrin, or reacting the tosylated cyclodextrin with a deprotonated monoalkoxy polyethylene glycol. The present pegylated cyclodextrin readily forms an inclusion compound with certain drugs to protect the drug against adverse interactions with mucin (e.g., in a mucus membrane).

18 Claims, 48 Drawing Sheets

(56) References Cited

OTHER PUBLICATIONS

Hitoshi Hashimoto; "Present Status of Industrial Application of Cyclodextrins in Japan"; Journal of Inclusion Phenomena and Macrocyclic Chemistry; 2002; vol. 44; pp. 57-62; Kluwer Academic Publishers; Netherlands.

William C. Cromwell et al.; "Cyclodextrin-Adamantanecarboxylate Inclusion Complexes: Studies of the Variation in Cavity Size"; J. Phys. Chem.; 1985; vol. 89; pp. 326-332; American Chemical Society.

Jianjun Cheng et al.; "Synthesis of Linear, B-Cyclodextrin-Based Polymers and Their Camptothecin Conjugates"; Bioconjugate Chem.; 2003; vol. 14; pp. 1007-1017; American Chemical Society.

Jennifer J. Sahlin et al.; "Enhanced Hydrogel Adhesion by Polymer Interdiffusion: Use of Linear Poly(ethylene glycol) as an Adhesion Promoter"; J. Biomater. Sci. Polymer Edn.; 1997; vol. 8, No. 6; pp. 421-436; VSP.

D. Marshall et al.; "Polyethylene Glycol Modification of a Galactosylated Streptavidin Clearing Agent: Effects on Immunogenicity and Clearance of a Biotinylated Anti-Tumour Antibody"; British Journal of Cancer; 1996; vol. 73; pp. 565-572; Stockton Press.

Yanbin Huang et al.; "Molecular Aspects of Muco- and Bioadhesion: Tethered Structures and Site-Specific Surfaces"; Journal of Controlled Release; 2000; vol. 65; pp. 63-71; Elsevier Science B.V.

Thorsteinn Loftsson et al.; "Cyclodextrins in Drug Delivery"; Expert Opinion on Drug Delivery; 2005; vol. 2(2); pp. 335-351; Ashley Publications Ltd.

Krassimira Yoncheva et al.; "Bioadhesive Properties of Pegylated Nanoparticles"; Expert Opinion on Drug Delivery; 2005; vol. 2(2); pp. 205-218; Ashley Publications Ltd.

Samuel K. Lai et al.; "Rapid Transport of Large Polymeric Nanoparticles in Fresh Undiluted Human Mucus"; PNAS; 2007; vol. 104, No. 5; pp. 1482-1487; The National Academy of Sciences of the USA.

Cecile Huin et al.; "Anionic Ring-Opening Polymerization of Ethylene Oxide in DMF with Cyclodextrin Derivatives as New Initiators"; Carbohydrate Polymers; 2013; vol. 94; pp. 323-331; Elsevier Ltd.

Rajesh Agrawal et al.; "Cyclodextrins—A Review on Pharmaceutical Application for Drug Delivery"; International Journal of Pharmaceutical Frontier Research; 2012; vol. 2(1); pp. 95-112.

J. Milton Harris et al.; "Effect of Pegylation on Pharmaceuticals"; Nature Reviews; 2003; vol. 2; pp. 214-221; Nature Publishing Group.

Frank Van De Manakker et al.; "Cyclodextrin-Based Polymeric Materials: Synthesis, Properties, and Pharmaceutical/Biomedical Applications"; Biomacromolecules; 2009; vol. 10, No. 12; pp. 3157-3175; American Chemical Society.

Marcus E. Brewster et al.; "Cyclodextrins as Pharmaceutical Solubilizers"; Advanced Drug Delivery Reviews; 2007; vol. 59; pp. 645-666; Elsevier B.V.

Rajeswari Challa et al.; "Cyclodextrins in Drug Delivery: An Updated Review"; AAPS PharmSciTech; 2005; vol. 6 (2), Article 43; pp. E329-E357.

Katageri Akshay R et al.; "Cyclodextrin A Gift To Pharmaceutical World Review"; International Research Journal of Pharmacy; 2012; vol. 3 (1); pp. 52-56.

Redouan Mahou et al.; "Versatile Route to Synthesize Heterobifunctional Poly(ethylene glycol) of Variable Functionality for Subsequent Pegylation"; Polymers; 2012; vol. 4; pp. 561-589.

Samuel Zalipsky; "Functionalized Poly(ethylene glycol) for Preparation of Biologically Relevant Conjugates"; Bioconjugate Chem.; 1995; vol. 6; pp. 150-165; American Chemical Society.

Hassan Namazi et al.; "Synthesis and Controlled Release of Biocompatible Prodrugs of B-Cyclodextrin Linked with PEG Containing Ibuprofen or Indomethacin"; Iranian Polymer Journal; 2005; vol. 14, No. 10; pp. 921-927.

Jozsef Szejtli; "Past, Present, and Future of Cyclodextrin Research"; Pure Appl. Chem.; 2004; vol. 76, No. 10; pp. 1825-1845; IUPAC.

Thorsteinn Loftsson et al.; "Cyclodextrins and Their Pharmaceutical Applications"; International Journal of Pharmaceutics; 2007; vol. 329; pp. 1-11; Elsevier B.V.

Thorsteinn Loftsson et al.; "Pharmaceutical Applications of Cyclodextrins. 1. Drug Solubilization and Stabilization"; Journal of Pharmaceutical Sciences; 1996; vol. 85, No. 10; pp. 1017-1025; American Pharmaceutical Association, the American Chemical Society.

Thorsteinn Loftsson et al.; "Effects of Cyclodextrins on Drug Delivery Through Biological Membranes"; Journal of Pharmaceutical Sciences; 2007; vol. 96, No. 10; pp. 2532-2546; Wiley InterScience.

* cited by examiner

N=6, 7, and 8 for α-CD, β-CD and γ-CD, respectively.

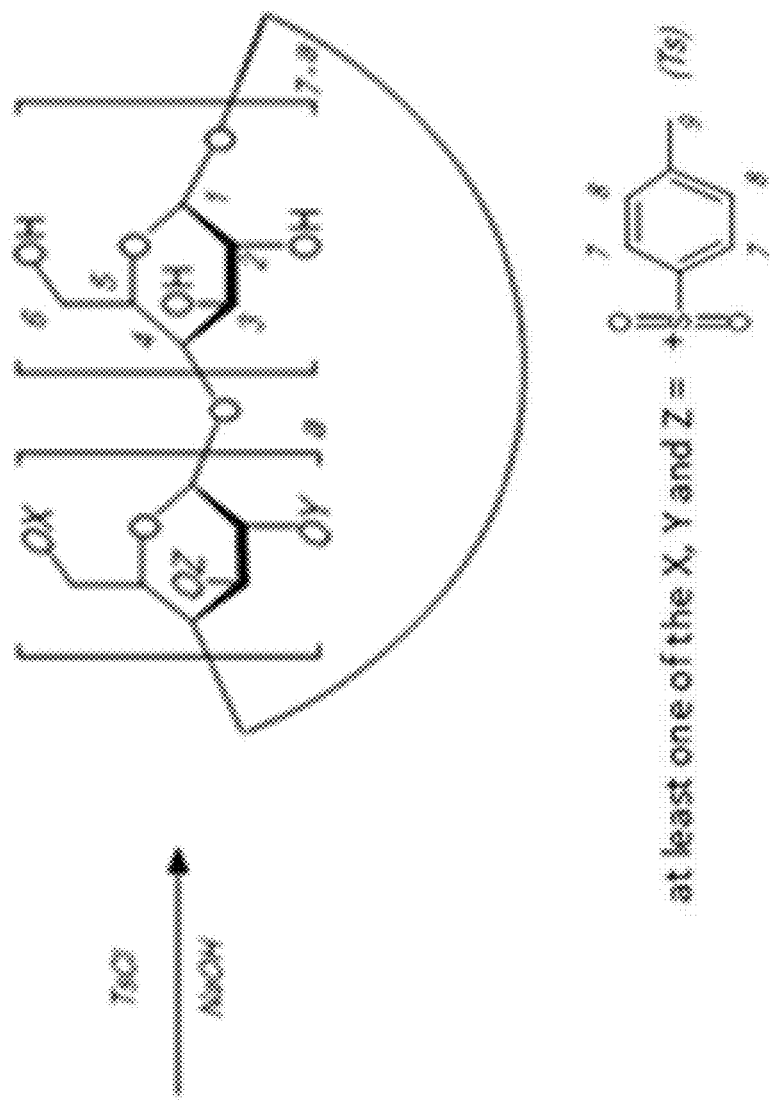
FIG. 21
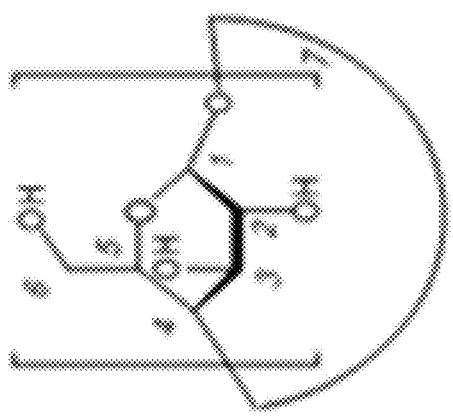

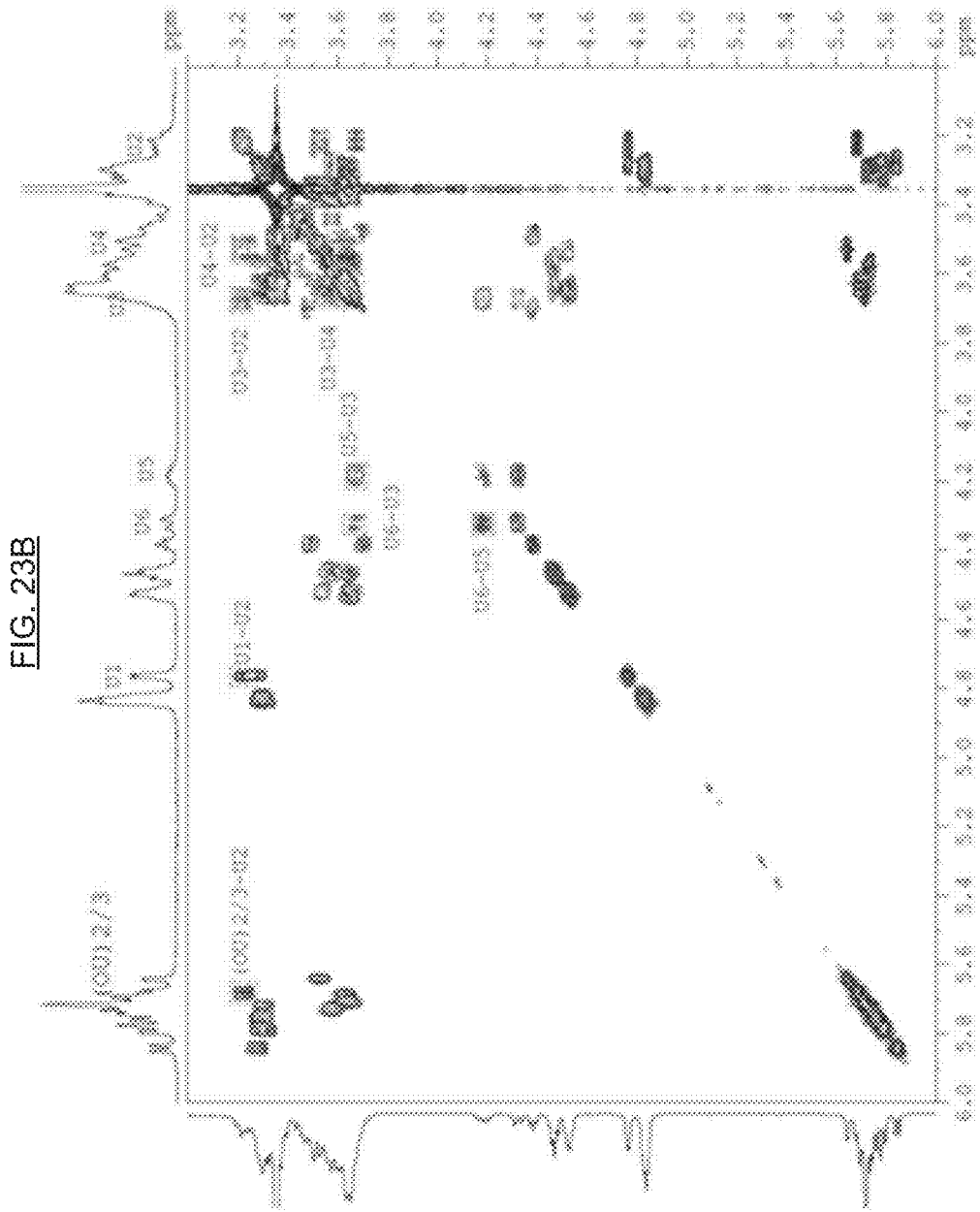

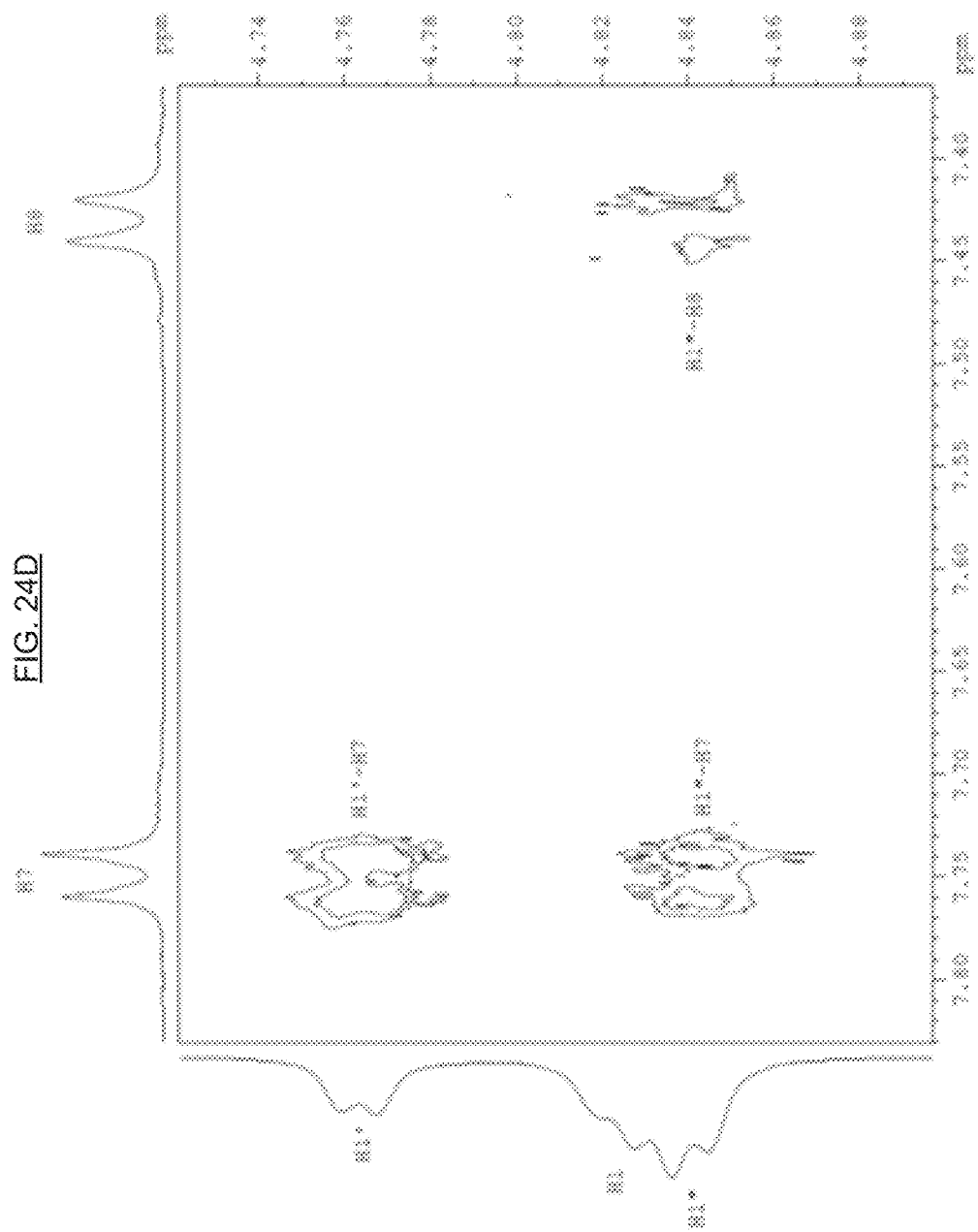

CYCLODEXTRINS WITH ONE OR MORE POLY(ETHYLENE GLYCOL) UNITS, INCLUSION COMPOUNDS AND DRUG DELIVERY VEHICLES INCLUDING THE SAME, AND METHODS OF MAKING AND USING THE SAME

RELATED APPLICATION(S)

This application claims priority to U.S. Provisional Pat. Appl. No. 62/241,610, filed Oct. 14, 2015, incorporated herein by reference.

FIELD OF THE INVENTION

The present invention generally relates to the field of cyclodextrins. More specifically, embodiments of the present invention pertain to cyclodextrins containing one or more polyethylene glycol (PEG) units and methods of making and using the same.

DISCUSSION OF THE BACKGROUND

Cyclodextrins (CDs) are cyclic molecules formed by (1,4)-linked α-D(+)-glucopyranoside units (FIG. 1C). The most common types are α-, β-, and γ-CDs, comprising 6, 7 and 8 α-D(+)-glucopyranoside units, respectively (FIG. 1A). As shown in FIG. 1B, CD molecules have the shapes like truncated cones with the primary hydroxyl groups at the narrow edges and secondary hydroxyl groups at the wider edges. The inner cavities of CDs are more hydrophobic and outer peripheries are more hydrophilic. In an aqueous environment, apolar molecules or apolar sections of molecules can be extracted from water into the CDs' cavities to form inclusion complexes (ICs) if the sizes of the molecules fit the cavities of the CDs. The driving force for the formation of the ICs is primarily due to hydrophobic effect. Owing to this property, CDs have been used in many industrial applications including pharmaceuticals and industrial fields including foods, cosmetics and textiles as solubilizing agents, stabilizers, emulsifiers, etc.

Unlike acyclic saccharides, the solubilities of CDs in water are not great because intramolecular hydrogen bonds can form between the (OH)2 groups and the (OH)3 groups along the peripheral edges, which limits their hydrogen bonding interactions with water. In the β-CD molecule, a complete secondary belt is formed by these hydrogen bonds, which makes β-CD rather rigid and less soluble in water than α-CD and γ-CD. The solubilities and other physical properties of CDs are given in Table 1.

TABLE 1

Physical properties of CDs

|  | α-CD | β-CD | γ-CD |
| --- | --- | --- | --- |
| Number of glucopyranoside units | 6 | 7 | 8 |
| Molecular weight (MW) (g/mol) | 972 | 1135 | 1297 |
| Solubility in water (g/100 mL) | 14.5 | 1.85 | 23.2 |
| Melting point (° C.) | 275 | 280 | 275 |

CDs with molecular weights from 1000 Da to 2000 Da are not significantly absorbed from the gastrointestinal tract. α-CD, β-CD, and γ-CD are not hydrolyzed by human salivary and pancreatic amylases, although α-CD and β-CD can be fermented in the intestinal microflora. Because of their inertness and low tissue penetration, CDs are considered as safe expedients for oral drug delivery applications.

Among all the CDs, β-CD is the most favored one in drug delivery applications. However, unmodified β-CD cannot be so safely applied for parenteral administration because its low water solubility can cause adverse effects (e.g., nephrotoxicity, given that CDs are mainly excreted unchanged in urine). To minimize the potential side effects and improve the water solubility of β-CD, many chemically modified β-CDs have been synthesized by substituting the hydroxyl groups with various other functional groups. The strategy of these substitutions is to introduce other functional groups to break down the intramolecular hydrogen bonds of β-CD. So far, several β-CD derivatives have been produced for pharmaceutical applications, including methylated β-CDs, 2-hydroxyl-propyl β-CD, sulfobutyl ether β-CD, and others.

Poly(Ethylene Glycol) and Monomethoxy Poly(Ethylene Glycol)

Poly(ethylene glycol) (PEG) is a biocompatible and biodegradable linear polymer with the ethylene glycol repeat unit, $-(OCH_2CH_2)_n-$. The general structure of PEG is $H-(OCH_2CH_2)_n-OH$. Monomethoxy poly(ethylene glycol) (MPEG) is a derivative of PEG with the formula $CH_3-(OCH_2CH_2)_n-OH$, in which one functional —OH group is at one end of the chain and the —OH group at the other end replaced by the inert —OCH$_3$ group. MPEG is used for the preparation of bio-conjugates when an inert group is desired at an exposed end of the PEG chain to prevent cross-linking by two —OH functional groups in one PEG chain.

PEG in general is highly water soluble and also soluble in many organic solvents including dichloromethane (DCM), dimethyl sulfoxide (DMSO), chloroform, etc. Studies have revealed that each ethylene glycol subunit is associated with two to three water molecules arising from the hydrophilic nature of the polymer. PEGs and chemically modified PEGs are widely used in the fields of biology, chemistry, biomedicine and pharmacology. The beneficial properties of PEGs and their derivatives arise from their nontoxicity, non-immunogenicity, biocompatibility, biodegradability and high water solubility. PEGs have been approved by the U.S. Food and Drug Administration for internal and topical usages.

So far, PEGs have been used as covalent modifiers of a variety of substrates to produce conjugates whose properties combine the properties of PEG and the starting substrates. Studies have shown that PEG coatings on the surfaces of biological nanoparticles can enhance their water solubility, reduce renal clearance, improve controlled drug-release, provide longevity in the blood stream and ease toxicity of biomedical materials. It was also found that if coated with a low molecular weight PEG, larger particles (e.g., 200 nm and 500 nm in diameter) can decrease mucoadhesion and improve particle penetration through fresh undiluted human mucus. In comparison with their unpegylated counterparts, pegylated drugs are also generally more stable over a range of pH and temperature changes. Hence, PEGs have been widely used to modify the physical and chemical properties of biomedical materials and drugs.

There have been literature reports using PEGs and β-CD derivatives to produce β-CD containing polymers for various purposes.

This "Discussion of the Background" section is provided for background information only. The statements in this "Discussion of the Background" are not an admission that the subject matter disclosed in this "Discussion of the Background" section constitutes prior art to the present disclosure, and no part of this "Discussion of the Background" section may be used as an admission that any part of this application, including this "Discussion of the Background" section, constitutes prior art to the present disclosure.

SUMMARY OF THE INVENTION

Embodiments of the present invention relate to a compound comprising a cyclodextrin and a monoalkoxy polyethylene glycol linked thereto through an ether bond (a "pegylated cyclodextrin"), drug delivery vehicles and pharmaceutical formulations including the same, and methods for making the compound and the drug delivery vehicle and for delivering the drug to a patient in need thereof. In many embodiments, the cyclodextrin is beta-cyclodextrin. Furthermore, the monoalkoxy polyethylene glycol may be a mono-$C_1$-$C_4$-alkoxy polyethylene glycol, such as monomethoxy polyethylene glycol, monoethoxy polyethylene glycol, mono-n-propoxy polyethylene glycol, mono-i-propoxy polyethylene glycol, mono-n-butoxy polyethylene glycol, mono-i-butoxy polyethylene glycol or mono-t-butoxy polyethylene glycol.

In general, the monoalkoxy polyethylene glycol has a molecular weight of (but not limited to) 200 to 5000 g/mol. In many examples, the monomethoxy polyethylene glycol has a molecular weight of from 300 to 2000 g/mol. Furthermore, the pegylated cyclodextrin may include one or more monoalkoxy polyethylene glycol units (generally one or two monoalkoxy polyethylene glycol units). The monoalkoxy polyethylene glycol may be linked to the cyclodextrin at an (OH)2, (OH)3 or (OH)6 oxygen atom of the cyclodextrin. The cyclodextrin can also be α-cyclodextrin or γ-cyclodextrin.

The method of synthesizing a pegylated cyclodextrin generally comprises creating either a tosylated monoalkoxy polyethylene glycol or a tosylated cyclodextrin, and either (1) reacting the tosylated monoalkoxy polyethylene glycol with a deprotonated cyclodextrin, or (2) reacting the tosylated cyclodextrin with a deprotonated monoalkoxy polyethylene glycol. In either case, creating the tosylated intermediate may comprise reacting a monoalkoxy polyethylene glycol or cyclodextrin with a deprotonating agent to form a deprotonated intermediate, and reacting the deprotonated intermediate with a toluenesulfonyl halide (e.g., toluenesulfonyl chloride). The deprotonating agent may comprise an alkali metal hydride, such as sodium or potassium hydride. A molar ratio of the alkali metal hydride to the monoalkoxy polyethylene glycol or the cyclodextrin may be from 1:1 to 2:1 (e.g., 1:1 to 1.5:1, 1:1 to 1.33:1, or any another range of values between 1:1 and 2:1). The reactions may be performed in a polar solvent that is non-reactive to the deprotonating agent, such as THF, dioxane, DMSO, DMF, methylene chloride, combinations thereof, etc.

Another aspect of the present invention relates to a method of improving the water solubility of a cyclodextrin, comprising linking a monoalkoxy polyethylene glycol to the cyclodextrin through an ether bond, and dissolving the cyclodextrin with the monoalkoxy polyethylene glycol linked thereto in water. The water may comprise deionized water or an aqueous buffer solution. The method may improve the water solubility of the cyclodextrin by at least 30 times.

A further aspect of the present invention relates to a method of synthesizing an inclusion compound containing a drug and a pegylated cyclodextrin, comprising dissolving the pegylated cyclodextrin in deionized water or an aqueous buffer solution to form a (first) solution, and mixing the (first) solution with the drug to form the inclusion compound. In some embodiments, the method may further comprise dissolving the drug in a solvent, such as an organic solvent that is miscible with water and/or that is biologically compatible, to form a separate solution prior to mixing it with the cyclodextrin. The method may also further comprise lyophilizing the solution(s) after mixing to obtain the inclusion compound as a solid powder.

A still further aspect of the present invention relates to a method of delivering a drug to a patient in need thereof, comprising creating an inclusion compound comprising the drug and a pegylated cyclodextrin, and administering an effective amount of the drug in the inclusion compound to the patient. In one example, the inclusion compound is administered to the patient through a membrane including mucin (e.g., a mucus membrane). The pegylated cyclodextrin is believed to prevent the drug from directly contacting the mucin. However, the inclusion compound is not limited to mucosal administration, and can be delivered orally, parenterally, etc., so that the inclusion compound and/or drug is taken up by cells in the body of the patient.

The present invention may also relate to a method to decrease the interaction between mucin and an inclusion compound containing a drug for delivery and a cyclodextrin, comprising forming a cyclodextrin linked to a monoalkoxy polyethylene glycol unit through an ether bond, creating an inclusion compound comprising the monoalkoxy polyethylene glycol-linked cyclodextrin and the drug for delivery, and exposing the inclusion compound to a biological system containing mucus. The monomethoxy polyethylene glycol unit is believed to prevent the drug for delivery from directly contacting the mucin.

One of the purposes of the present invention is to chemically modify CDs including β-CD with a monoalkoxy polyethylene glycol such as monomethoxy poly(ethylene glycol) (MPEG) to increase its water solubility. MPEG modified CDs are a form of pegylated CDs. The present invention produces pegylated CDs (FIG. 3) that can be used as drug carriers and/or in other industrial applications to improve the water solubility and/or other properties of CDs. For example, pegylated β-CDs may be improved as expedients for oral, topical and parenteral drug delivery applications due to their increased water solubility, biocompatibility and controlled drug release. The methods disclosed herein allow the ether (C—O—C) bond between the MPEG units and the CD, which in the case of β-CD, preserves the original opening of the β-CDs cavity for forming inclusion complexes with drug molecules. Pegylated β-CDs in the present invention can reduce the adverse effect of β-CD and improve other preferred properties for pharmaceutical applications due to the properties of MPEG. Because PEGs have been approved for pharmaceutical use by the US FDA, pegylated β-CDs can have many or all of the favored properties of PEGs for pharmaceutical applications. Pegylated β-CDs and other CDs may reduce nephrotoxicity, improve controlled drug-release and/or drug stability, prolong blood circulation time, and/or ease other possible toxic effects of CDs including β-CD. Attachment of MPEG (low molecular weight) to CDs including β-CD may reduce the molecular interaction of the CD with biological molecules when used to deliver drugs through mucus.

FIGS. 2A-C show static structural models of monopegylated β-CD at the β-CD sites of (OH)6 (FIG. 2A), (OH)2 (FIG. 2B) and (OH)3 (FIG. 2C), respectively, where nine ethylene glycol repeat units with a methoxy group end cap are shown. The Gaussian 09W program was used to make the structural models. The PEG chains can have a number of other conformations, though, and the conformations may be quite dynamic in a water environment. More than one MPEG chain can also be chemically attached to a single β-CD, although the structures are not shown herein.

These and other advantages of the present invention will become readily apparent from the detailed description of various embodiments below.

BRIEF DESCRIPTION OF THE DRAWINGS

FIG. 21 shows a scheme for making Ts-β-CDs and the possible structures of Ts-β-CDs.

FIG. 23B shows the COSY correlations among the U-region in the spectrum of FIG. 23A.

FIG. 24D shows correlations of the 7 and 8 protons with those of the H1 protons in the ROESY spectrum of FIG. 24A.

DETAILED DESCRIPTION

Figure 1A:
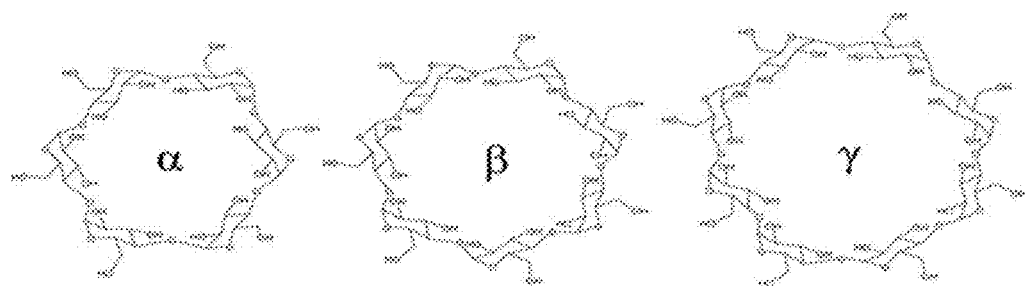
FIGS. 1A-C show chemical structures of α-CD, β-CD and γ-CD (FIG. 1A), 3-dimensional shapes and sizes of α-CD, β-CD and γ-CD (FIG. 1B), and position labels (from 1 to 6) of the α-D(+)-glucopyranoside unit (FIG. 1C).
Figure 1B:
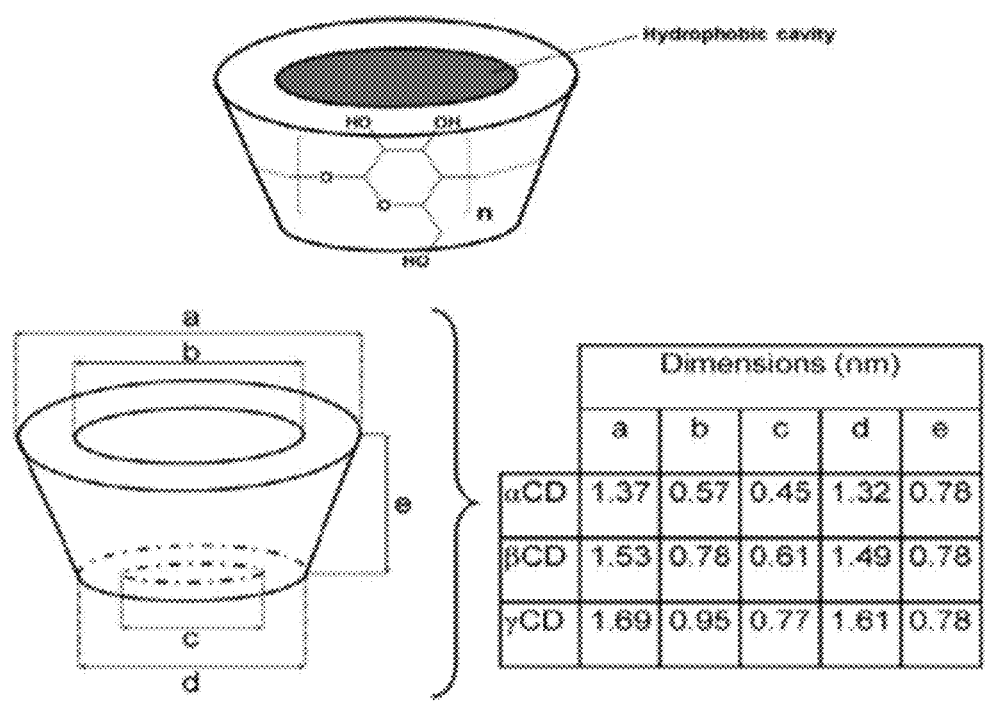
Figure 1C:
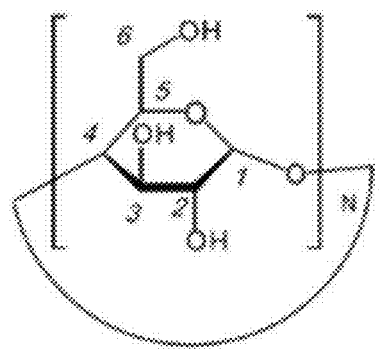
Figure 2A:
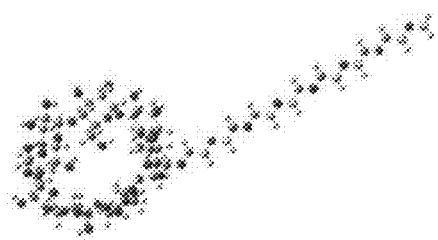
FIGS. 2A-C show structural models of single pegylated β-CDs with MPEG attached to the (OH)6 site (FIG. 2A), the (OH)2 site (FIG. 2B), and the (OH)3 site (FIG. 2C).
Figure 2B:
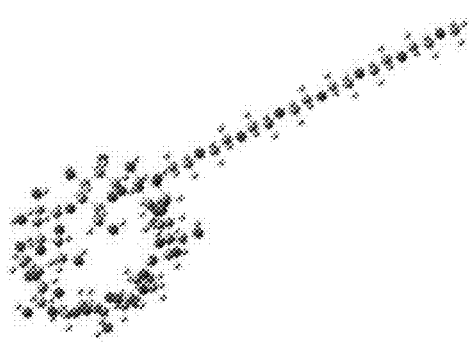
Figure 2C:
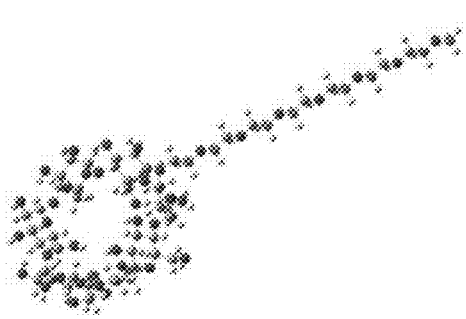

Reference will now be made in detail to various embodiments of the invention, examples of which are illustrated in the accompanying drawings. While the invention will be described in conjunction with the following embodiments, it will be understood that the descriptions are not intended to limit the invention to these embodiments. On the contrary, the invention is intended to cover alternatives, modifications and equivalents that may be included within the spirit and scope of the invention as defined by the appended claims. Furthermore, in the following detailed description, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

The technical proposal(s) of embodiments of the present invention will be fully and clearly described in conjunction with the drawings in the following embodiments. It will be understood that the descriptions are not intended to limit the invention to these embodiments. Based on the described embodiments of the present invention, other embodiments can be obtained by one skilled in the art without creative contribution and are in the scope of legal protection given to the present invention.

Furthermore, all characteristics, measures or processes disclosed in this document, except characteristics and/or processes that are mutually exclusive, can be combined in any manner and in any combination possible. Any characteristic disclosed in the present specification, claims, Abstract and Figures can be replaced by other equivalent characteristics or characteristics with similar objectives, purposes and/or functions, unless specified otherwise.

The invention, in its various aspects, will be explained in greater detail below with regard to exemplary embodiments.

Exemplary Methods of Synthesizing Pegylated CDs Materials

All chemicals were used as received from the manufacturers without further purification. Dichloromethane ($CH_2Cl_2$, CAS #: 75-09-2), MPEGs (CAS #: 9004-74-4), p-toluenesulfonyl chloride (p-TsCl, CAS #: 98-59-9), pyridine (Pr, CAS #: 110-86-1), sodium hydroxide (NaOH, CAS #: 1310-73-2), and acetone (CH3OCH3, CAS#: 67-64-1) were purchased from Sigma-Aldrich. Ethyl ether anhydrous ($Et_2O$, CAS #: E-198-4) and hydrochloric acid (HCl, CAS #: 7732-18-5) were from Fisher Scientific. Deuterated water ($D_2O$, CAS#: 7789-20-0) and deuterated dimethyl sulfoxide (DMSO-$d_6$, CAS#: 2206-27-1) were purchased from Cambridge Isotope Laboratories, Inc.

Synthesis of Tosylated Monomethoxy Poly(Ethylene Glycol) (MPEG-Ts)

The route to synthesize MPEG-Ts intermediates is shown below. The MPEG-Ts intermediates were prepared from MPEG350 (MPEG with average molecular weight 350 Da), MPEG550 (MPEG with average molecular weight 550 Da), MPEG750 (MPEG with average molecular weight 750 Da) and MPEG2000 (MPEG with average molecular weight 2000 Da). The amount of reagents and the solvents used are listed in Table 2.

TABLE 2

Reactants and solvents used for the syntheses of MPEG-Ts intermediates

|  | MPEG350 | MPEG550 | MPEG750 | MPEG2000 |
|---|---|---|---|---|
| MPEG(g/mmol) | 8.27/23.62 | 13.00/23.63 | 16.04/21.40 | 10.47/5.24 |
| $CH_2Cl_2$ (mL) | 70 | 70 | 70 | 70 |
| Pyridine (mL) | 40 | 40 | 40 | 40 |
| p-TsCl (g/mmol) | 6.89/36.14 | 6.89/36.14 | 5.66/29.70 | 8.26/43.30 |

The synthetic procedure shown above is conducted in more detail as follows. To a solution of MPEG dissolved in $CH_2Cl_2$, an excess molar amount of p-TsCl and pyridine were added. Pyridine (Pr) was used to neutralize (remove the proton) the hydrochloric acid (HCl) released from the reaction. The mixture was left for reaction overnight at 0° C. The product solution was extracted using a mixture of 50 mL of ice water and 40 mL of concentrated HCl solution (12.1M). The organic phase was collected and successively washed with a 3M HCl solution, a saturated NaCl solution and a solution of 5% $NaHCO_3$, then dried with anhydrous magnesium sulfate ($MgSO_4$). After removing the hydrated $MgSO_4$ by gravity filtration, the filtrates were concentrated by rotary evaporation and further purified by precipitation with diethyl ether.

C-1-3. Synthesis of Pegylated β-CD (MPEG-β-CD)

The procedure for synthesis of the MPEG-β-CDs is shown briefly below. Both DMF and DMSO were used as solvents. DMF may be preferred because it gives a higher yield and shows no restrictions with any MPEGs. However, when DMSO is used, the reactivity of β-CD with some MPEGs such as MPEG2000 is relatively higher. β-CD (molecular formula $C_{42}H_{49}O_{14}(OH)_{21}$) was dried at 90° C. for 12 hours. An excess of NaH was added to a DMF solution of β-CD to deprotonate the hydroxyl groups. The mixture was stirred for half an hour, and then filtered to get the filtrate. MPEG-Ts in DMF was added to the β-CD solution, and the mixed solution was sealed and stirred at 60-65° for one or more days (typically two or more days). The crude pegylated β-CDs were precipitated in diethyl ether, filtered and purified using dialysis in distilled water and/or size exclusion chromatography. The purified MPEG-β-CDs were collected after freeze drying. Syntheses of pegylated β-CD were processed with different MPEG-Ts intermediates as described herein. The amount of each reactant, as well as the volume of each solvent used, is shown in Table 3.

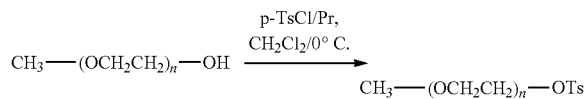

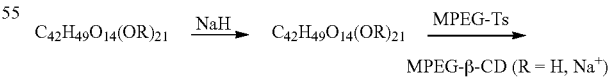

TABLE 3

Reactants and solvents used for the syntheses of MPEG-β-CDs

|  | MPEG350-Ts | MPEG550-Ts | MPEG750-Ts | MPEG2000-Ts | MPEG2000-Ts |
|---|---|---|---|---|---|
| MPEG-Ts (g)/(mmol) | 3.5478/7.09 | 3.5523/5.07 | 4.004/4.00 | 4.53/2.265 | 4.60/2.30 |

TABLE 3-continued

Reactants and solvents used for the syntheses of MPEG-β-CDs

|  | MPEG350-Ts | MPEG550-Ts | MPEG750-Ts | MPEG2000-Ts | MPEG2000-Ts |
|---|---|---|---|---|---|
| β-CD (g)/(mmol) | 2.1125/1.86 | 2.1125/1.86 | 2.6/2.3 | 2.6 g/2.3 | 2.0/1.76 |
| Solvent (mL) | DMF (120) | DMF (120) | DMF (120) | DMF (120) | DMSO (80) |
| NaH (g)/(mmol) | 0.964/40.29 | 0.964/40.29 | 1.1651/48.55 | 1.1652/48.55 | 1.198/49.92 |

Synthesis of Tosylated β-CD

The procedure to synthesize tosylated β-CD (Ts-β-CD) is shown below. Briefly, TsCl (2.663 g, 0.014 mol) and β-CD (10.247 g, 0.009 mol) are added in 250 mL deionized water. The mixture was stirred under $N_2$ gas for two hours at room temperature. Next, 4.13 g NaOH (pellet) (~0.1 mol) is added to the solution. The solution is stirred further for 30 minutes, and then filtered to remove unreacted TsCl. 40.0 mL of 2.6 M HCl is added to the filtrate to adjust the pH of the solution to 7. The solution is cooled with an ice water bath to precipitate Ts-β-CD (white solid). The crude product is washed a few times with acetone, resulting in 3.326 g of Ts-β-CD, corresponding to a yield of ~30%.

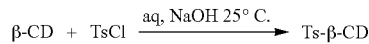

β-CD + TsCl $\xrightarrow{\text{aq, NaOH 25° C.}}$ Ts-β-CD

Syntheses of Pegylated β-CD from Monomethoxy Poly (Ethylene Glycol) and Tosylated β-CD The procedure of the synthesis of MPEG-β-CD is shown below. The amount of each reactant as well as the volumes of solvents are given in Table 3. Briefly, in a glove box, MPEG is dissolved in DMF. An excess amount of NaH is added to the solution. The mixture is stirred for half an hour to de-protonate the hydroxyl groups of the MPEG, and then the mixture is filtered to obtain a filtrate. Ts-β-CD in DMF is added to a solution of the filtrate. The combined solution is sealed and stirred at 60-65° for one or more days (typically two or more days). The solvent was then removed using a vacuum pump at low temperature. The solid crude product was dissolved in de-ionized water, followed by filtration to remove any insoluble particles. The solution was transferred to a dialysis cassette and dialyzed against deionized water for one or more days (typically two or more days). The water was refreshed periodically during the dialysis. Finally, the product was lyophilized to get the purified product as a white powder.

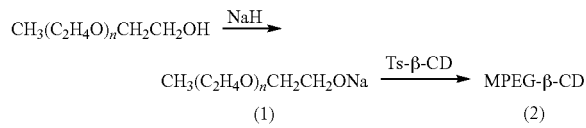

TABLE 4

Reactants and solvents used for the syntheses of MPEG-β-CDs

|  | MPEG350 | MPEG550 | MPEG750 |
|---|---|---|---|
| MPEG (g)/(mmol) | 2.723/7.14 | 3.267/5.94 | 3.400/4.93 |
| Ts-β-CD (g) | 1.655 | 1.367 | 1.720 |

TABLE 4-continued

Reactants and solvents used for the syntheses of MPEG-β-CDs

|  | MPEG350 | MPEG550 | MPEG750 |
|---|---|---|---|
| DMF (mL) | 60 | 60 | 60 |
| NaH (g)/(mmol) | 0.19/8.3 | 0..175/7.3 | 0.132/0.5 |

Structural Characterization of Pegylated CDs

NMR Characterization of MPEG-Ts

Figure 3:
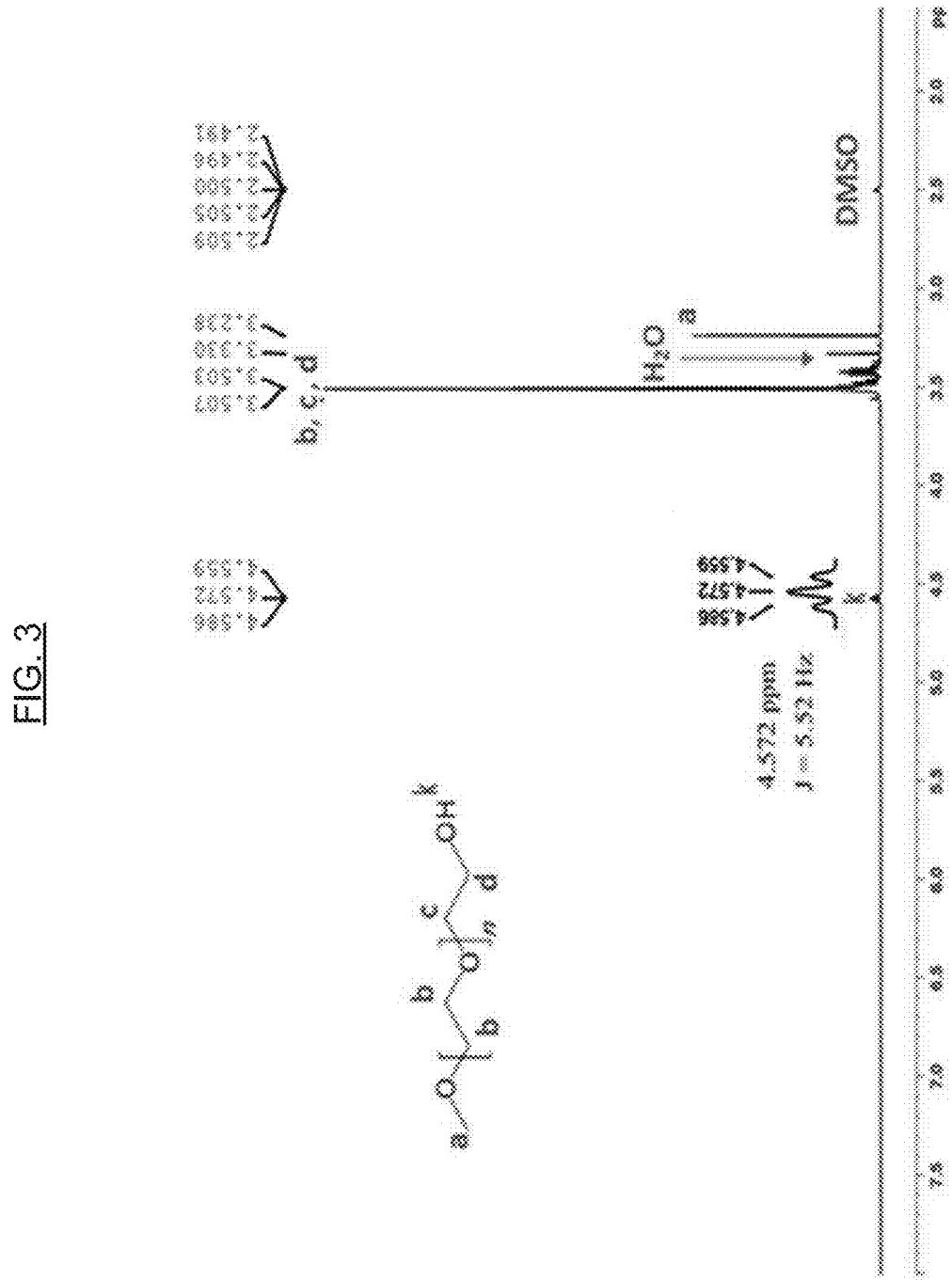
FIG. 3 shows a $^1$H NMR spectrum of MPEG550 dissolved in DMSO-$d_6$.

The $^1$H NMR spectra of MPEG550 dissolved in DMSO-$d_6$ is shown in FIG. 3. The chemical shift of DMSO-$d_6$ at 2.500 ppm is used as the secondary reference for the chemical shift. The MPEG structural formula and its labels for the hydrogen positions are shown in the inset of FIG. 3. The hydroxyl proton shows a triplet peak with chemical shift at 4.572 ppm and J-coupling constant 5.52 Hz, due to the J-couple with the d proton. The chemical shifts of the b protons are at 3.507 ppm. The peak of the c protons overlaps with that of the b protons, and the peak d protons appear as the right lower shoulder by the b peak. The methyl proton, a, shows a chemical shift at 3.238 ppm. The peaks at 3.330 ppm arise from absorbed water in the solution. There are also other insignificant peaks in the spectrum which are mistrial (e.g., not identified and/or assigned), but that typically exist in commercial MPEGs. The same spectral patterns and chemical shifts were observed for MPEG350, MPEG750 and MPEG2000, but with different b peak intensities relative to the a and k peaks due to the different molecular weights.

Figure 4:
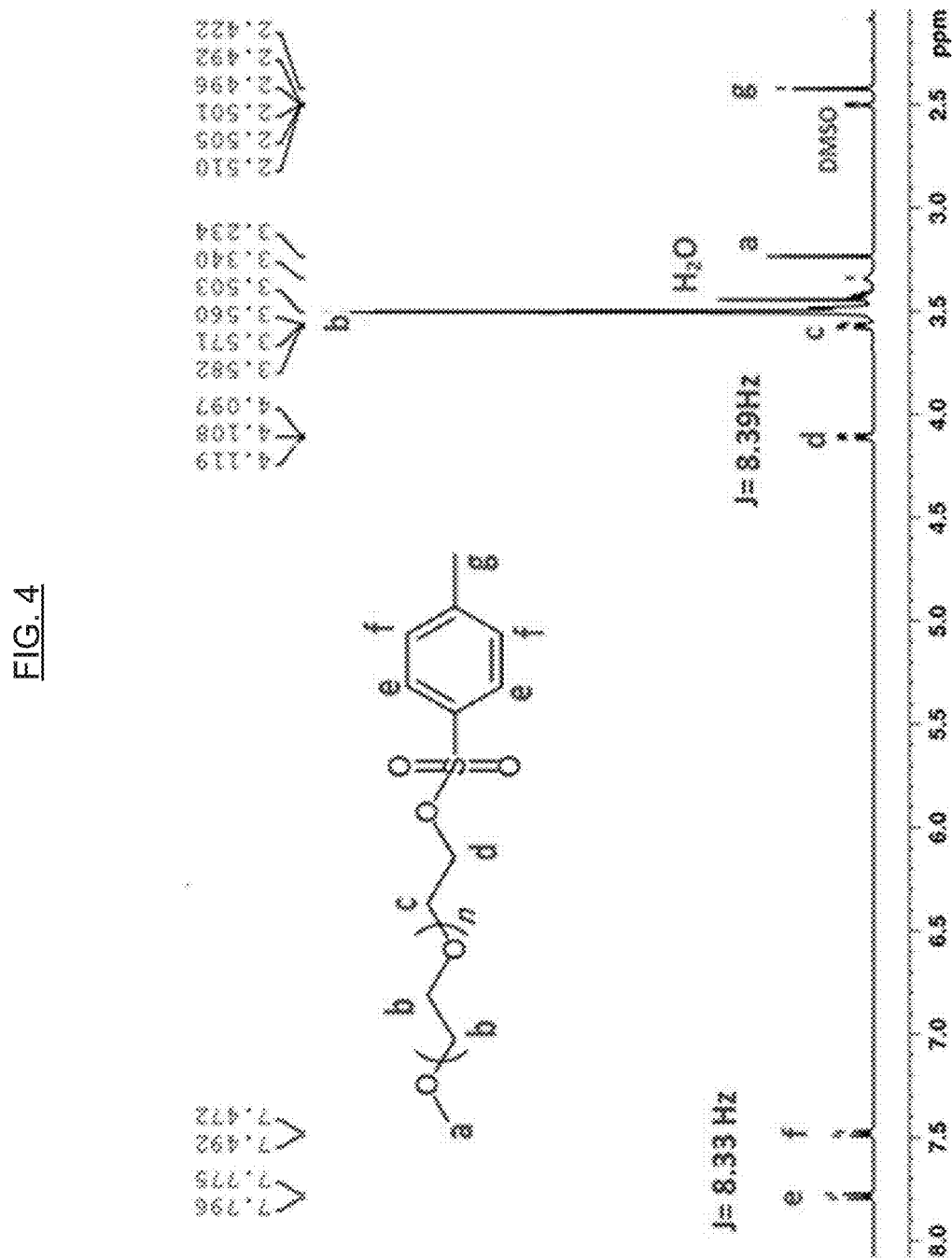
FIG. 4 shows a $^1$H NMR spectrum of MPEG550-Ts dissolved in DMSO-$d_6$.

The $^1$H NMR spectrum of MPEG550-Ts dissolved in DMSO-$d_6$ is shown in FIG. 4. The hydroxyl proton signal at 4.572 ppm in FIG. 3 vanishes, demonstrating that the hydroxyl hydrogen atom was replaced by the solely possible p-toluenesulfonyl group as shown in the structural formula of MPEG-Ts in FIG. 4, in which the sulfur atom directly bonds to the hydroxyl oxygen atom. The appearance of the AB quartet at 7.796 ppm/7.775 ppm and 7.492 ppm/7.472 ppm with J=8.32 Hz shows the e protons and f protons associated with the aromatic ring of the p-toluenesulfonyl group. The peak at 2.422 ppm shows the methyl protons, g, of the p-toluenesulfonyl group. Tosylation of the MPEG dramatically changed the chemical shifts of the d and c protons. The chemical shifts of the d and c protons now moved to higher frequencies at 4.108 ppm and 3.571 ppm, respectively, due to the electron drawing effect of the $S(=O)_2$ group that makes the d and c protons deshielded. The d and c peaks have triplet patterns with J=8.39 Hz due to the coupling with each other. (More evidence is in the 2D NMR spectra for assigning the d and c protons.) The peak g at 2.422 ppm is from the methyl protons of the p-toluenesulfonyl group. The $^1$H NMR spectra of MPEG350-Ts, MPEG750-Ts and MPEG2000-Ts look similar to that of the MPEG550-Ts but with different b peak intensities.

Figure 5:
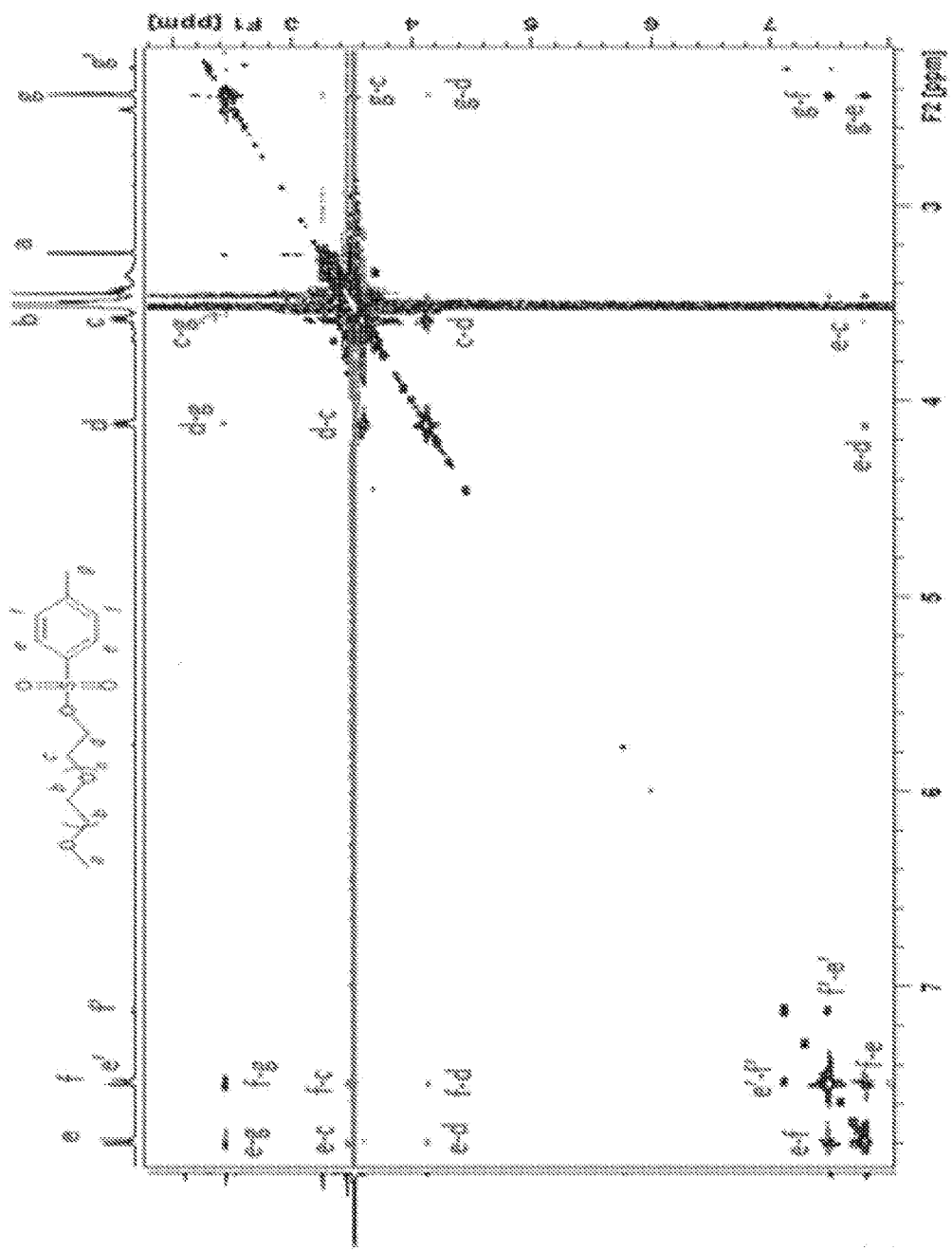
FIG. 5 shows the NOESY NMR spectrum of the MPEG550-Ts dissolved in DMSO-$d_6$.

¹H ROESY and COSY 2D NMR techniques were used to confirm the formation of the MPEG-Ts intermediates and the assignments of the proton peaks. FIG. 5 shows the NOESY NMR spectrum of the MPEG550-Ts dissolved in DMSO-d$_6$. The 1D spectrum as shown in FIG. 4 is placed on top of the 2D spectrum. We have used a sample where a trace amount of free p-toluenesulfonyl chloride remained in the intermediate to acquire the ROESY and COSY NMR spectra for comparison in order to confirm the peak assignments of the p-toluenesulfonyl group bound to the MPEG. In FIG. 5, it clearly shows that e, f and g protons of the p-toluenesulfonyl group are correlated by the cross-peaks e-f, e-g and f-g. The d and c protons are correlated by the cross peaks d-c, respectively, due to their spatial proximities. In addition, e, f and g protons correlate with the d and c protons by the cross peaks of e-c, c-d, f-c, f-d, c-g and d-g. This shows that d and c protons are spatially close to the p-toluenesulfonyl group. The corresponding proton signals of the free p-toluenesulfonyl chloride are labeled as e', f' and g', respectively. It shows that the e', f' and g' protons are correlated to each other by the cross-peaks e'-f', and f'-g'. However, they are not correlated to the d and c protons, showing that the corresponding p-toluenesulfonyl chloride molecules were not chemically connected to the MPEG chains. The red arrow points to the c-g cross-peak.

Figure 6:
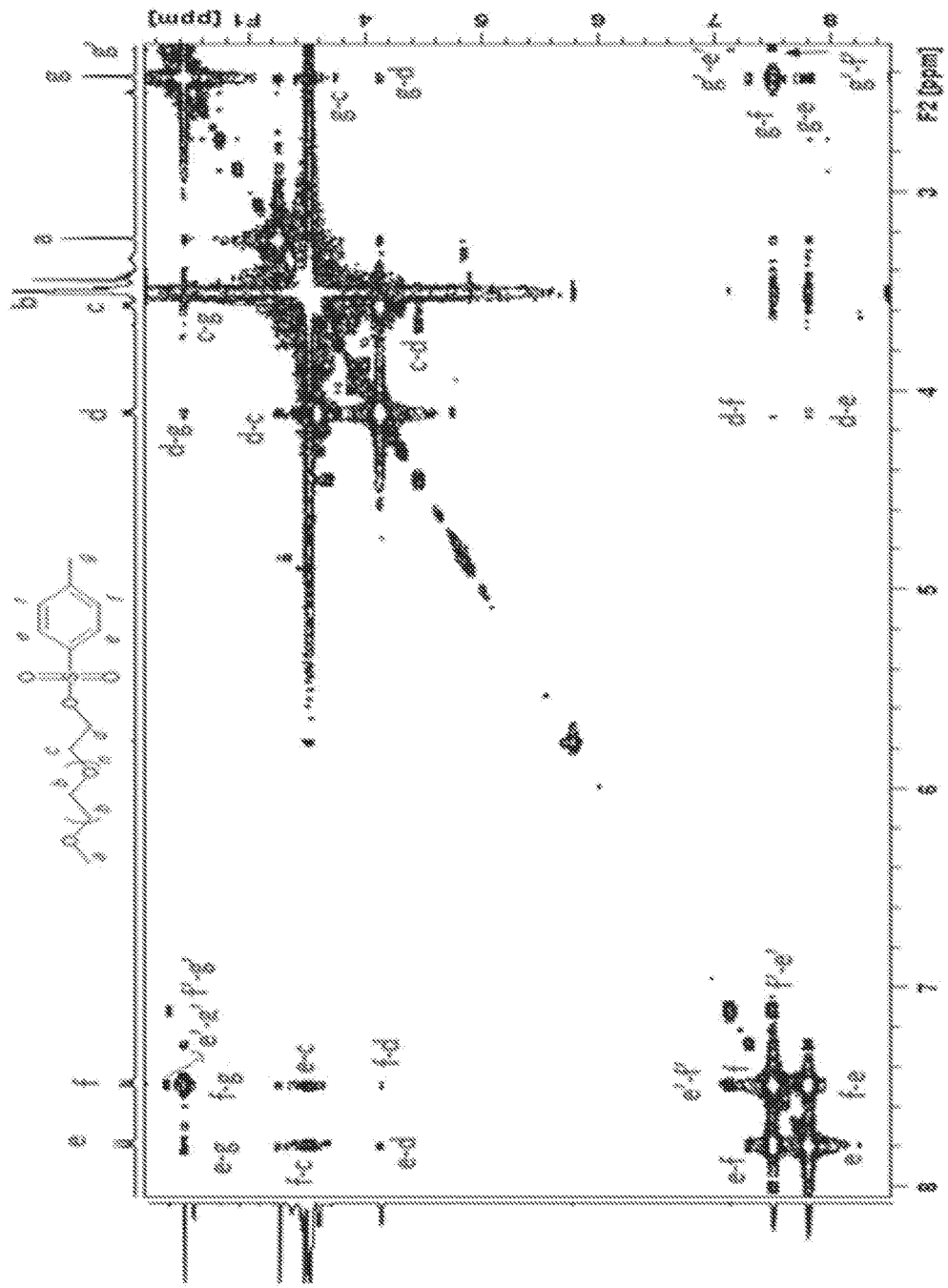
FIG. 6 shows the COSY NMR spectrum of MPEG550-Ts dissolved in DMSO-$d_6$.

FIG. 6 shows the COSY NMR spectrum of MPEG550-Ts dissolved in DMSO-d$_6$. All of the peaks and cross-peaks are labeled as in the ROESY spectrum of FIG. 5. The cross peaks show the J-coupled connectivities through chemical bonds between the MPEG and the p-toluenesulfonyl group. The e', f' and g' peaks are correlated by the cross-peaks e'-f', e'-g' and f'-g'. The ROESY and COSY NMR spectra of FIGS. 5-6 demonstrate that tosylated MPEGs were successfully synthesized.

NMR Characterization of MPEG-β-CDs Synthesized from MPEG-Ts Intermediates

The formation of pegylated β-CDs via the reaction of MPEG-Ts intermediates with β-CD were confirmed by the results of NMR and MALDI TOF mass spectrometry techniques. The success of the experiments was also confirmed by the physical properties of the MPEG-β-CD products. All NMR spectra were acquired in D$_2$O and DMSO-d$_6$ solvents, separately.

Figure 7:
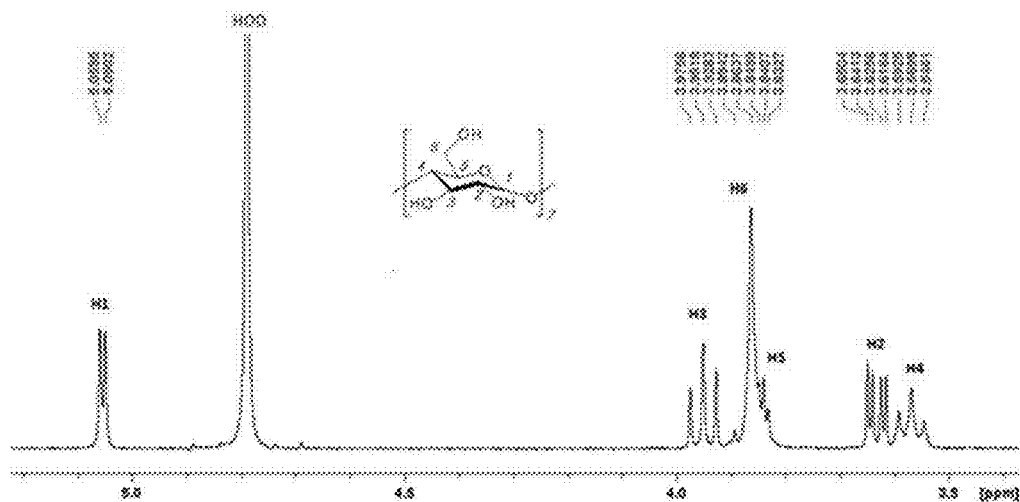
FIG. 7 is a $^1$H NMR spectrum of β-CD dissolved in $D_2O$.
Figure 8:
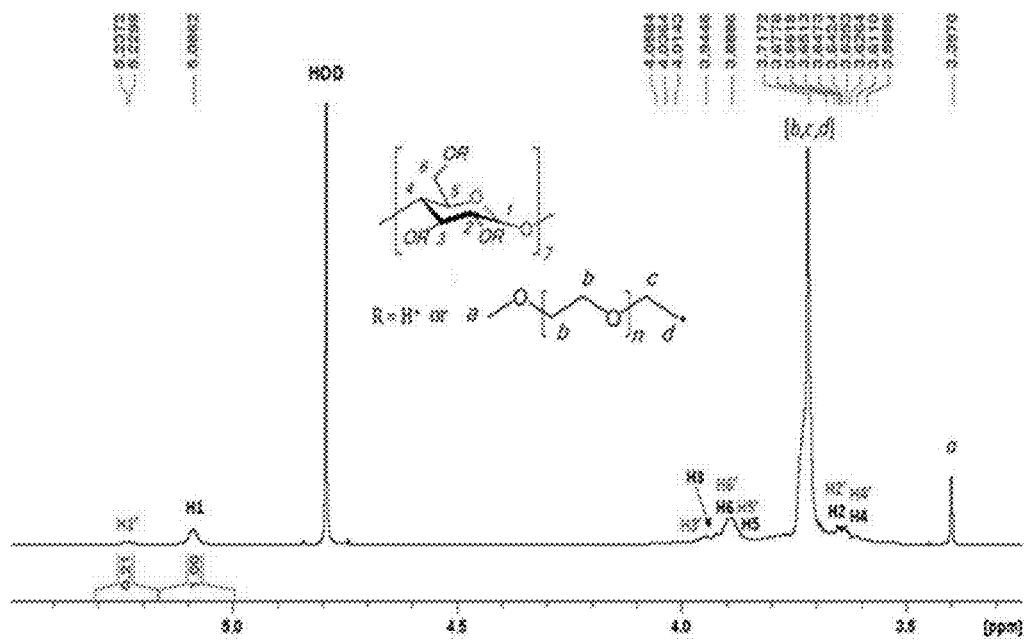
FIG. 8 is a $^1$H NMR spectrum of MPEG550-β-CD dissolved in $D_2O$.
Figure 9:
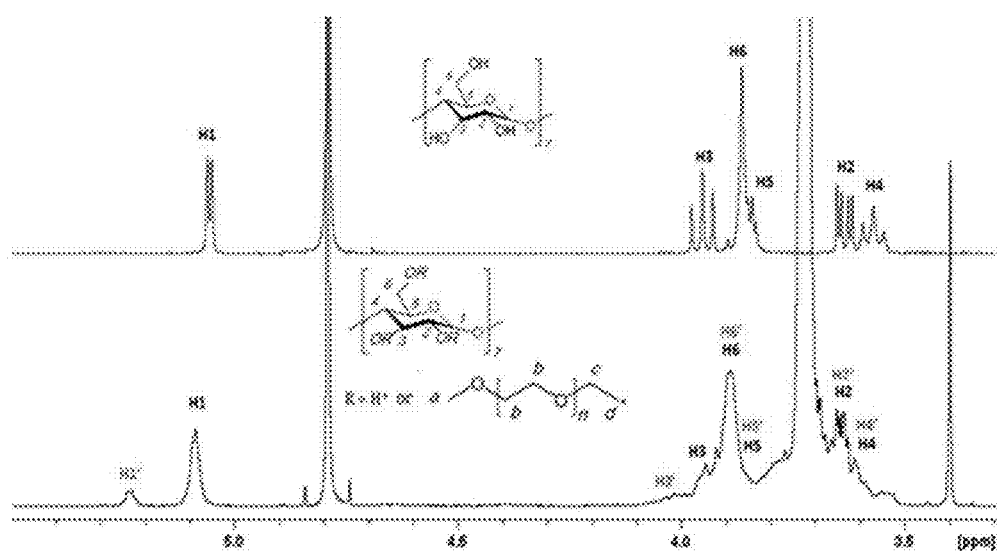
FIG. 9 is a comparison of $^1$H NMR spectra of β-CD (upper) and MPEG550-β-CD (lower) dissolved in $D_2O$.
Figure 10:
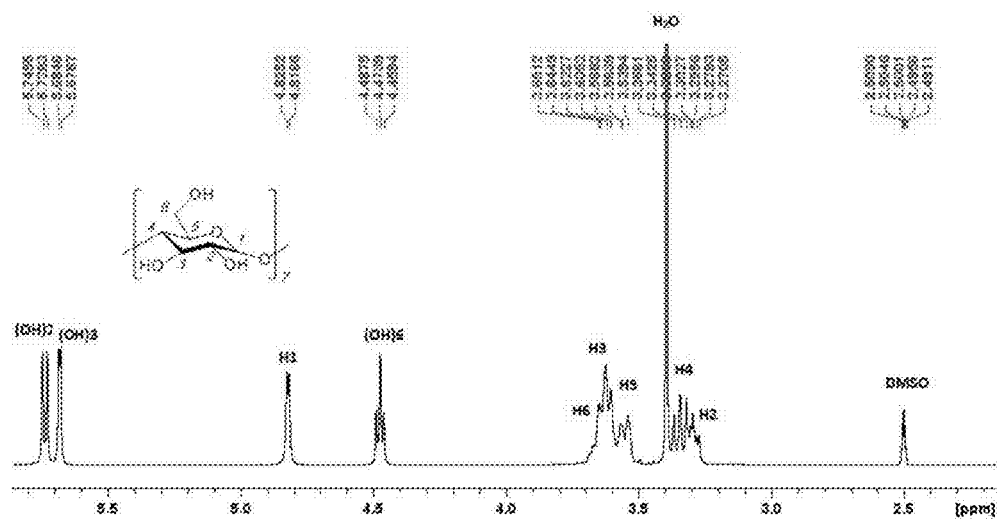
FIG. 10 is a $^1$H NMR spectrum of β-CD dissolved in DMSO-$d_6$.
Figure 11:
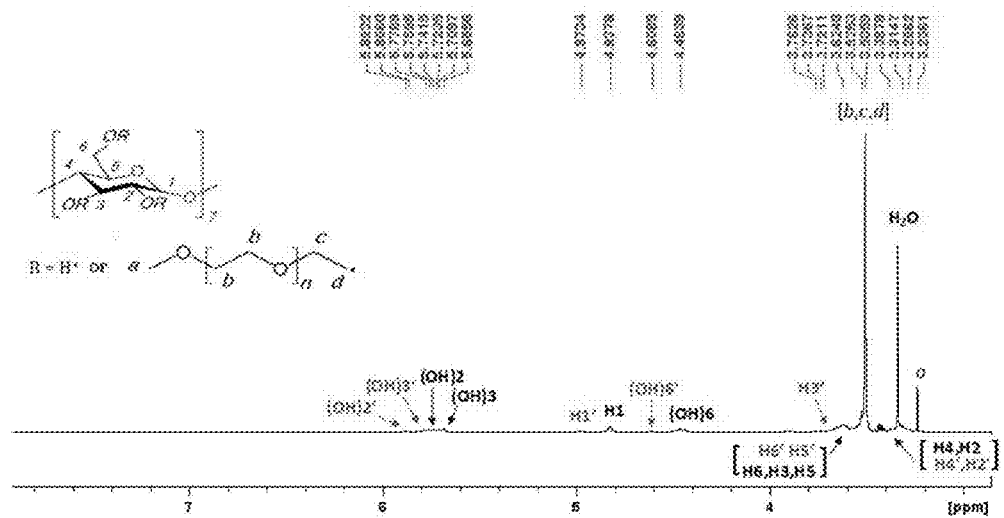
FIG. 11 is a $^1$H NMR spectrum of MPEG550-β-CD dissolved in DMSO-$d_6$.
Figure 12:
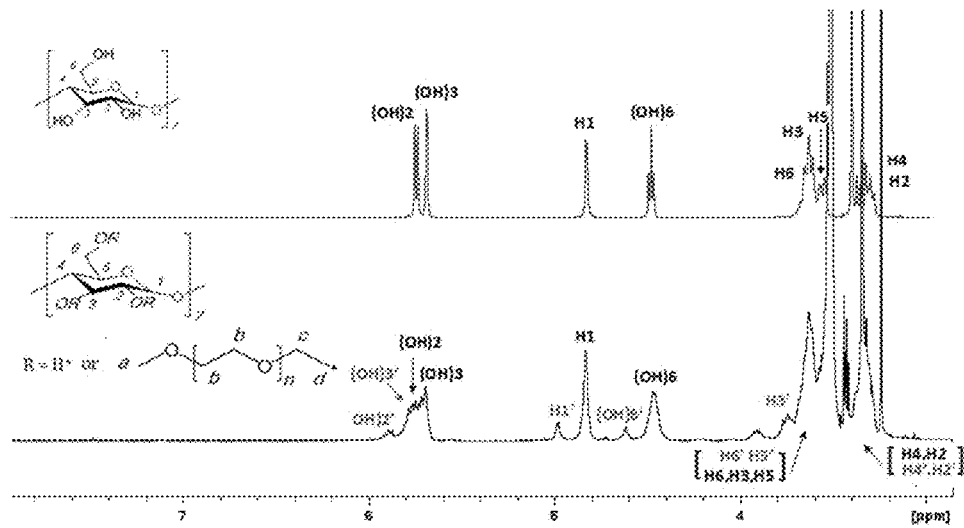
FIG. 12 is a comparison of $^1$H NMR spectrum of β-CD (upper) and MPEG550-β-CD (lower) dissolved in DMSO-$d_6$.

FIG. 7 shows the ¹H NMR spectrum of β-CD dissolved in D$_2$O, and FIG. 8 shows the ¹H NMR spectrum of MPEG550-β-CD dissolved in D$_2$O. FIG. 9 shows a comparison of these two spectra. FIG. 10 shows the ¹H NMR spectrum of β-CD dissolved in DMSO-d$_6$, and FIG. 11 shows the ¹H NMR spectra of MPEG550-β-CD dissolved in DMSO-d$_6$. FIG. 12 shows a comparison of these two spectra. The NMR spectra of MPEG350-β-CD, MPEG750-β-CD and MPEG2000-β-CD dissolved in D$_2$O and DMSO-d$_6$ look similar to those of the MPEG550-β-CD. Thus, the MPEG550-β-CD spectrum is shown as a representative example. The reason to use D$_2$O is that the signals of hydroxyl protons of (OH)2, (OH)3 and (OH)6 do not appear in the spectra (due to proton/deuterium exchange), which allows us to identify other possible peaks, if any, overlapping with those hydroxyl peaks. The reason to use DMSO-d$_6$ is to see the (OH)2, (OH)3 and (OH)6 hydroxyl protons. In addition, the chemical shifts are slightly different in D$_2$O and in DMSO-d$_6$, which helps to recognize and/or identify the peaks.

Chemical shifts are determined by local chemical structures. Thus, the formation of MPEG-β-CD can be recognized by the changes in the proton chemical shifts before and after the pegylation of β-CD. These changes are summarized in Table 5 and Table 6 below for the compounds dissolved in D$_2$O and DMSO-d$_6$, respectively. Signals from the tosyl groups as in the spectra of MPEG550-Ts (FIG. 4) disappeared in FIG. 8 and FIG. 11, showing that pegylation occurred and the free Ts groups in the products were significantly removed. Once the hydrogen in the hydroxyl groups of (OH)2, (OH)3 or (OH)6 of β-CD is replaced by the MPEG (see the insets in FIG. 8 and FIG. 11), the nearby protons should become less shielded, resulting in higher chemical shifts. The underlying reason is due to the greater electron withdrawing effect of MPEG relative to a proton (or hydroxyl group). This phenomenon can be seen in the NMR spectral comparisons in FIG. 9 and FIG. 12. The chemical shift changes for all the MPEG-β-CDs are also listed in Table 5 (D$_2$O) and Table 6 (DMSO-d$_6$).

The changes in the H1 proton (¹H) chemical shifts are quite significant after pegylation. The H1 protons are less shielded, resulting in higher chemical shifts after the β-CD molecule was bound to a MPEG. In addition, the H1 doublets became broader in the MPEG-β-CDs, which shows that more H1 peaks overlap with each other in this region. More significantly, new overlapping proton signals appear around 5.20 ppm for the MPEG-β-CDs dissolved in D$_2$O and around 4.97 ppm in DMSO-d$_6$. We believe that these signals belong to H1 protons, and thus are labeled as H1' in the spectra.

The H3 protons show a triplet-like pattern (exact pattern being a doublet-doublet due to the coupling with the H1 and H4 protons) for β-CD dissolved in D$_2$O. After pegylation, the H3 protons evolved into two groups of H3 peaks, one labeled as H3 and the other H3'. The H3' peaks are more deshielded. The H3 peaks in the MPEG β-CDs partially overlap with those of the H6 and H5 protons. These phenomena were also seen when DMSO-d$_6$ was used as the solvent. Here, the original H3 peaks of the β-CD overlap with those of the H5 and H6 peaks. Changes or new peaks are also observed for the other peaks H4, H5 and H6 as shown in the spectra and in Tables 5 and 6.

TABLE 5

Proton chemical shifts (ppm) of β-CD, MPEGs and MPEG-β-CDs dissolved in D$_2$O

| Protons | β-CD | MPEG350-β-CD | MPEG550-β-CD | MPEG750-β-CD | MPEG2000-β-CD |
| --- | --- | --- | --- | --- | --- |
| H1 | 5.0549 | 5.0579 | 5.0862 | 5.0553 | 5.0859 |
| H1' | — | 5.2084 | 5.2335 | 5.2051 | 5.2044 |
| H2 | 3.6210-3.6459 | 3.5621-3.6611 | 3.5886-3.6778 | 3.5586-3.6618 | 3.5461-3.6054 |
| H2' | — | 3.5621-3.6611 | 3.5886-3.6778 | 3.5586-3.6618 | 3.5461-3.6054 |
| H3 | 3.9519 | 3.9406 | 3.9461 | 3.9325 | 3.9135-3.9265 |
| H3' | — | 3.9886 | 4.0364 | 4.0053 | 3.9786-4.0392 |
| H4 | 3.5394 | 3.5621-3.6611 | 3.5886-3.6778 | 3.5586-3.6618 | 3.5461-3.6054 |
| H4' | — | 3.5621-3.6611 | 3.5886-3.6778 | 3.5586-3.6618 | 3.5461-3.6054 |
| H5 | 3.8411 | 3.8279-3.9183 | 3.8346-3.9229 | 3.8230 | 3.8095-3.8975 |

TABLE 5-continued

Proton chemical shifts (ppm) of β-CD, MPEGs and MPEG-β-CDs dissolved in D₂O

| | | | | | |
|---|---|---|---|---|---|
| H5' | — | 3.5621-3.6611 | 3.5886-3.6778 | 3.5586-3.6618 | 3.5461-3.6054 |
| H6 | 3.8637 | 3.8639 | 3.8886 | 3.8656 | 3.8560 |
| H6' | — | 3.5621-3.6611 | 3.5886-3.6778 | 3.5586-3.6618 | 3.5461-3.6054 |
| CH3 | — | 3.3720 | 3.3970 | 3.3665 | 3.3685 |
| (CH2)n | — | 3.6911 | 3.7172 | 3.6872 | 3.6904 |

Free MPEG

| | | MPEG350 | MPEG550 | MPEG750 | MPEG2000 |
|---|---|---|---|---|---|
| CH3 | — | 3.3676 | 3.3731 | 3.3648 | 3.3712 |
| (CH2)n | — | 3.6908 | 3.6936 | 3.6874 | 3.6938 |

TABLE 6

Proton chemical shifts (ppm) of β-CD, MPEG and MPEG-β-CD dissolved in DMSO-d₆

| Protons | β-CD | MPEG350-β-CD | MPEG550-β-CD | MPEG750-β-CD | MPEG2000-β-CD |
|---|---|---|---|---|---|
| H1 | 4.8209 | 4.8250 | 4.8278 | 4.8257 | 4.8269 |
| H1' | — | 4.9769 | 4.9734 | 4.9773 | 4.9746 |
| H2 | 3.2749-3.2992 | 3.2733-3.3712 | 3.2862-3.3867 | 3.2734-3.4045 | 3.2774-3.3824 |
| H2' | — | 3.2733-3.3712 | 3.2862-3.3867 | 3.2734-3.4045 | 3.2774-3.3824 |
| H3 | 3.6227 | 3.6276 | 3.6248 | 3.6278 | 3.6273 |
| H3' | — | 3.7399 | 3.7401 | 3.7399 | 3.7423 |
| H4 | 3.3429 | 3.2733-3.3712 | 3.2862-3.3867 | 3.2734-3.4045 | 3.2774-3.3824 |
| H4' | — | 3.2733-3.3712 | 3.2862-3.3867 | 3.2734-3.4045 | 3.2774-3.3824 |
| H5 | 3.5572 | 3.5870-3.6860 | 3.5555-3.5637 | 3.5581-3.5654 | 3.5470-3.6290 |
| H5' | — | 3.5870-3.6860 | 3.5555-3.5637 | 3.5581-3.5654 | 3.5470-3.6290 |
| H6 | 3.6667 | 3.5870-3.6860 | 3.6760-3.6950 | 3.6955-3.6907 | 3.5470-3.6290 |
| H6' | — | 3.5870-3.6860 | 3.6760-3.6950 | 3.6955-3.6907 | 3.5470-3.6290 |
| (OH)3 | 5.6817 | 5.6799 | 4.6856 | 5.6841 | 5.6926 |
| (OH)2 | 5.7369 | 5.7341 | 5.7505 | 5.7427 | 5.7391 |
| (OH)6 | 4.4736 | 4.4594 | 4.4639 | 4.4621 | 4.4619 |
| (OH)2—(OH)3 | 5.6787-5.7455 | 5.6774-5.7879 | 5.8656-5.8822 | 5.6841-5.8803 | 5.6899-5.8778 |
| (OH)3' | — | 5.7658 | 4.5789 | 5.7762 | 5.7730 |
| (OH)2' | — | 5.8697 | 5.8741 | 5.8722 | 5.8796 |
| OH)6' | — | 4.6090 | 4.6089 | 4.6807 | 4.6104 |
| CH3 | — | 3.2459 | 3.2361 | 3.2357 | 3.2355 |
| (CH2)n | — | 3.5054 | 3.5059 | 3.5055 | 3.5049 |
| (OH)MPEG | — | — | — | — | 4.5747 |

Free MPEG

| | | MPEG-350 | MPEG-550 | MPEG-750 | MPEG-2000 |
|---|---|---|---|---|---|
| CH3 | — | 3.2372 | 3.2375 | 3.2372 | 3.2362 |
| (CH2)n | — | 3.5069 | 3.5068 | 3.5069 | 3.5056 |
| (OH)MPEG | — | 4.5723 | 4.5722 | 4.5724 | 4.5714 |

Proton chemical shifts of hydroxyl groups (OH)2, (OH)3 and (OH)6 in β-CD and MPEG-β-CDs can be observed in DMSO-d₆. Comparison of the spectra in FIG. 12 shows that all the proton chemical shifts of the (OH) groups are influenced significantly by the pegylation. The proton chemical shifts of the (OH) groups evolved into two groups, (OH)2/(OH)2', (OH)3/(OH)3' and (OH)6/(OH)6'. The (OH) 6' peaks are believed to be due to the MPEG being attached to the (OH)2 and/or (OH)3 oxygen atoms, the (OH)2' peaks are believed to be due to the MPEG being attached to the (OH)3 and/or (OH)6 oxygen atoms, and the (OH)3' peaks are believed to be due to the MPEG being attached to the (OH)2 and/or (OH)6 oxygen atoms. Thus, all of these hydroxyl protons may be substituted by a MPEG.

The H1' peaks may arise from the H1 protons in the α-D(+)-glucopyranoside units to which the MPEG has been attached. The more hydroxyl protons that are replaced by MPEG units, the more the H1 protons are deshielded. We think that the MPEG attached to the (OH)6 oxygen atom just slightly shifted the H1 peak, which just made the H1 peak look broader, while the MPEG being attached to the (OH)2 or (OH)3 oxygen atom caused the overlapping broad H1' peaks. Similar considerations apply to the H3 and H3' protons.

Figure 13:
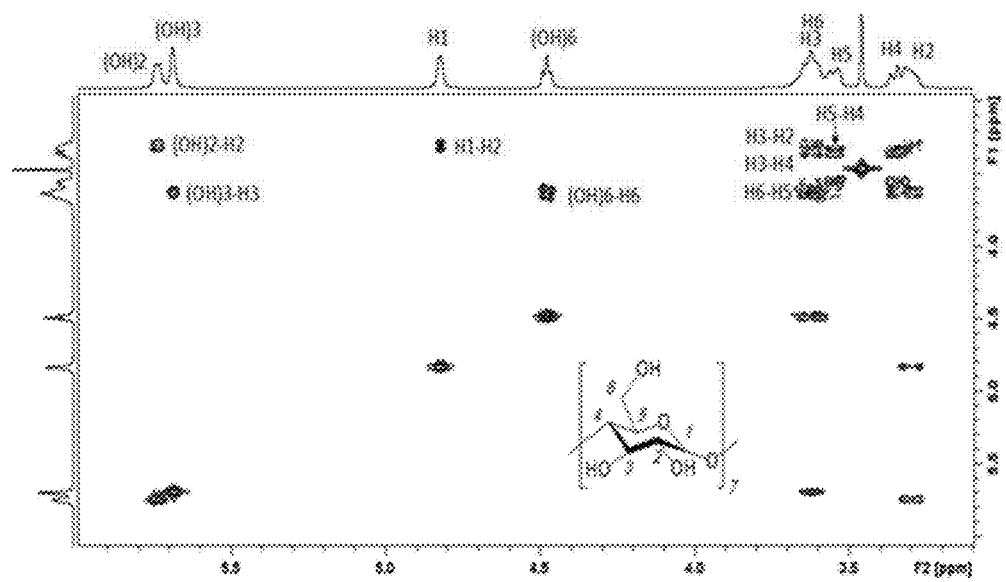
FIG. 13 is a COSY NMR spectrum of β-CD dissolved in DMSO-$d_6$.

All the ¹H peak assignments in the β-CD dissolved in DMSO-d₆ are demonstrated by the 2D COSY spectrum in FIG. 13. The cross-peaks in COSY spectrum show the correlations of protons that are J-coupled together through chemical bonds. Thus, the J-coupled protons can be clearly identified as labeled in the spectrum.

Figure 14:
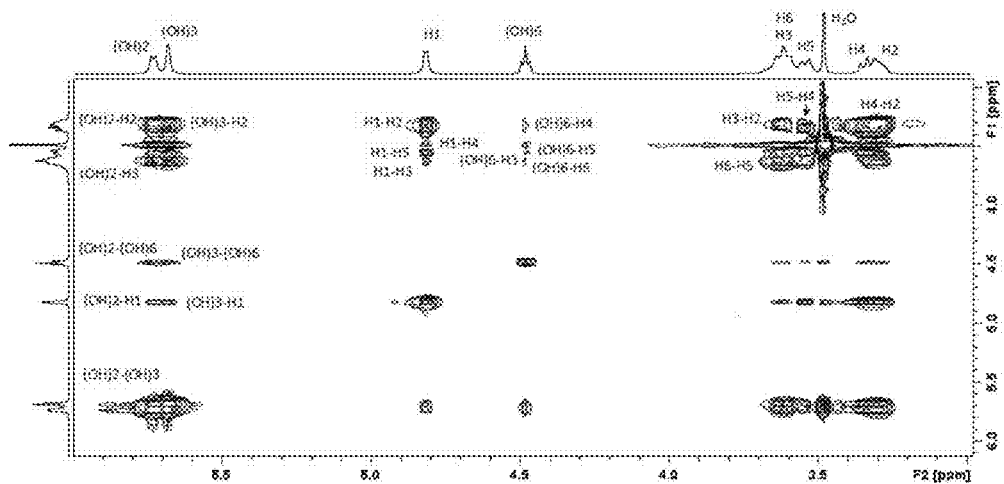
FIG. 14 is a ROESY NMR spectrum of β-CD dissolved in DMSO-$d_6$ solvent.

FIG. 14 shows the 2D ROESY NMR spectrum of β-CD dissolved in DMSO-d₆. The ROESY NMR spectrum shows the correlations of protons that are spatially close to each other (e.g., within about 5 Å). The correlations are labeled in the spectrum.

Figure 15:
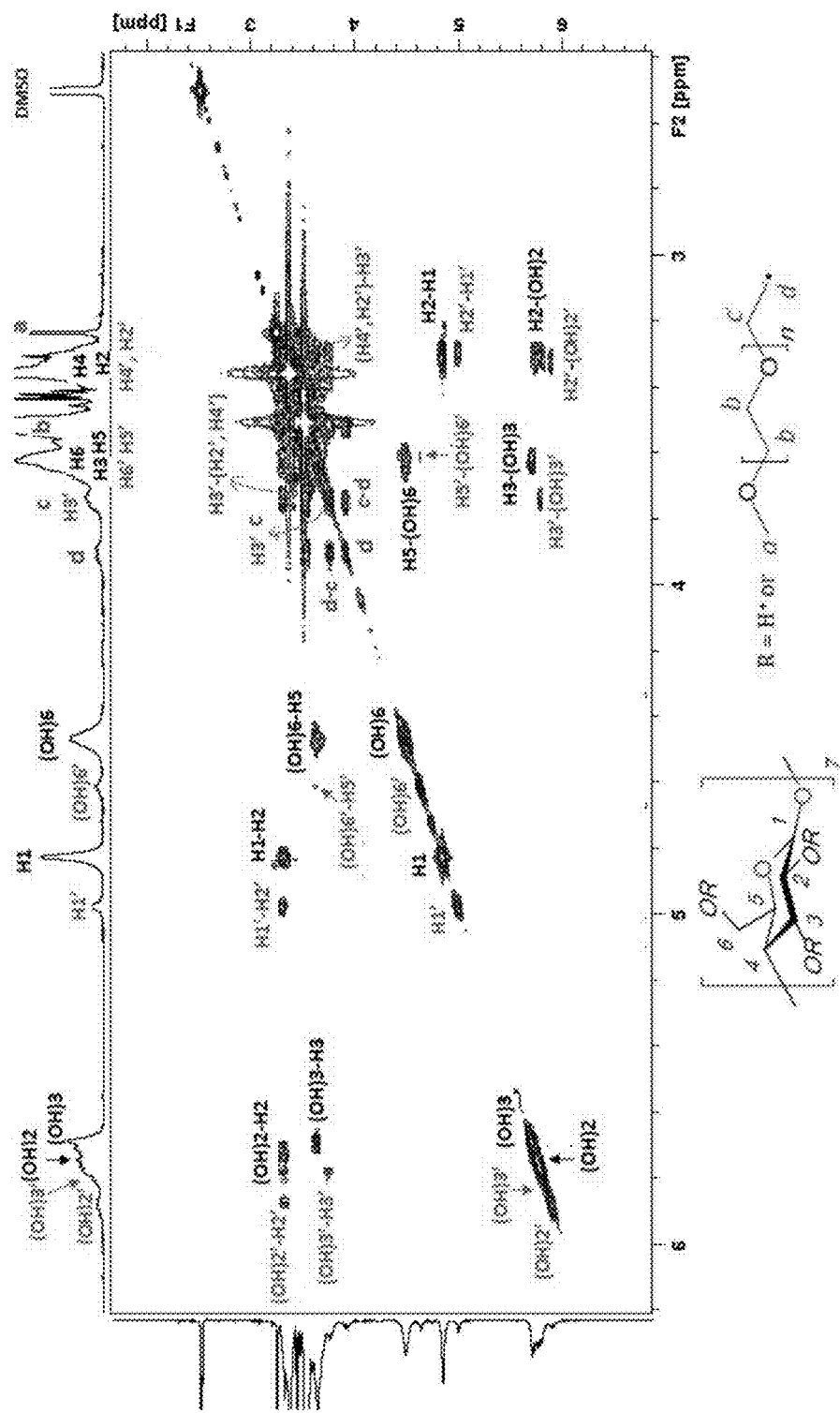
FIG. 15 is a 2D $^1$H COSY NMR MPEG550-β-CD dissolved in DMSO-$d_6$.
Figure 16:
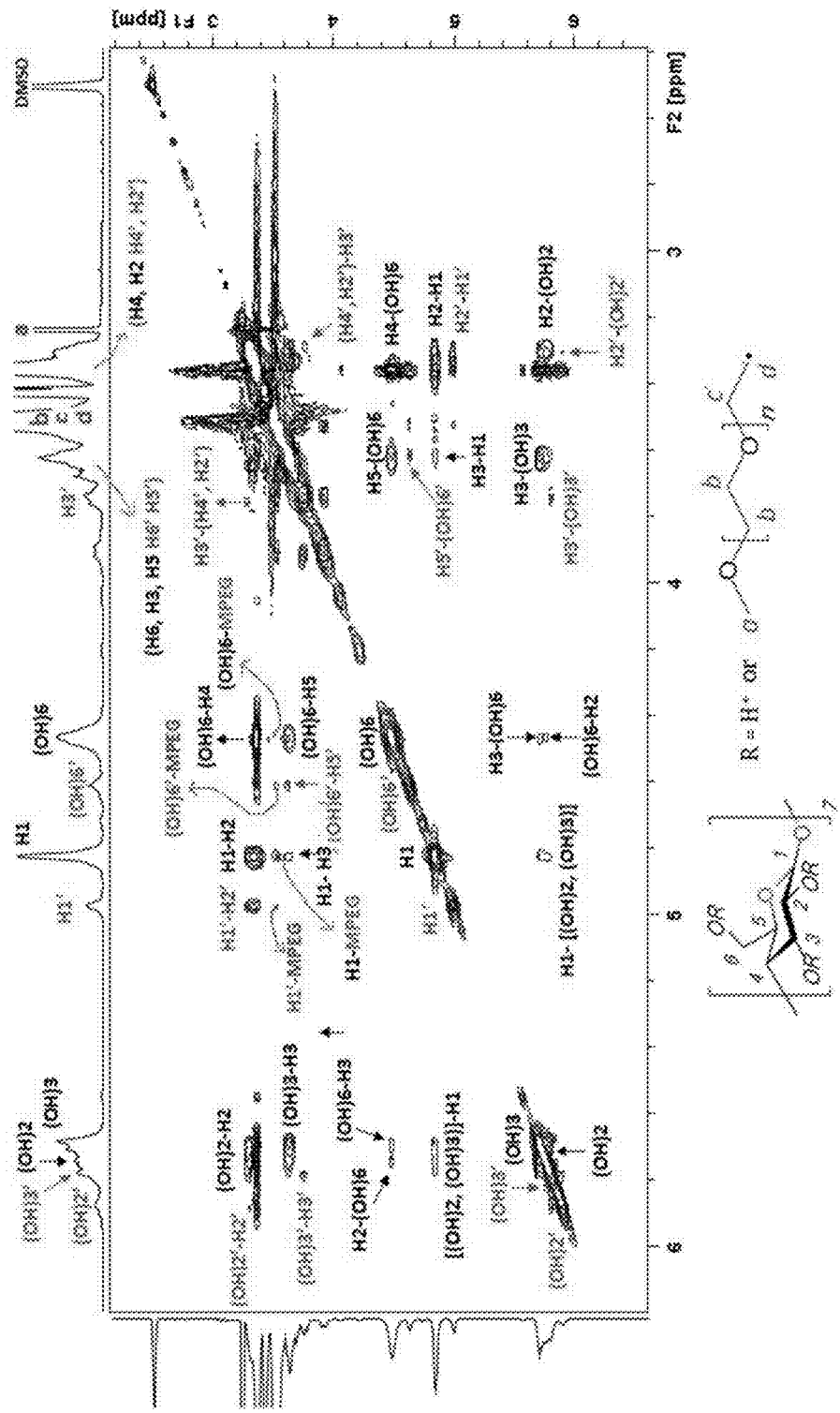
FIG. 16 is a 2D $^1$H ROESY NMR spectrum of MPEG550-β-CD dissolved in DMSO-$d_6$.
Figure 17:
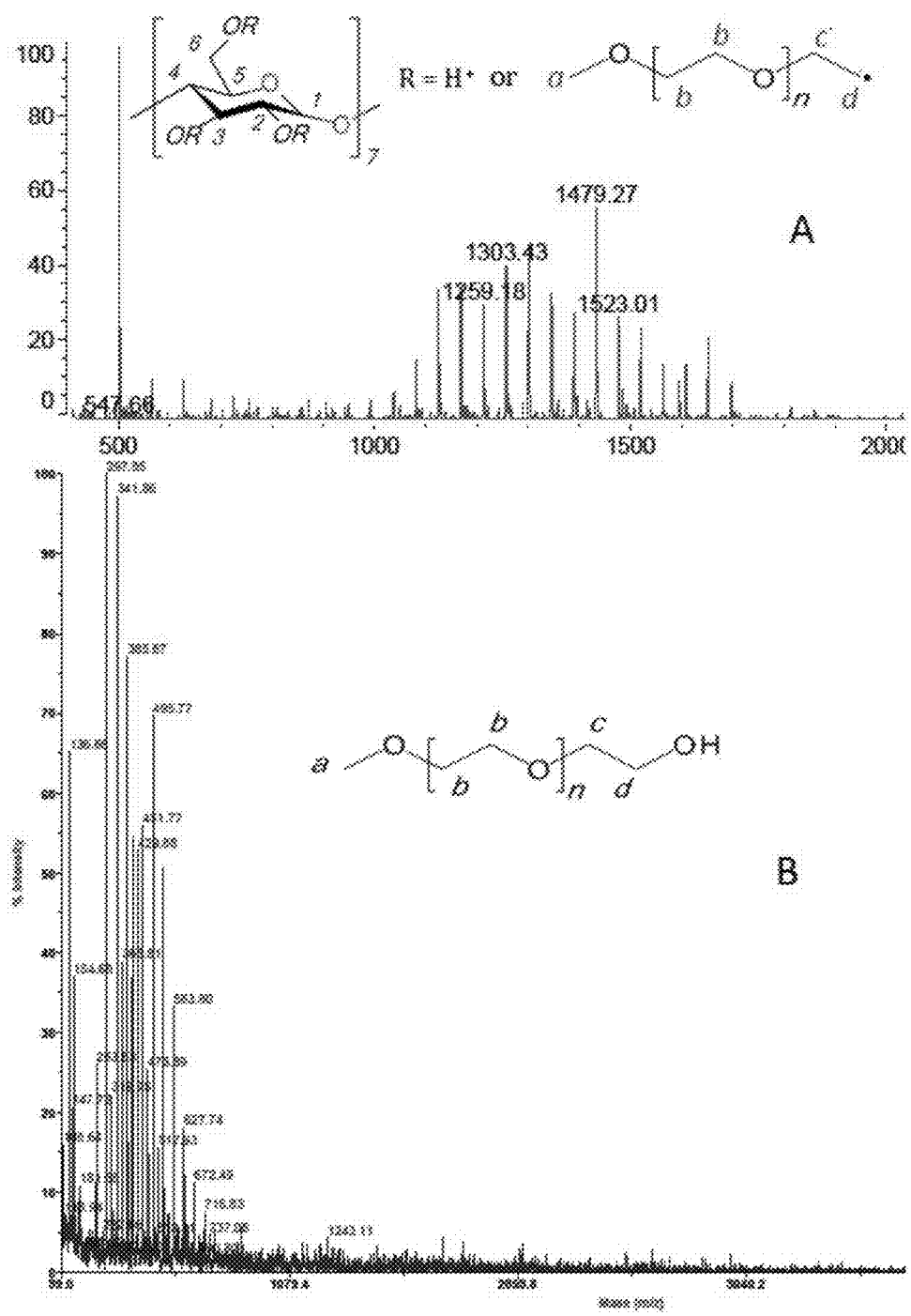
FIG. 17 shows a MALDI TOF mass spectra of MPEG350 (B) and MPEG350-βCD (A).
Figure 18:
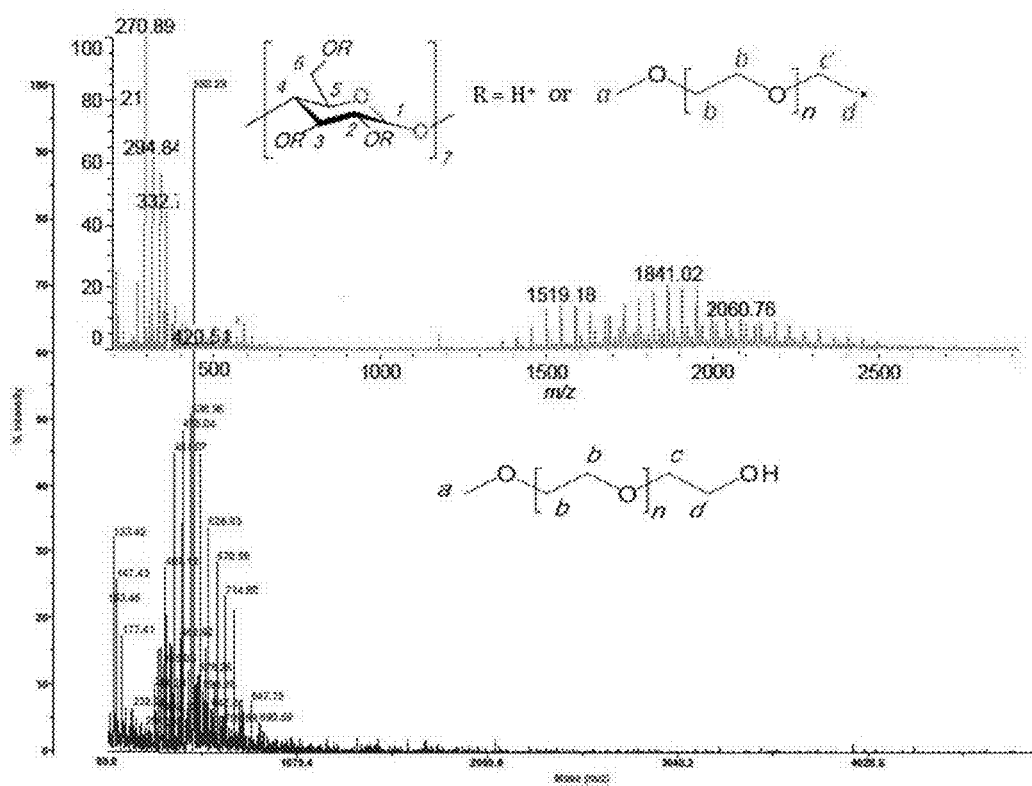
FIG. 18 shows a MALDI TOF mass spectra of MPEG550-βCD (A) and MPEG550 (B).
Figure 19:
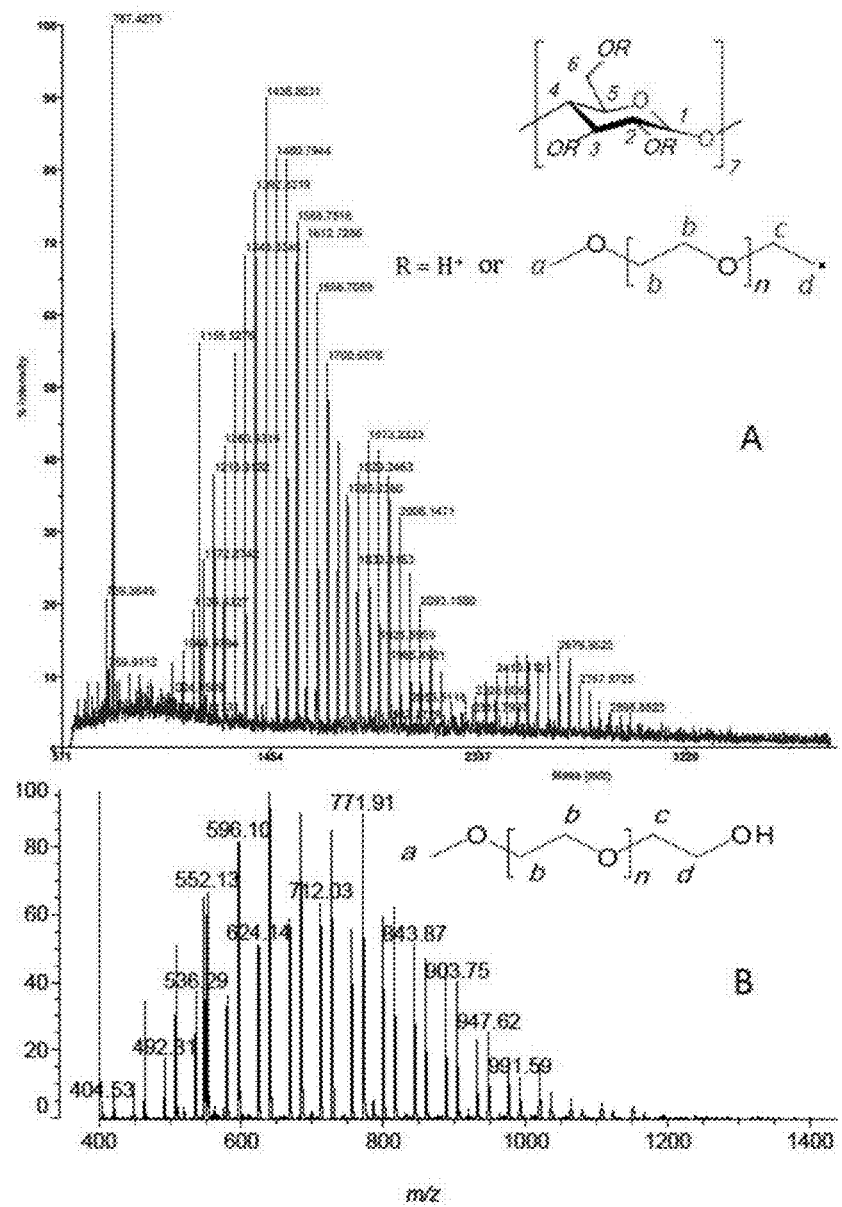
FIG. 19 shows a MALDI TOF mass spectra of MPEG750-βCD (A) and MPEG750 (B).
Figure 20:
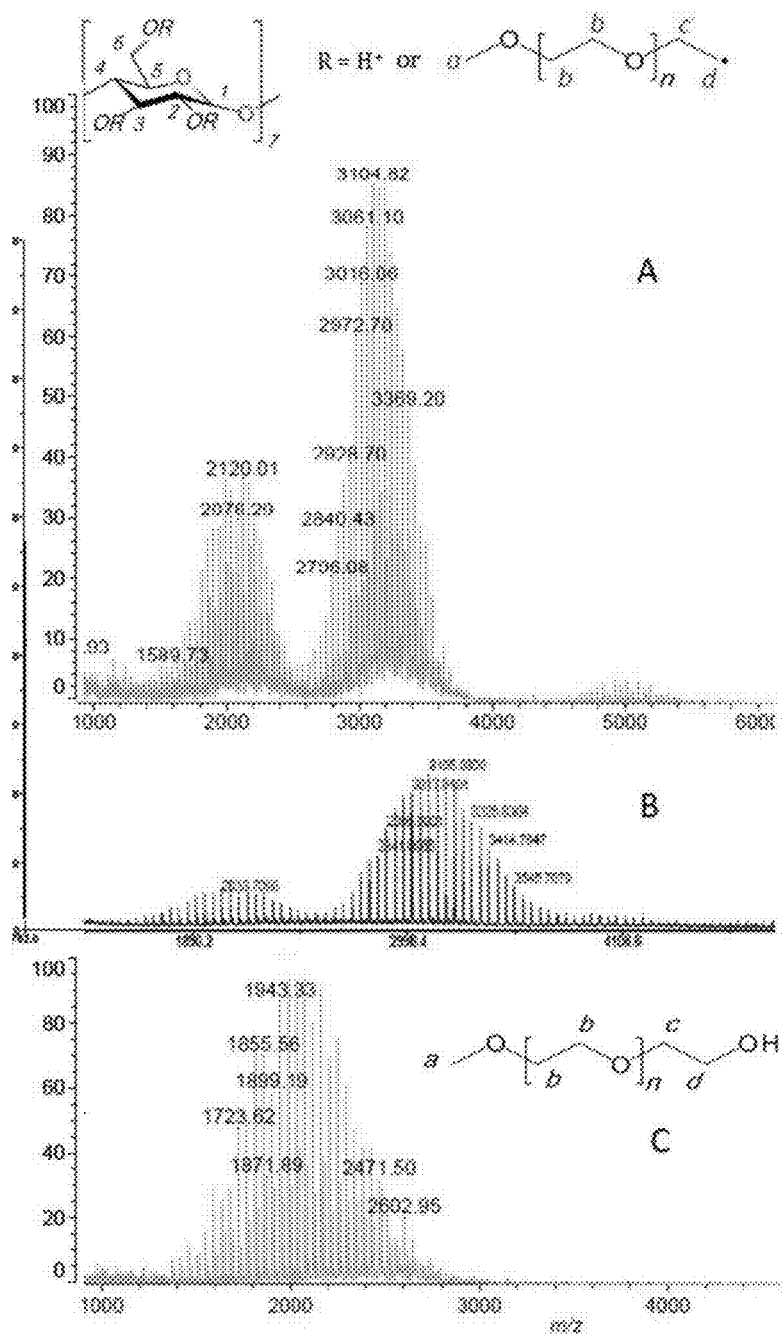
FIG. 20 shows a MALDI TOF mass spectra of MPEG2000-βCD synthesized in DMSO solvent (A) and DMF solvent (B), and a MALDI TOF mass spectra of MPEG2000 (C).

FIG. 15 shows the 2D COSY and FIG. 16 shows the 2D ROESY spectra for MPEG550-β-CD dissolved in DMSO-d₆. All correlations are labeled in the spectra. The correlations of MPEG peaks with β-CD peaks in FIG. 16 demonstrate that the MPEG is chemically attached to the β-CD.

The mixing time for the 2D $^1$H ROESY NMR spectrum of MPEG550-β-CD in FIG. 16 was 200 ms.

MALDI TOF Mass Spectral Characterization of MPEG-β-CDs Synthesized from MPEG-Ts Intermediates The samples were prepared as follows. Dihydroxybenzoic acid (DHB) was used as a matrix. 10.5 mg of the matrix was dissolved in 1 mL of deionized water, and the sample was dissolved in the matrix. 1 μL of the sample in the matrix solution was spotted on the matrix plate and dried in air. The sample was run in linear mode, and the acceleration voltage was 25,000 V.

FIGS. 17-20 show the MALDI TOF mass spectra of the MPEG-β-CDs. The spectra in FIGS. 17, 18, 19(B) and 20(C) were taken at and/or analyzed by the TAMU Protein Chemistry Lab at Texas A&M University (via Science Exchange). FIGS. 19(A) and 20(A)-(B) were taken at and/or analyzed by the University of Southern California. An Axima CFR MALDI-TOF (via Science Exchange) and an AB Applied SystemVoyager-De™ STIR Biospectrometry Workstation were used to analyze the mass spectra.

NMR Characterizations of Tosylated β-CD

FIG. 21 shows a scheme for making tosylated β-CDs and the structures of tosylated β-CDs. All OH groups, including (OH)6, (OH)2 and (OH)3, can in principle be tosylated, which are shown by X, Y and Z, respectively, in FIG. 21. There are a total of 7 cyclic α-D(+)-glucopyranoside molecules that form a β-CD. Thus, if 'a' α-D(+)-glucopyranoside rings are tosylated, the number of free α-D(+)-glucopyranoside rings will be 7 minus 'a'. The probability for the (OH)2 and (OH)3 groups to be tosylated is believed to lower than that of the (OH)6 group due to steric effects. Since a molar ratio of TsCl to β-CD of 1.55 to 1.00 was used, it is believed that most of the experimental products described in this section contain mono-tosylated β-CDs and some di-tosylated β-CDs, although multi-tosylated β-CDs cannot be ruled out.

Figure 22:
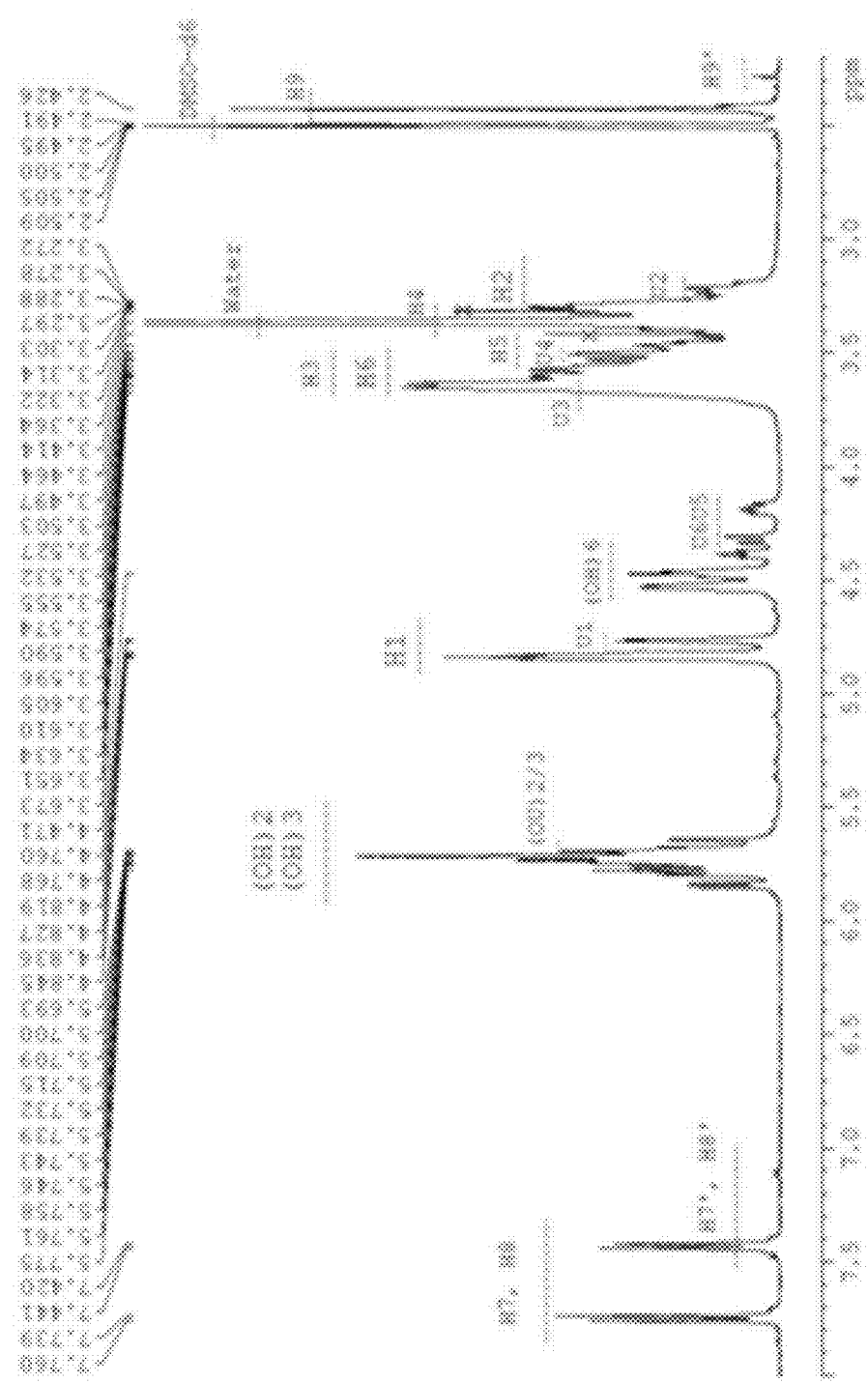
FIG. 22 is a $^1$H NMR spectrum of Ts-β-CDs.

FIG. 22 shows the 1H NMR spectrum of the Ts-β-CDs. All the β-CD regions compared with the native β-CD spectrum in FIG. 10 become more complicated due to the multiple possibilities for the tosylated positions in the β-CD and the probabilities of each position being tosylated. All the proton regions have been assigned in the spectrum according to the analyses of the COSY, ROESY and HMQC NMR spectra in comparison with those of the β-CD (discussed in detail in "Syntheses and Structural and Property Characterizations of Pegylated Beta-Cyclodextrins for Drug Delivery Applications," Masters of Science thesis submitted by Kim Trang Huu Nguyen, California State University, Los Angeles, 2015, the relevant portion[s] of which are incorporated herein by reference). The labeled numbers are given following the numbered positions of the Ts-β-CD as shown in FIG. 21.

As shown in FIG. 22, in the Ts region of the proton spectrum, the AB quartet with the peaks labeled at 7.760 ppm, 7.739 ppm, 7.441 ppm and 7.420 ppm, arise from the protons of the aromatic ring at positions 7 and 8, respectively, while the peak at 2.426 ppm arises from the methyl group 9. Compared with the 1H NMR spectrum of the intact TsCl, these proton peaks have higher chemical shifts, showing the deshielding effect relative to the native TsCl. The increased chemical shifts indicate that the chlorine atom in TsCl was replaced by the more electronegative oxygen atom, proving the formation of Ts-β-CD. There is remaining native TsCl mixed in the Ts-β-CD product, as detected with the minor peaks at resonance frequencies at 7.479 ppm/7.459 ppm and 7.120 ppm/7.100 ppm for the aromatic 7 and 8 protons (labeled as H7' and H8'), respectively, and at 2.284 ppm for the methyl 9 proton (labeled as H9'). The amount of the remaining native TsCl is estimated to be between 2.5% and 3.0%, according to the analysis of the integrated areas of the peaks.

Figure 23A:
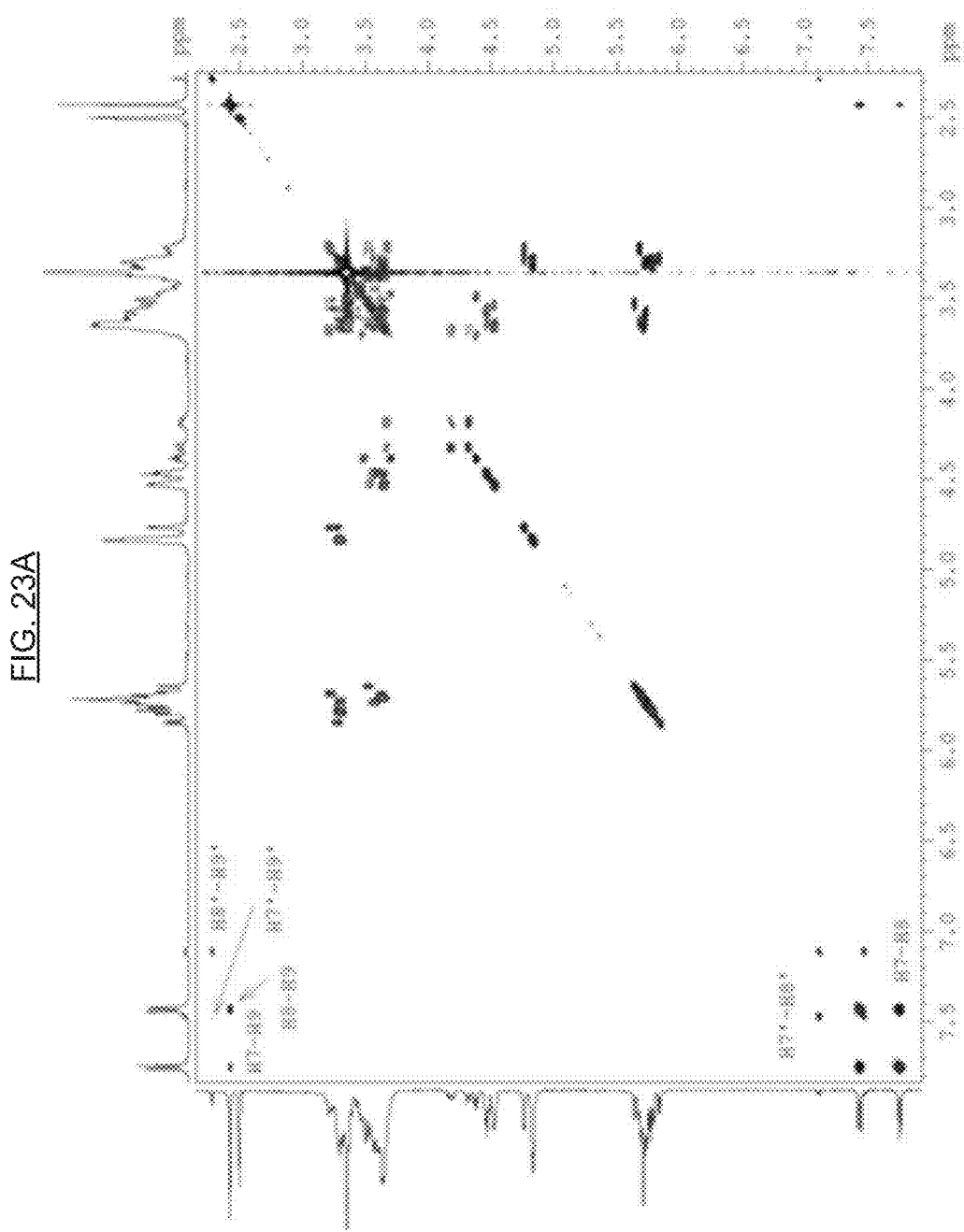
FIG. 23A is a COSY spectrum of the Ts-β-CDs.

As determined from the spectrum in FIG. 22, there is a small amount of unreacted CD species in the reaction product. The peaks of unreacted β-CD are labeled as (OU) 2/3, U1, U6, U5, U3, U4 and U2 from left to right. As were found in the COSY and ROESY spectra of FIGS. 23A-B, these peaks generally correlate only among themselves, and not with the already identified Ts-β-CD peaks. However, the U6 and U5 peaks also correlate with the Ts-β-CD H7 peak in the ROESY spectrum (FIG. 23B). Thus, the U6 and U5 peaks may be from a tosylated β-CD product (e.g., an isomer) that is structurally different from the other tosylated β-CDs, but which may have chemical shifts about the same as unreacted β-CD.

FIG. 23A shows the COSY spectrum of the Ts-β-CD products. As labeled in the spectrum, the pairs of correlations for the Ts region are H7-H8, H7-H9 and H8-H9. Correlations of these peaks with the β-CD peaks do not appear clearly due to their separation by the chain of chemical bonds, C—O—S—C—C. The pairs of correlations for the remaining free TsCl are labeled as H7'-H8', H7'-H9' and H8'-H9'.

FIG. 23B shows the correlations among the U peaks (e.g., the U region between 3.0 and 6.0 ppm). As labeled with the red squares to indicate the cross-peaks, (OU)2/3, U1, U3 and U4 correlate with U2; U6 with U5; U6 and U5 with U3; and U3 with U4. According to the proton regions of the β-CD, it is believed that OU2/3=(OH)2/(OH)3, U1=H1, U3=H3, U4=H4, U2=H2, U6=H6 and U5=H5 of unreacted β-CD. The peaks of this species do not correlate with the other Jβ-CD peaks.

Figure 23C:
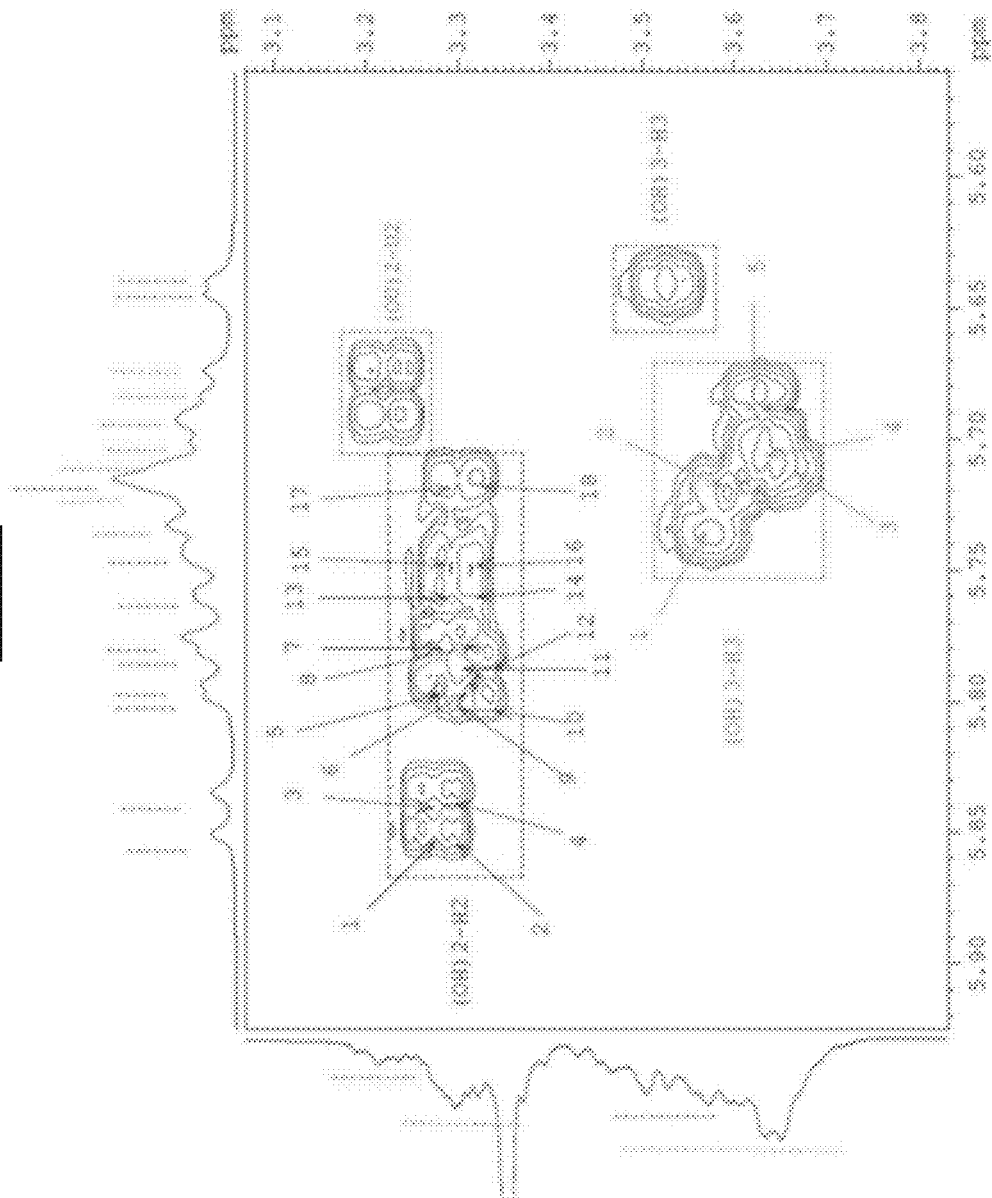
FIG. 23C shows the COSY correlations among the (OH) 2-H2 region and among the (OH)3-H3 region in the spectrum of FIG. 23A.
Figure 23D:
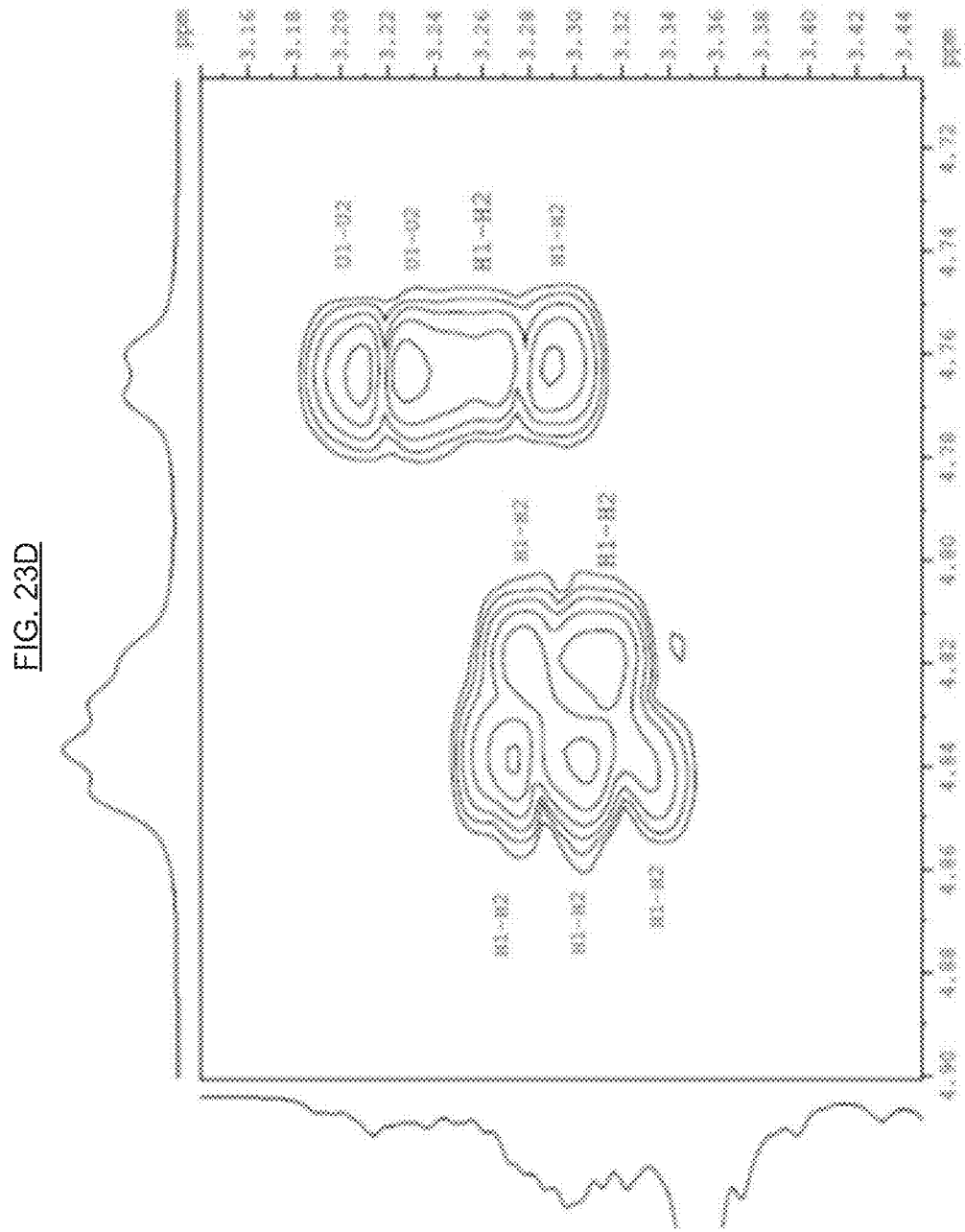
FIG. 23D shows the COSY correlation(s) among the H1-H2 region in the spectrum of FIG. 23A.
Figure 23E:
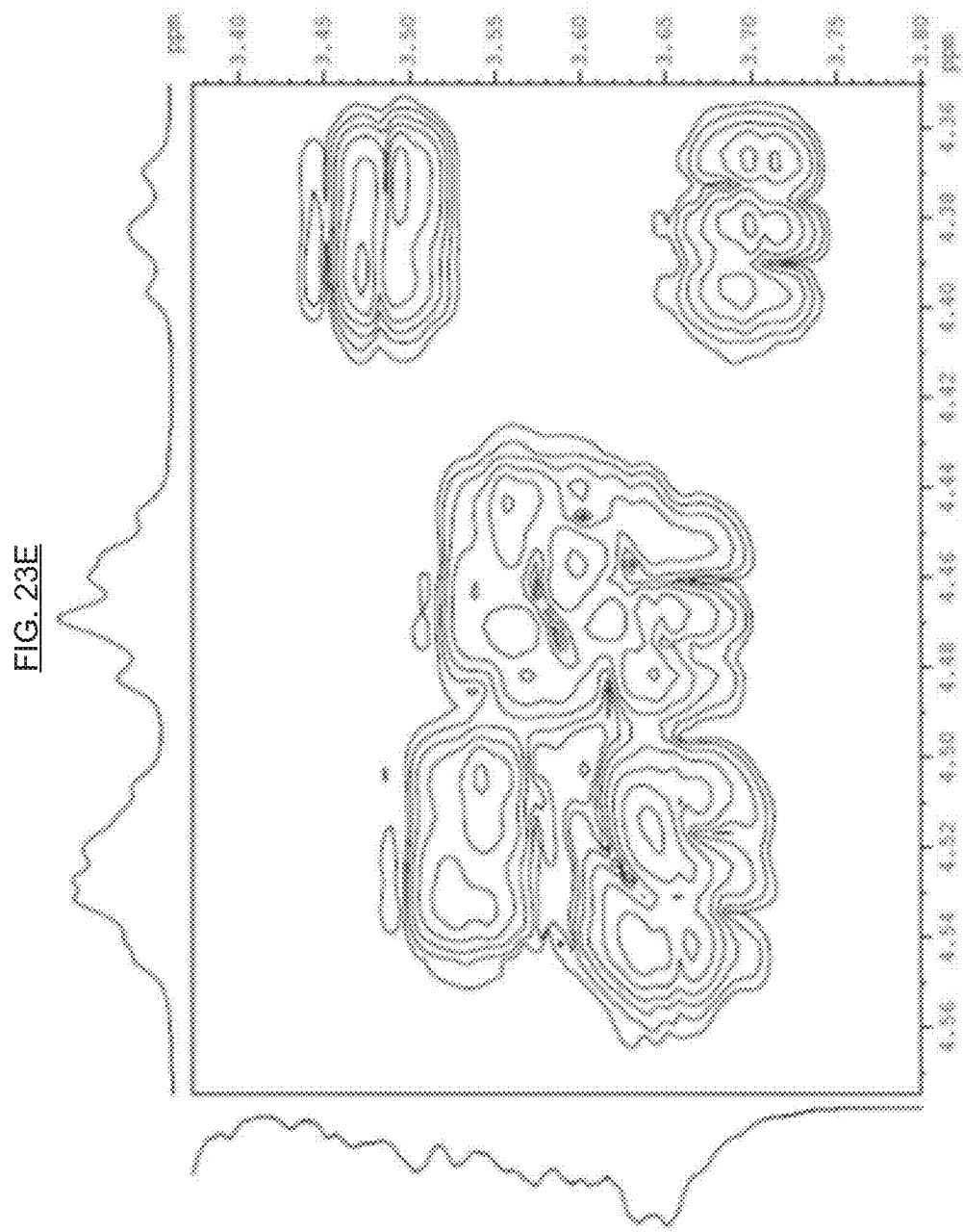
FIG. 23E shows the COSY correlation of in the (OH)6-H6 region in the spectrum of FIG. 23A.
Figure 23F:
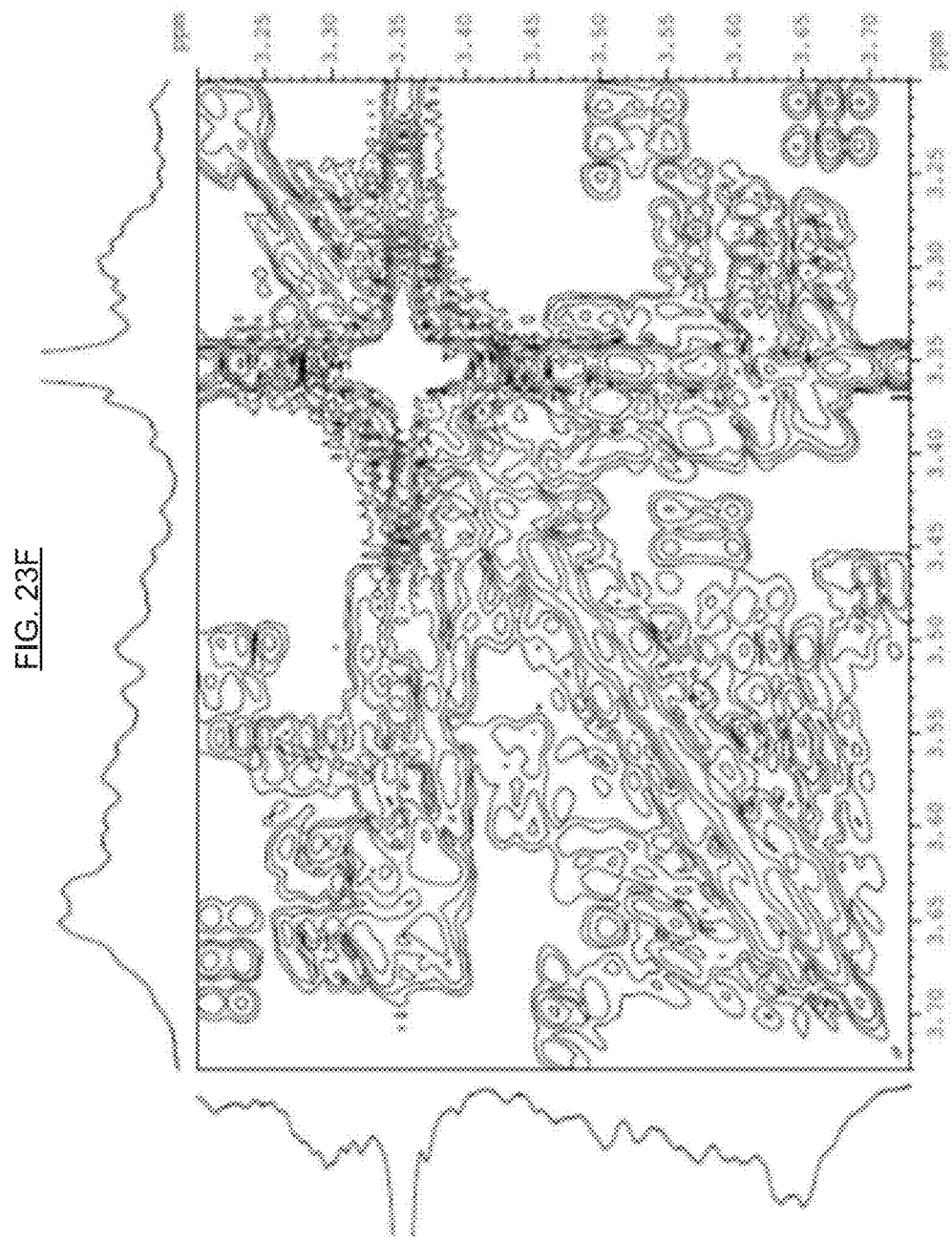
FIG. 23F shows the COSY correlation in the H6-H5-H4-H3-H2 region in the spectrum of FIG. 23A.

FIG. 23C shows the correlations among the (OH)2-H2 region and (OH)3-H3 region of Ts-β-CD. The numbers labeled with the peaks show the peaks from different possible isomers. FIG. 23D shows the correlations among the peaks in the H1-H2 region. FIG. 23E shows the correlations among the peaks in the (OH)6-H6 region. FIG. 23F shows the correlations among the peaks in the H6-H5-H4-H3-H2 region. The complex spectral patterns in FIGS. 23A-F demonstrate that there are several Ts-β-CD isomers in the intermediate product(s).

Figure 24A:
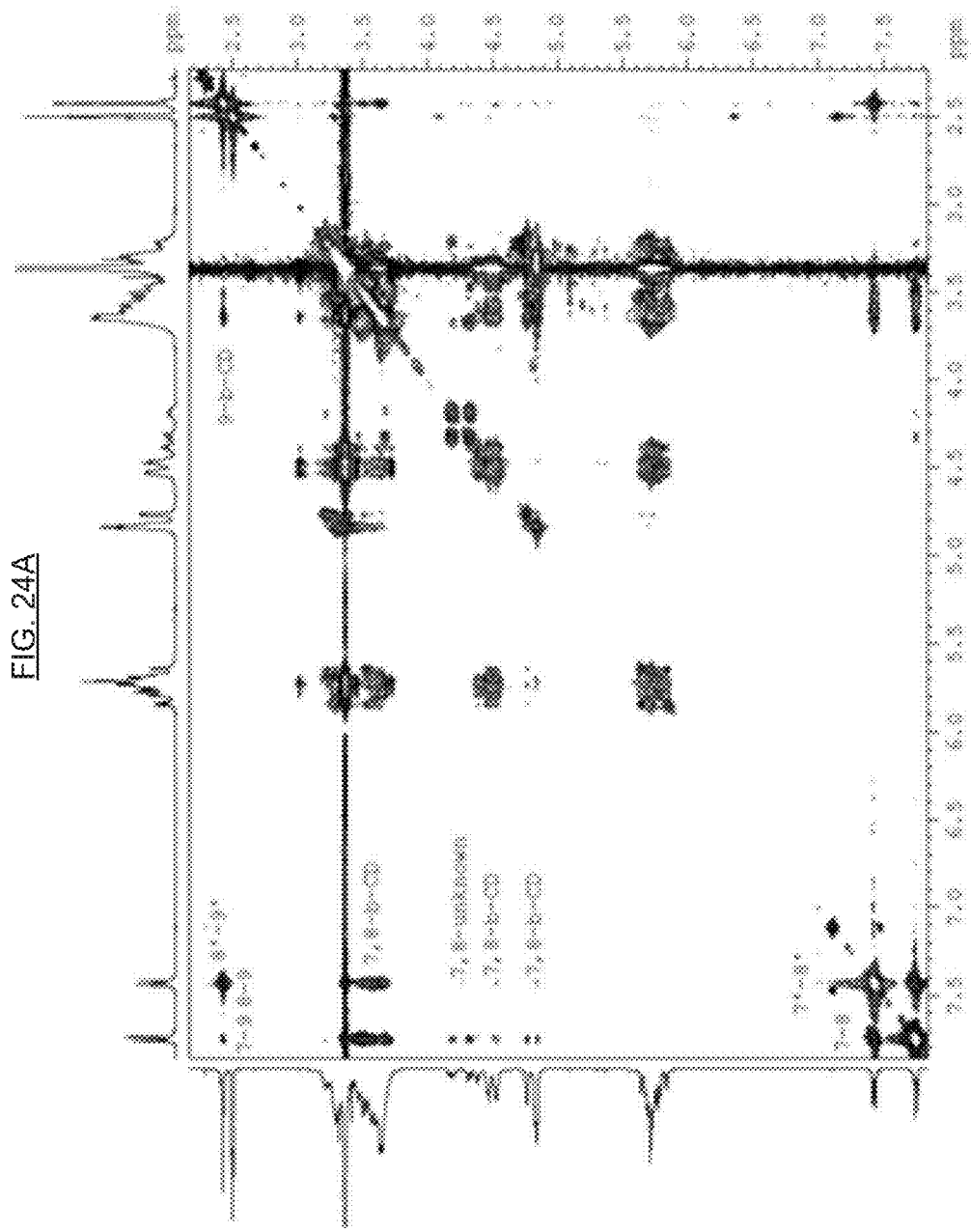
FIG. 24A is a full ROESY spectrum of a Ts-β-CD.
Figure 24B:
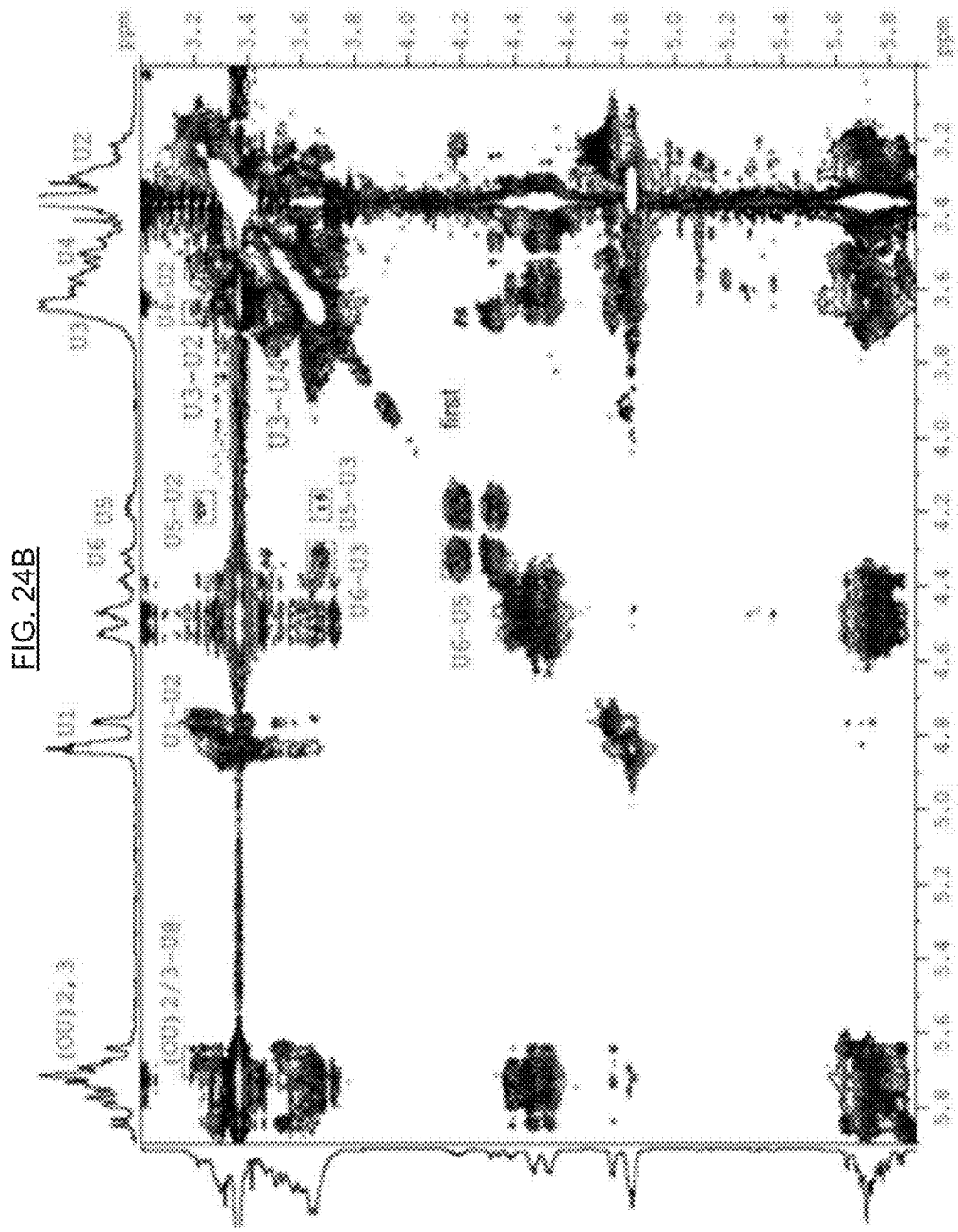
FIG. 24B shows the U species region of the ROESY spectrum of FIG. 24A.

FIG. 24A shows the full ROESY spectrum of the Ts-β-CDs in DMSO-$d_6$. As labeled in the spectrum, protons 7, 8 and 9 correlate to each other, demonstrating that these protons belong to the Ts group. The correlation of protons 8 and 9 is stronger than that of protons 7 and 9, consistent with the closer distance over space between protons 8 and 9 than between protons 7 and 9. These peaks also correlate to the β-CD peaks. They also correlate to the U peaks, showing that this species is tosylated (FIG. 24B). However, the U peaks do not correlate with the other β-CD peaks, which indicates that the unknown species is a separate Ts-β-CD product. The remaining free TsCl peaks labeled as 7', 8' and 9' correlate with each other, but not with the β-CD peaks.

Figure 24C:
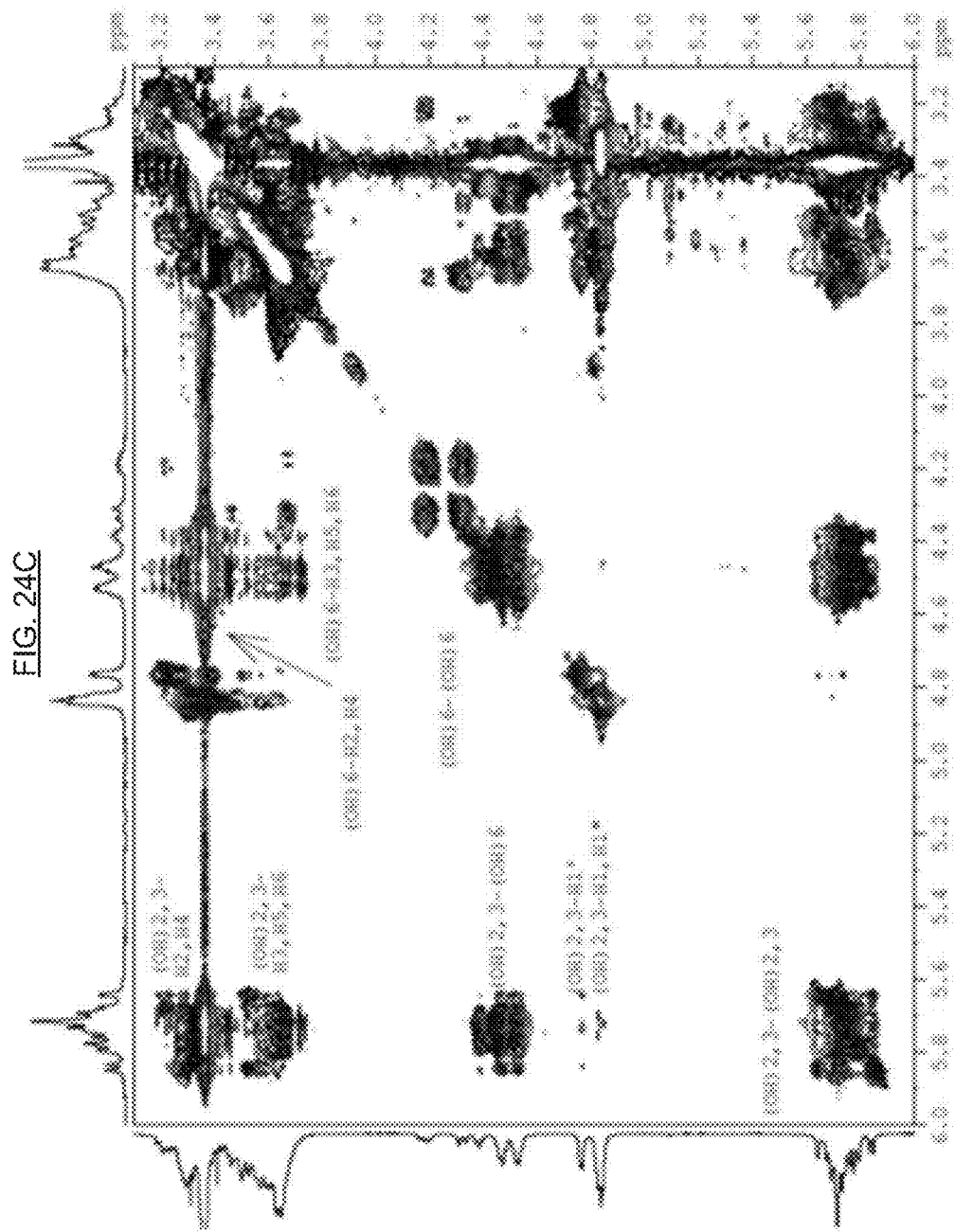
FIG. 24C shows correlations of the (OH) signals to other β-CD signals in the ROESY spectrum of FIG. 24A.
Figure 24E:
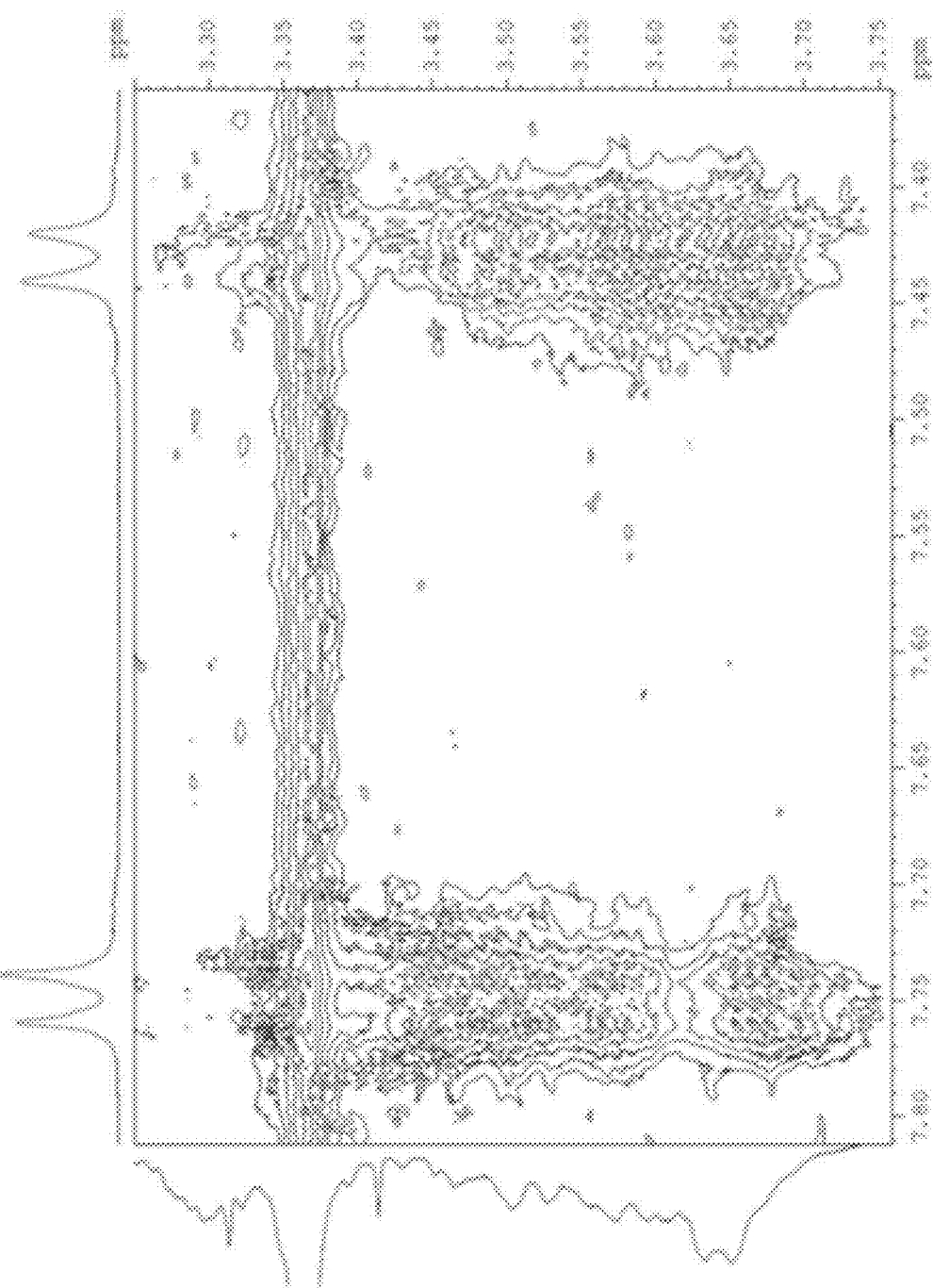
FIG. 24E shows correlations of the Ts protons with those of the H2 to H6 protons in the ROESY spectrum of FIG. 24A.
Figure 24F:
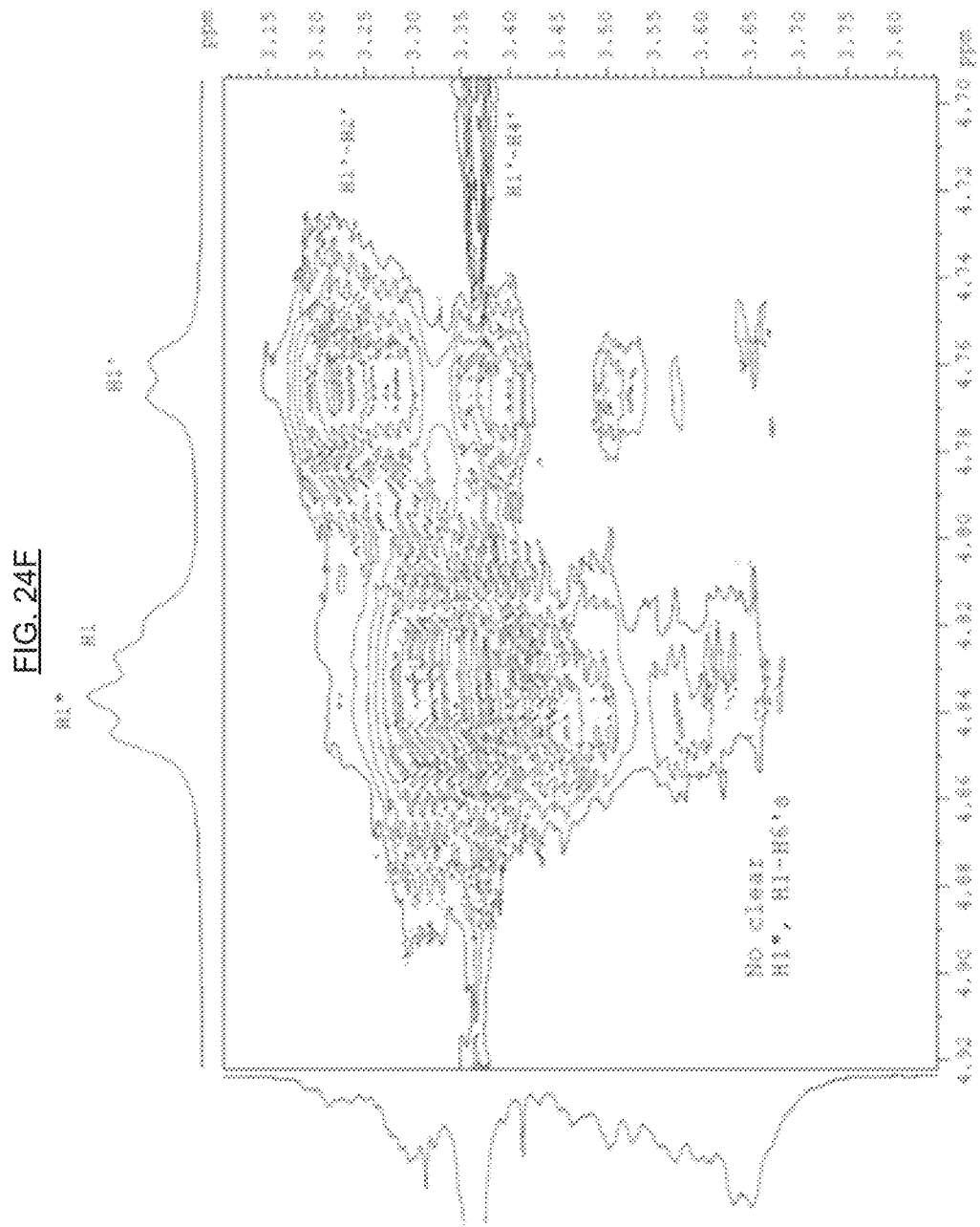
FIG. 24F shows correlations of H1 protons with all the other β-CD protons in the ROESY spectrum of FIG. 24A.
Figure 24G:
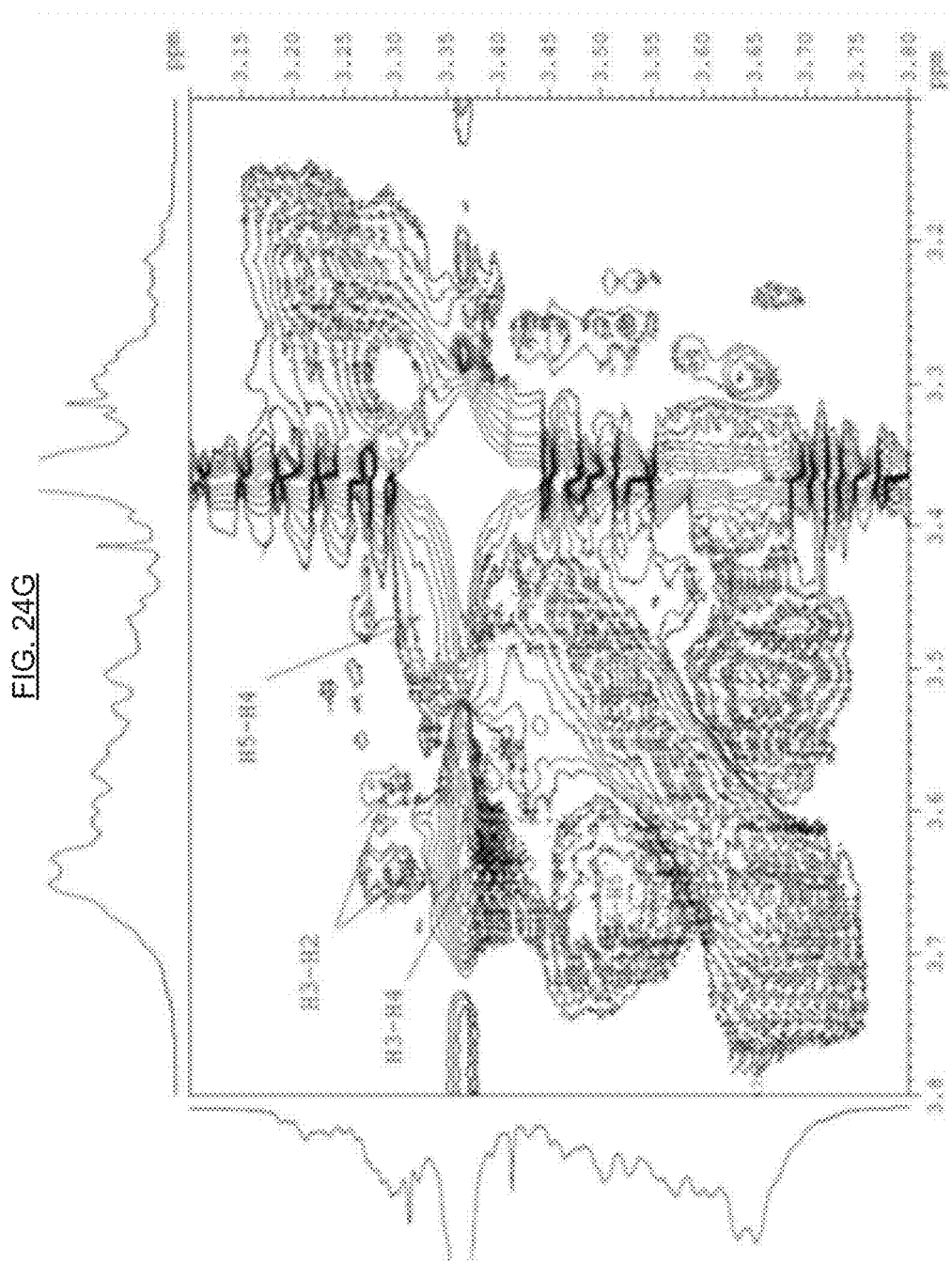
FIG. 24G shows correlations in among the H2, H3, H4, H5 and H6 protons the ROESY spectrum of FIG. 24A.

FIG. 24B shows the U region of the ROESY spectrum between 3.0 and 6.0 ppm along both axes. As is labeled in the spectrum, the U peaks correlate with each other, in addition to the Ts protons 7 and 8 as mentioned above. However, they do not correlate to any of the other β-CD peaks. Basically, the ROESY spectrum of FIG. 24B provides information similar to that shown in the COSY spectrum in FIG. 23B. FIG. 24C shows the correlation of the (OH) signals with other β-CD signals. FIG. 24D shows the correlation of the protons 7 and 8 with those of the H1 protons. FIG. 24E shows the correlation of the Ts protons with those of the H2 to H6 protons. FIG. 24F shows the correlation of H1 protons with all the other β-CD protons. FIG. 24G shows the correlations among the H2, H3, H4, H5 and H6 protons. The analyses of the NMR spectra indicate that Ts-β-CDs have been produced.

MALDI TOF Characterization of Ts-β-CDs

Figure 25:
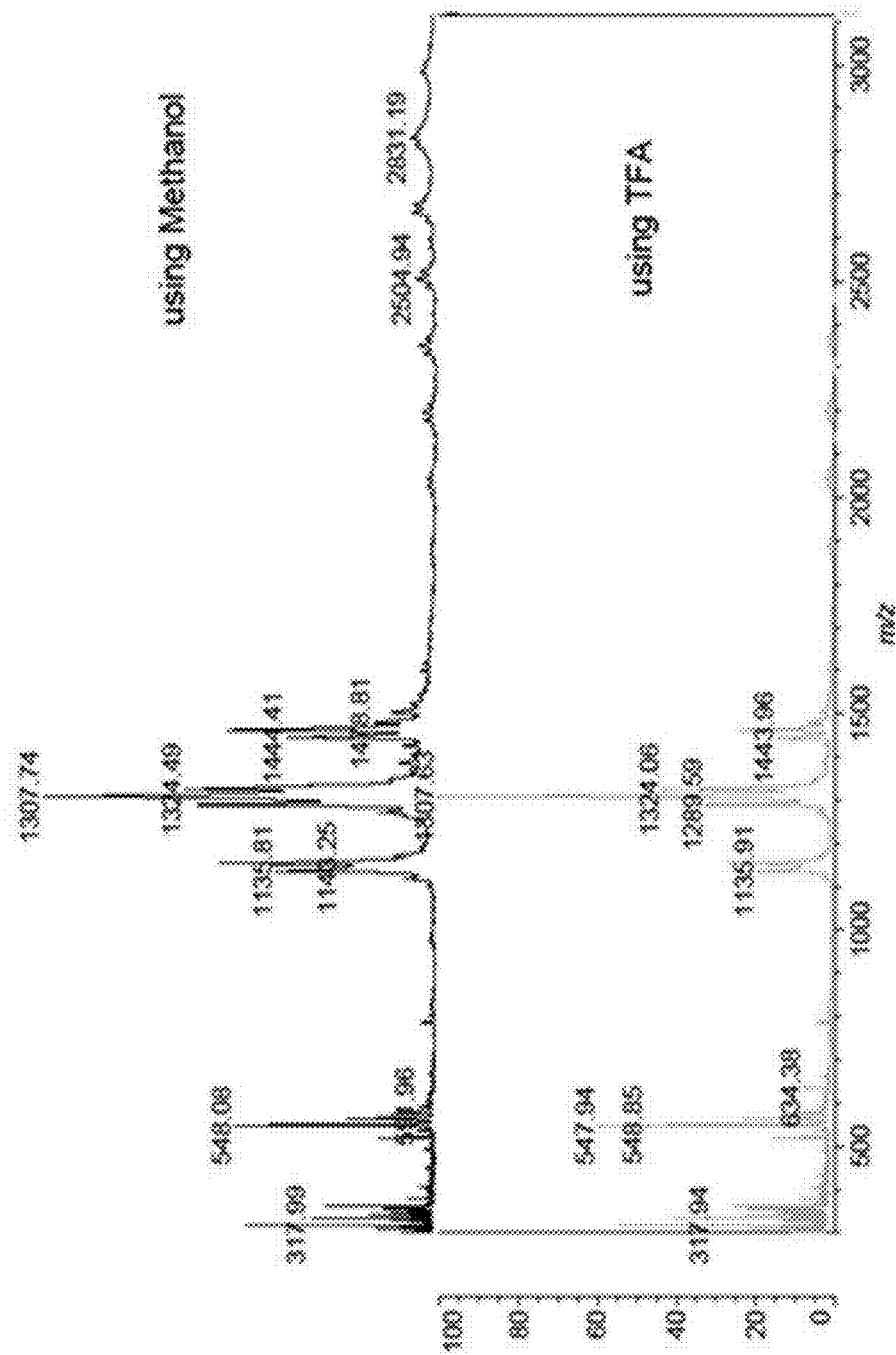
FIG. 25 shows Maldi TOF mass spectra of a Ts-β-CD.

The MALDI TOF mass spectra (FIG. 25) of the Ts-β-CDs show mixed products. The samples were dissolved in methanol (top) and trifluoroacetic acid (bottom). Two molecular weights are seen around 1289 Da and 1443 Da, indicating mono-tosylated β-CDs and di-tosylated β-CDs, respectively. The peak of mono-Ts-β-CDs (average mass of 1289.59) in the MALDI TOF has a higher intensity in comparison with the di-Ts-β-CDs (average mass of 1443.96). The ratio of mass between the mono-Ts-β-CD and the di-Ts-β-CD is about 1.33:1. The Ts groups may be attached to (OH)6 at the narrow opening or (OH)2 and (OH)3 at the wider opening of the β-CD structure.

NMR Characterizations of MPEG-β-CDs Synthesized from Tosylated β-CD

Figure 26:
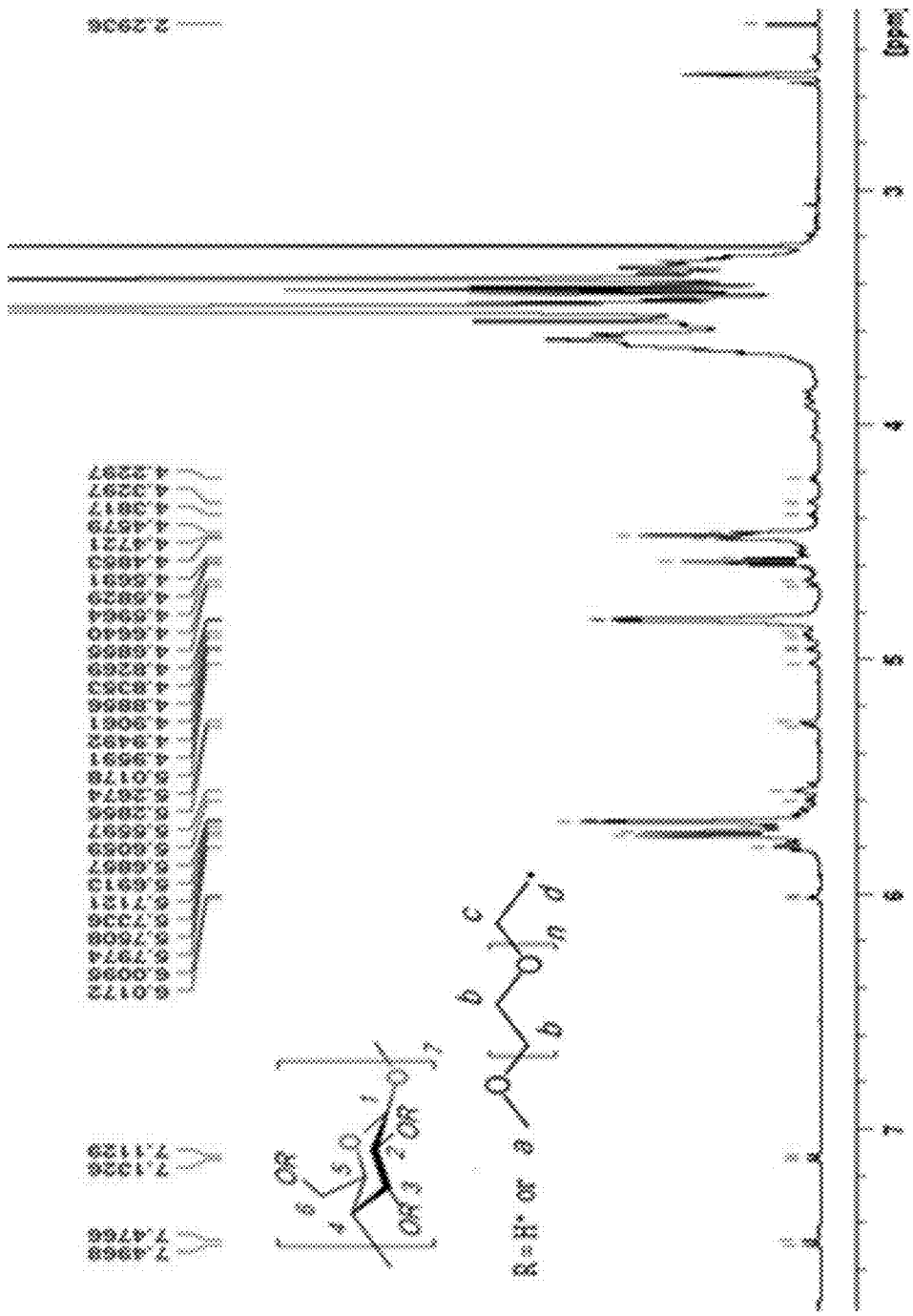
FIG. 26 is a $^1$H NMR spectrum of a MPEG350-β-CD product in DMSO-$d_6$.
Figure 27:
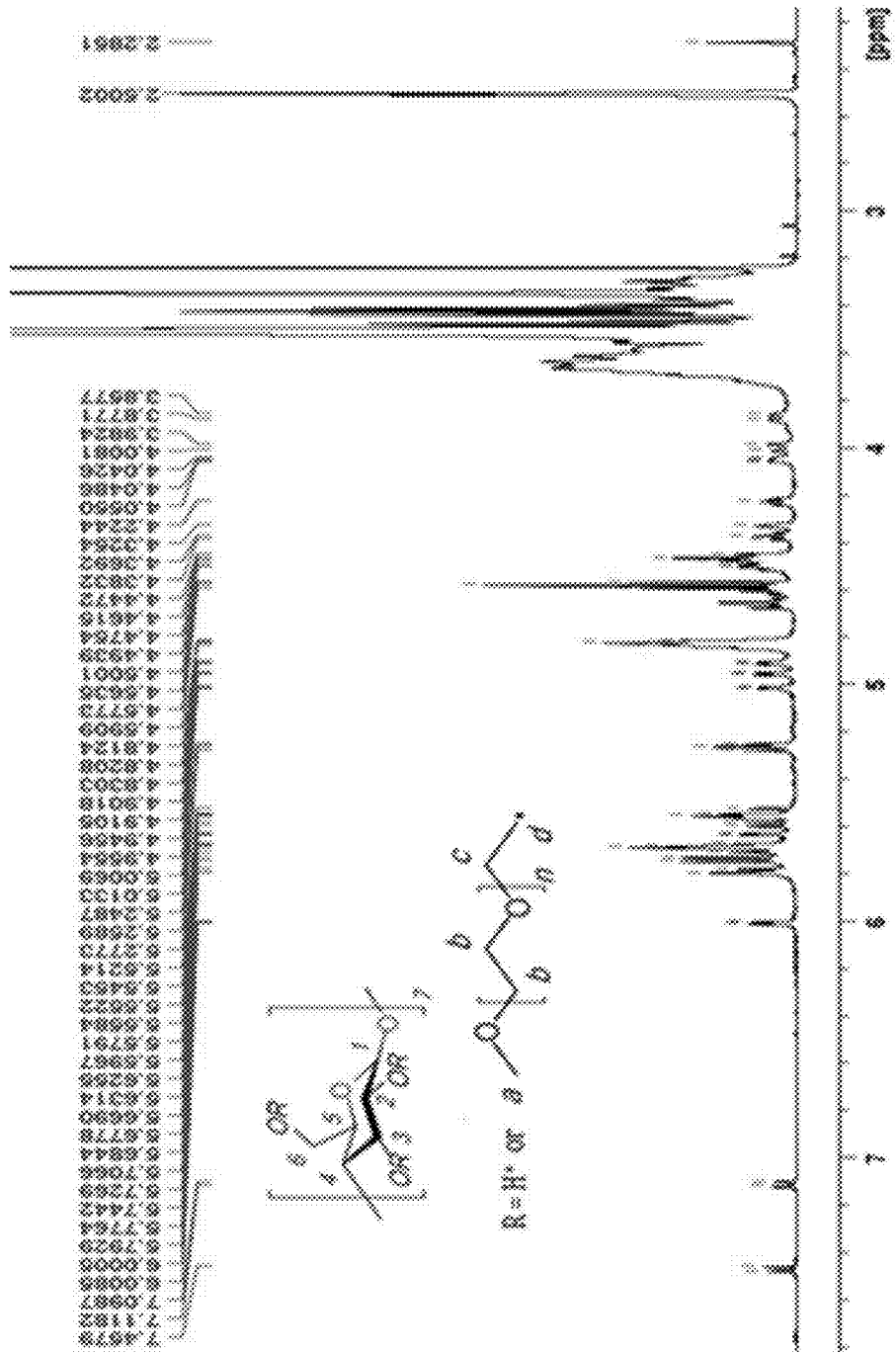
FIG. 27 is a $^1$H NMR spectrum of a MPEG550-β-CD product in DMSO-$d_6$.
Figure 28:
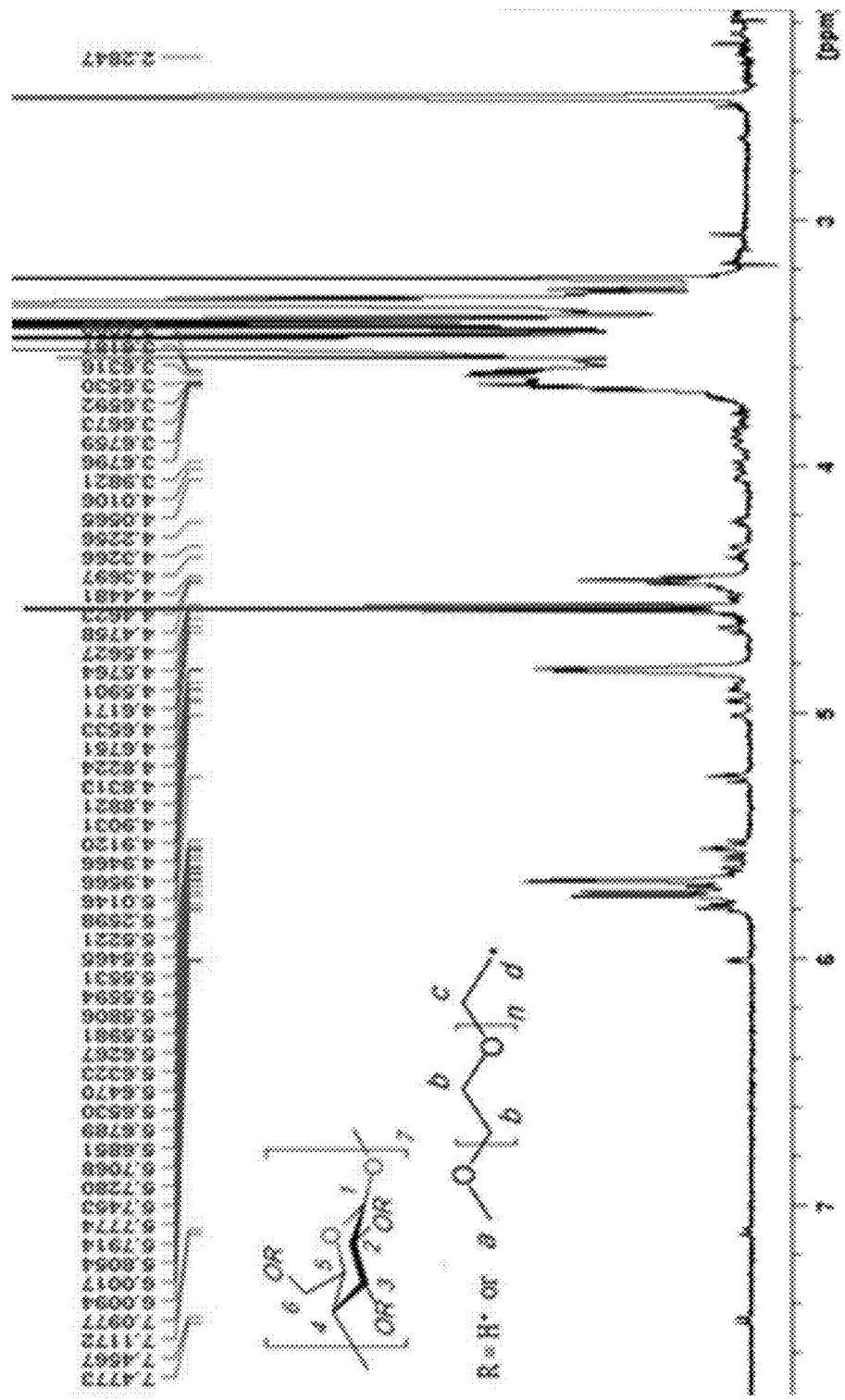
FIG. 28 is a $^1$H NMR spectrum of a MPEG750-β-CD product in DMSO-$d_6$.

FIG. 26 shows the NMR spectrum of MPEG350-β-CD, FIG. 27 shows that of MPEG550-β-CD, and FIG. 28 shows that of MPEG750-β-CD in DMSO-$d_6$. The $(CH_2)_n$ peaks in FIGS. 31-33 were truncated to enlarge the other signals. The weakly coupled AB quartets at 7.7598 ppm, 7.7390 ppm, 7.4408 ppm and 7.4204 ppm of the aryl protons in Ts-β-CD (FIG. 22) largely disappeared. Instead, weak AB quartet peaks at 7.1326 ppm, 7.1129 ppm, 7.4968 ppm and 7.4766 ppm appear in the $^1$H NMR spectrum for MPEG350-β-CD (FIG. 26), at 7.1192 ppm, 7.1097 ppm, 7.4790 ppm and 7.4579 ppm for MPEG550-β-CD (FIG. 27), and at 7.1172 ppm, 7.0977 ppm, 7.4773 ppm and 7.4566 ppm for MPEG750-β-CD (FIG. 28). Similarly, the Ts methyl group's chemical shift at 2.4266 ppm in Ts-β-CD was replaced by the weak peaks with chemical shifts at 2.2936 ppm, 2.2851 ppm and 2.2847 ppm for MPEG350-β-CD (FIG. 26), MPEG550-β-CD (FIG. 27), and MPEG750-β-CD (FIG. 28), respectively. These weak peaks may be from unreplaced or unreacted Ts groups from the Ts-β-CDs remaining in the MPEG-β-CD products.

Figure 29:
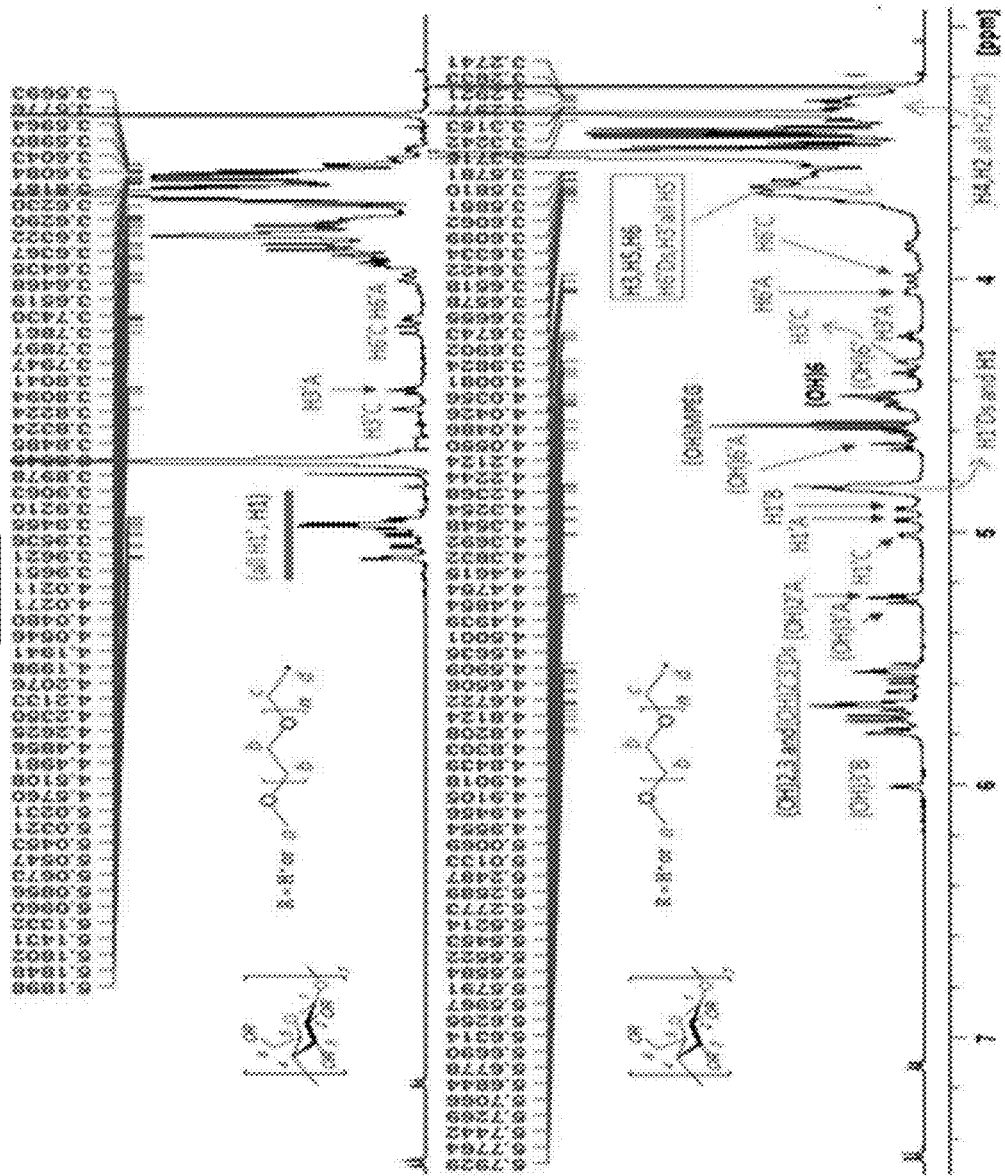
FIG. 29 is a comparison of the $^1$H NMR spectra of MPEG550-β-CD in $D_2O$ (top) and DMSO (bottom).

FIG. 29 shows a comparison of the $^1$H NMR spectra of MPEG550-β-CD dissolved in $D_2O$ (top) and in DMSO-$d_6$ (bottom). The $^1$H NMR spectra of the other MPEG-β-CD products look similar. The spectra in FIG. 29 show that MPEG550-β-CDs have an H1' NMR signal that is more deshielded than the H1 signal of the unmodified β-CD. In addition, there are new proton signals which appear around the signal regions of (OH)2, (OH)3, and (OH)6 in DMSO-$d_6$.

Figure 30:
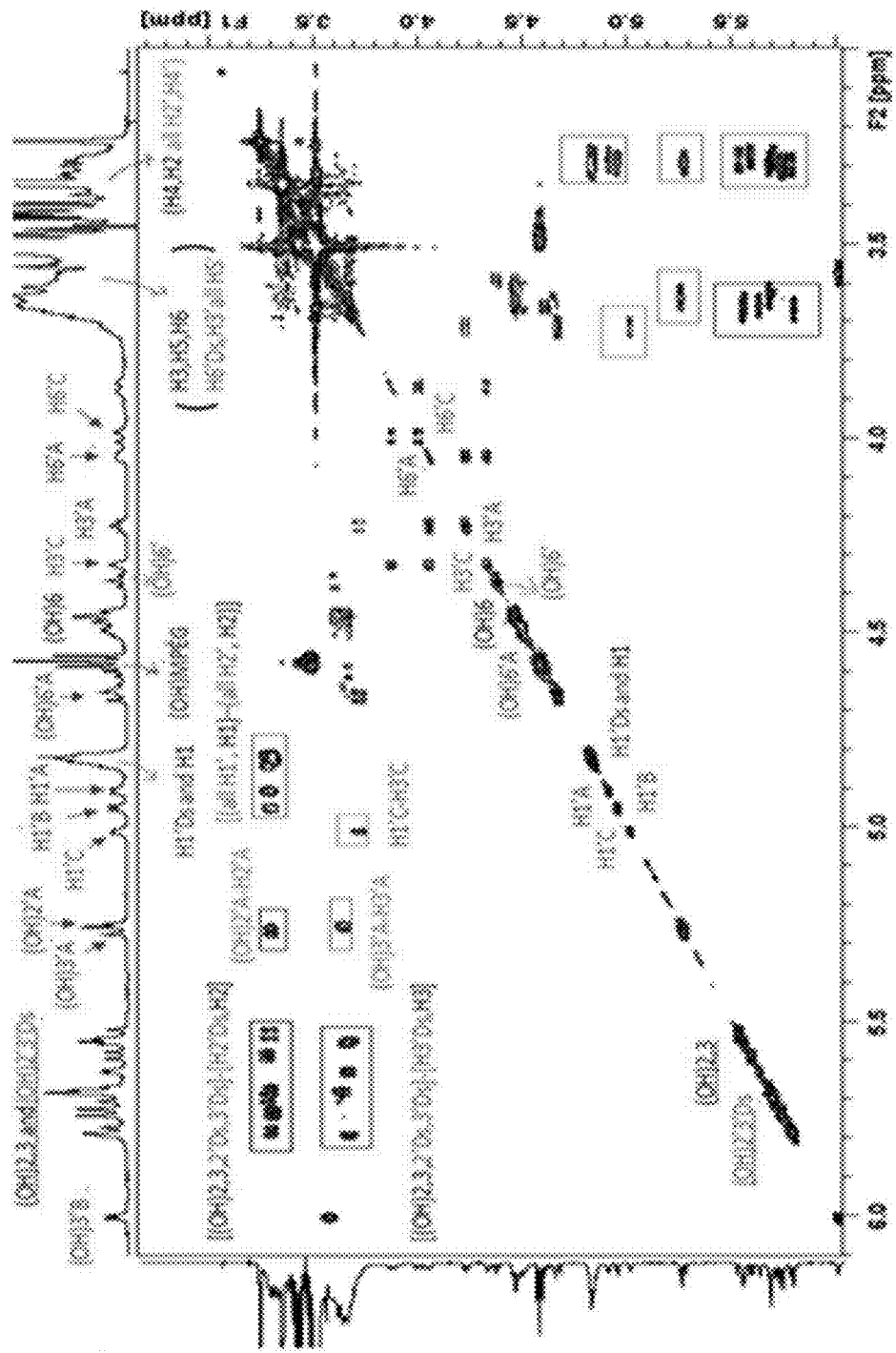
FIG. 30 is a COSY NMR spectra of MPEG550-β-CD in DMSO-$d_6$.
Figure 31:
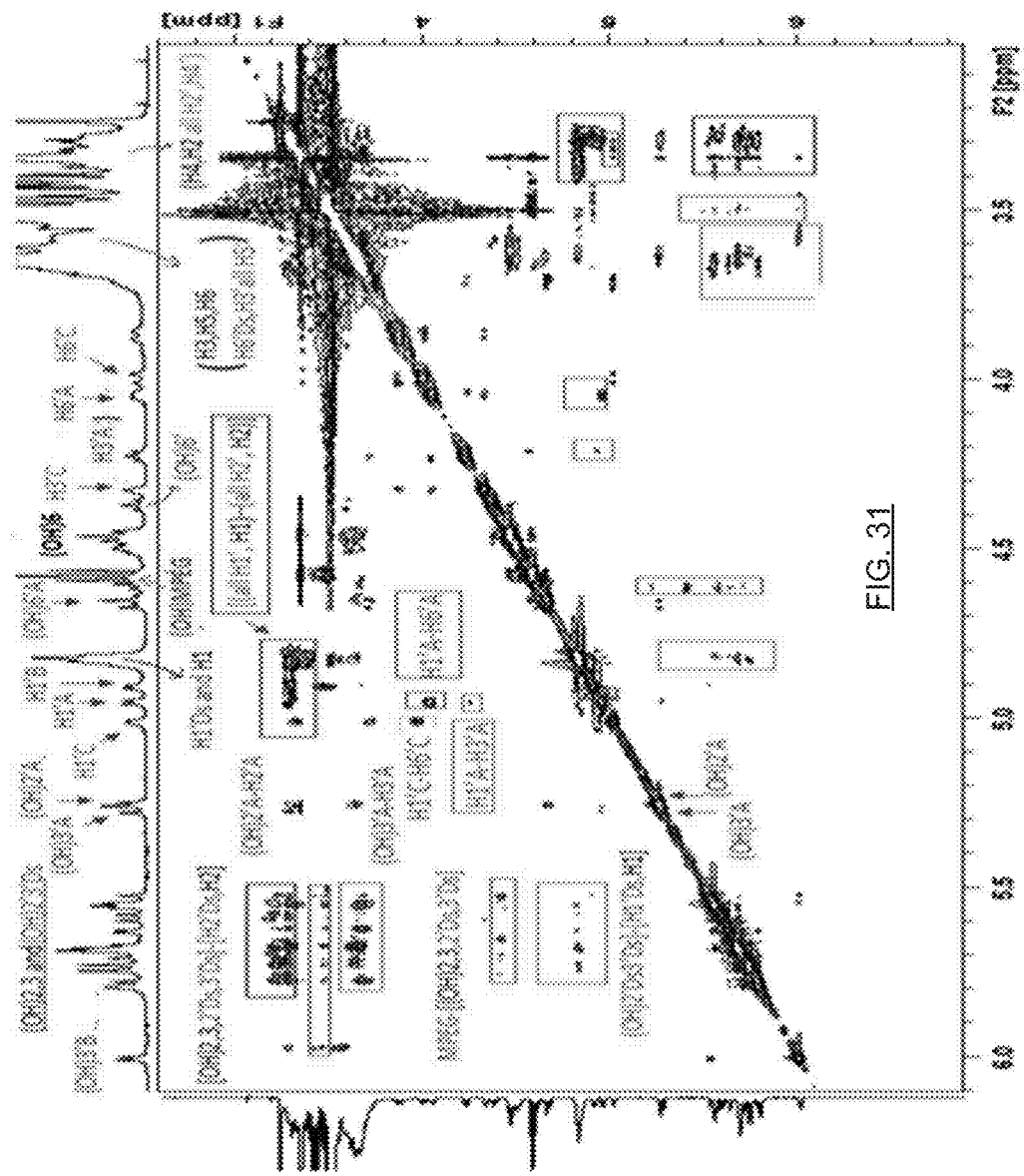
FIG. 31 is a ROESY NMR of MPEG550-β-CD in DMSO-$d_6$.

As discussed above, both mono-Ts-β-CD and di-Ts-β-CD were produced. Thus, the structures of MPEG-β-CDs synthesized from the Ts-β-CDs are also complex. The COSY and ROESY NMR spectra of MPEG550-β-CD dissolved in DMSO-d6 are shown in FIG. 30 and FIG. 31, respectively. There are many doublets appearing with chemical shifts gradually increasing from 4.8124 to 5.2773 ppm. These proton signals are referred to as H1'A, H1'B, and H1'C. These peaks are broad with chemical shifts at 4.8124 ppm, 4.8208 ppm, 4.8303 ppm and 4.8409 ppm. There is another H1' peak overlapping with the original H1, and this H1' peak is labeled as H1'D.

In the region of the (OH)2 and (OH)3 peaks, the two strongest doublets, with chemical shifts of 5.6811 ppm and 5.7753 ppm, are believed to be the (OH)3 and (OH)2 protons of the α-D(+)-glucopyranoside rings that are not attached to or replaced by a MPEG unit. However, these chemical shift values are slightly lower than the chemical shifts of the hydroxyl protons of (OH)3 and (OH)2 of the unmodified β-CD. There are several other doublets around these two doublets. These new doublets are referred to as (OH)2'D and (OH)3'D because they correlate with H1'D, as shown in FIG. 31.

As shown in FIG. 29, the hydroxyl proton of (OH)6 has a chemical shift of 4.4613 ppm. This proton is also shielded after the MPEG is attached to the β-CD. There is a triplet around 4.3691 ppm and a triplet-like signal at 4.999 ppm, which is labeled as (OH)6'A due to its correlation with H1'A, (OH)2'A and (OH)3'A. The triplet at 4.3691 ppm does not show any correlation with the major proton signals. Thus, it is believed to belong to a α-D(+)-glucopyranoside ring to which an MPEG unit is not attached.

The signals from 3.8295 ppm to 4.3254 ppm are believed to be the signals of H3'A, H3'C, H6'A, and H6'C because they have correlations with (OH)2'A, (OH)3'A, H1'A and H1'C. The signals with a chemical shift in the range from 3.5705 ppm to 3.6902 ppm appear to be the overlapping peaks of H3, H6, H5, H3'B and H3'D, and possibly also other H3', H6' and H5' peaks.

As mentioned above, the major Ts-β-CD products in the experiments described herein are mono-Ts-β-CD and di-Ts-β-CD. The favored positions for Ts bonding to β-CD are O6 and O2. As a result, a MPEG unit in the pegylated β-CDs should also be in these positions by replacing the Ts groups. If a MPEG unit is attached to O6, the electron withdrawing effect of the MPEG unit on H1 may not cause much change in the chemical shift of H1 because of the chemical bond separation. Because the H1'D peak or signal overlaps with H1 peak or signal, H1'D is the H1 proton in the α-D(+)-glucopyranoside ring attached to the MPEG unit at O6. Furthermore, there might be more than one H1' signal or peak in this area due to the wide correlations with all hydroxyl protons in the (OH)2 and (OH)3 region (e.g., from about 5.5 ppm to about 6.0 ppm). Because a MPEG chain is a slightly stronger electron withdrawing group than a hydroxyl group, the resonance of the hydroxyl protons is also affected by the neighboring bonded MPEG unit, shifting the resonances to higher chemical shifts. This influence is easily seen when O2 or O3 is attached to the MPEG unit. Therefore, (OH)3'B may be the result of a MPEG unit attached to O2. However, the chemical shifts of (OH)2'A and (OH)3'A become more challenging to identify because they are more shielded than (OH)2 and (OH)3 in free β-CD. This phenomenon may contradict the above explanation, but it may also be related to the chemical shifts of H3' and H6'. Since the H3'A and H6'A peaks have much greater chemical shifts than H3 and H6 in unmodified β-CD, the H3'D and H6'D signals must belong to an MPEG-β-CD that contains two MPEG chains. To some extent, more MPEG units attached to β-CD might be expected to cause the shielding effect on hydroxyl protons because a higher density of electron clouds may be around the oxygen atoms of the hydroxyl groups.

MALDI-TOF Characterizations of MPEG-β-CDs Synthesized from Tosylated β-CD

Figure 32:
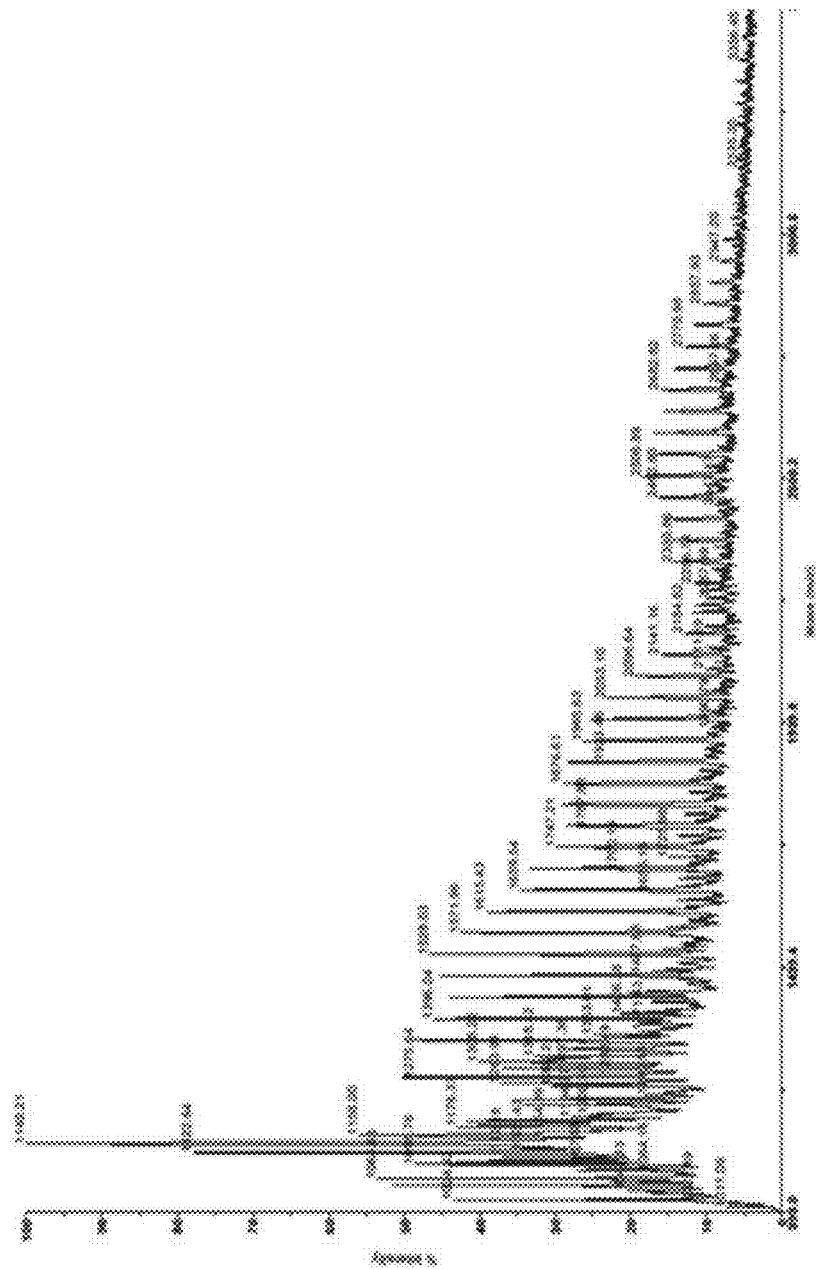
FIG. 32 is a MALDI-TOF mass spectrum of MPEG550-β-CD.

FIG. 32 shows the MALDI-TOF mass spectrum of the MPEG550-β-CD product mixture. DHB was used as the matrix, and 1 μL of the MPEG550-β-CD product sample in DHB was spotted on the sample plate and air dried. The MALDI-TOF mass spectrum of FIG. 32 shows that the product is a mixture of mono-MPEG550-β-CDs, di-MPEG550-β-CD and tri-MPEG550-β-CD. The results of the mass spectrum analysis are consistent with the COSY and ROSEY NMR analyses.

Figure 33:
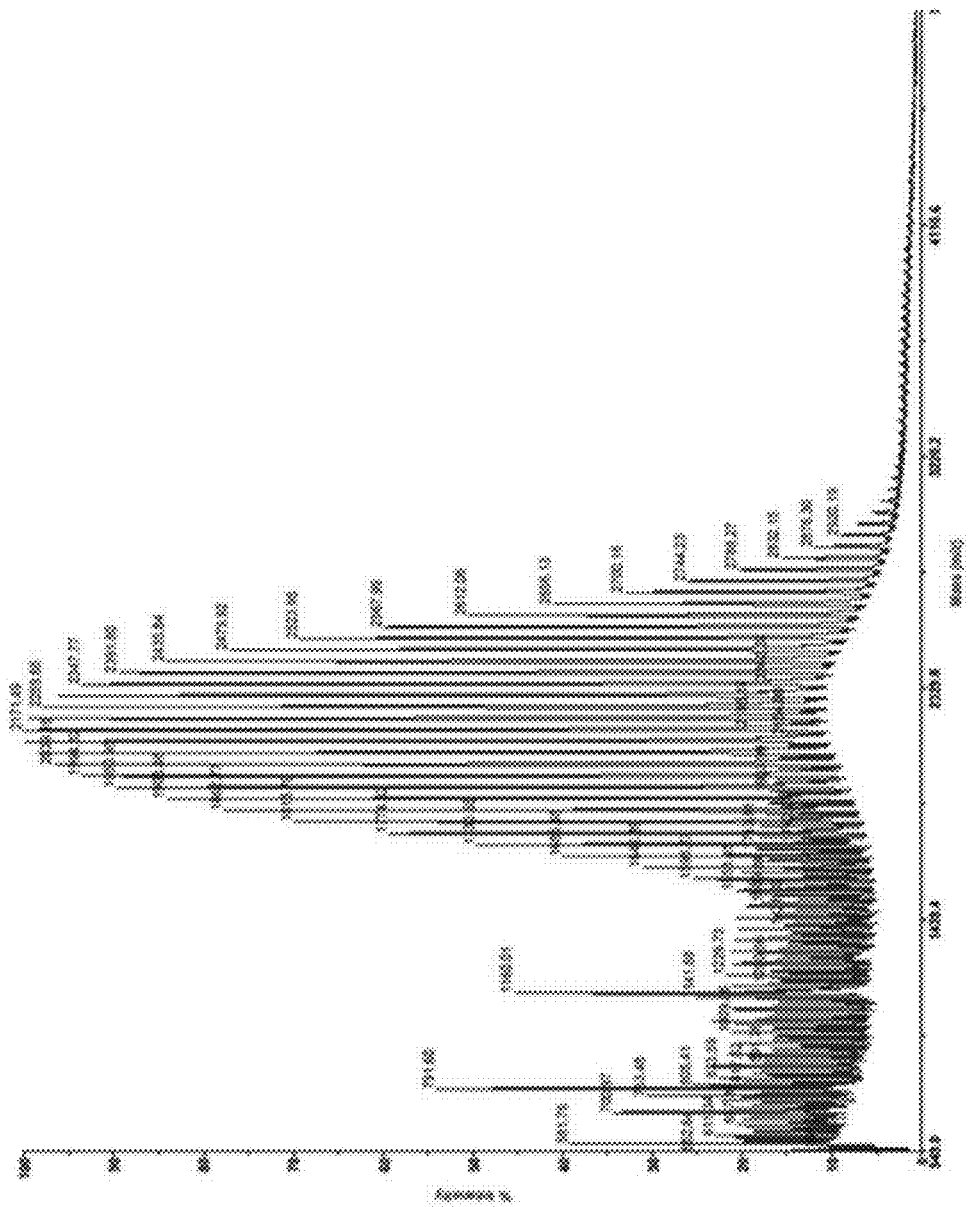
FIG. 33 is a MALDI-TOF mass spectrum of MPEG750-β-CD.

FIG. 33 shows the MALDI-TOF mass spectrum of the MPEG750-β-CD product mixture. DHB was used as a matrix in the MALDI TOF experiment. The MALDI-TOF mass spectrum of FIG. 33 shows the formation of the MPEG750-β-CD product.

Figure 34:
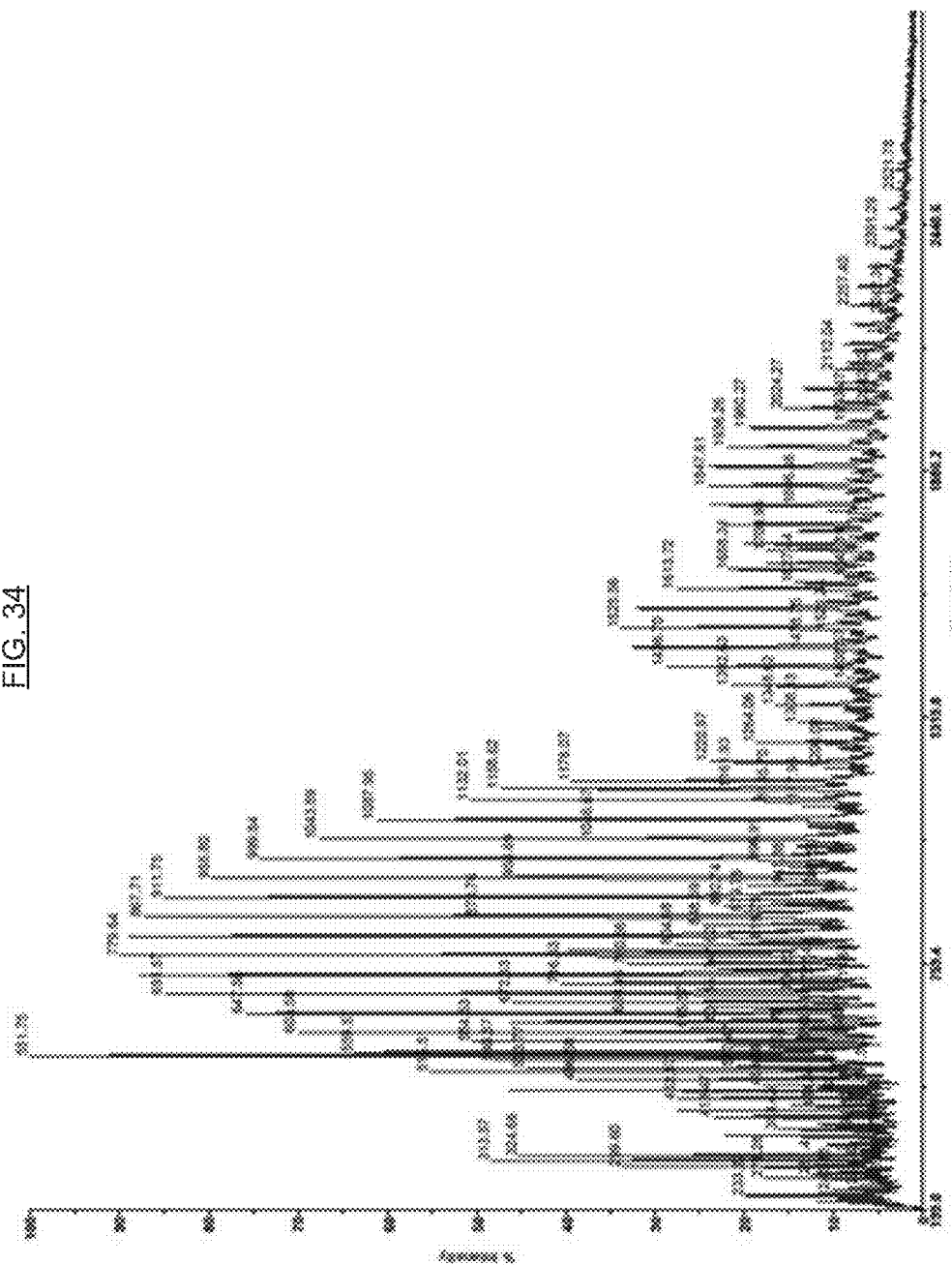
FIG. 34 is a MALDI-TOF mass spectrum of MPEG350-β-CD.

FIG. 34 shows the MALDI-TOF MS spectrum of the MPEG350-β-CD product mixture. DHB was used as the matrix. The spectral pattern in FIG. 34 indicates that the resulting product is a mixture of MPEG350-β-CDs having one or two MPEG units attached.

The syntheses of pegylated CDs from a corresponding Ts-CD is an alternative method to produce MPEG-CDs, in addition to the method starting from a tosylated MPEG. Although both methods result in pegylated β-CDs, the latter (starting from a tosylated MPEG) gave more uniformly pegylated products.

Water Solubility of MPEG-β-CDs

Table 7 and Table 8 show a comparison of the water solubilities of β-CD, MPEG and MPEG-β-CDs synthesized from Ts-MPEGs and from Ts-β-CD, respectively. All the MPEG-β-CD products are either instantly or quickly soluble in water. "Instantly soluble in water" means that all of the MPEG-β-CD solid powder dissolved right away when brought into contact with water. "Quickly soluble in water" means that all of the MPEG-β-CD solid powder completely dissolved in water within some seconds to about a minute after water was added to the powder. The test results show that all of the MPEG-β-CD products synthesized have solubilities greater than 650 mg/ml, which is much larger than that of β-CD (18.5 mg/ml). The data in Tables 7 and 8 show that β-CD governs the physical states of the MPEG-β-CDs, while the MPEGs determine the solubilities of the MPEG-β-CDs in water.

TABLE 7

Some physical properties of β-CD, MPEG and MPEG-β-CDs synthesized from Ts-MPEGs

|  | β-CD | MPEG350 | MPEG550 | MPEG750 | MPEG2000 |
| --- | --- | --- | --- | --- | --- |
| Molecular weight (g/mol) | 1135 | 350 | 550 | 750 | 2000 |
| Physical state | White solid | Clear liquid, sticky | Clear liquid, sticky | White paste | White flake |
| Solubility in water at 25° C. | 18.5 mg/mL | Soluble, no definite data is available | Soluble, no definite data is available | Soluble, no definite data is available | Soluble, no definite data is available |
|  | β-CD | MPEG350-β-CD | MPEG550-β-CD | MPEG750-β-CD | MPEG2000-β-CD |
| Molecular weight (g/mol) (theoretical value for mono-MPEG-β-CD) | 1135 | 1485 | 1685 | 1885 | 3135 |
| Physical state | White solid | White solid | White solid | White solid | White solid |
| Solubility in water at 25° C. | 18.5 mg/mL | Instantly soluble, >650 mg/ml | Instantly soluble, >650 mg/ml | Instantly soluble, >650 mg/ml | Quickly soluble, >650 mg/ml |

TABLE 8

Some physical properties of β-CD, MPEG and MPEG-β-CDs synthesized from Ts-β-CD

|  | β-CD | Ts-MPEG350 | Ts-MPEG550 | Ts-MPEG750 |
| --- | --- | --- | --- | --- |
| Average molecular weight (g/mol) | 1135 | 500 | 700 | 900 |
| Physical state | White solid | Clear liquid, sticky | Clear liquid, sticky | White paste |
| Solubility in water at 25° C. |  | Soluble, no definite data is available | Soluble, no definite data is available | Soluble, no definite data is available |
|  | β-CD | MPEG350-β-CD | MPEG550-β-CD | MPEG750-β-CD |
| Molecular weight (g/mol) (theoretical value for mono-MPEG-β-CD) | 1135 | 1485 | 1685 | 1885 |
| Physical state | White solid | White solid | White solid | White solid |
| Solubility in water at 25° C. (mg/ml) | 18.5 mg/mL | Instantly soluble >650 mg/ml | Instantly soluble >650 mg/ml | Instantly soluble >650 mg/ml |

Inclusion Properties of MPEG-β-CDs

The MPEG-CD entity can form an inclusion compound to deliver a drug to a biological system. Inclusion compounds deliver drugs by fully or partially encapsulating a drug in the cavity of the CD, thus carrying the drug through the biological system. The advantages of having drugs delivered by inclusion compounds include the following: the drug's stability may be increased, the drug's water solubility may be increased, and the drug's biocompatibility may be increased. The MPEG-CD entity is a good candidate to form an inclusion compound because of the following advantages, but which are not limited to the following: (1) MPEGs are well known as biocompatible polymers, and (2) MPEGs can avoid detection by the human immune system, prolonging blood circulation time, reducing nephrotoxicity, improving controlled drug-release and drug stability, and/or easing other possible toxic effects of CDs. As demonstrated herein, attachment of a MPEG unit to β-CD tremendously increased the solubility of β-CD and reduced molecular interactions of β-CD with biological molecules when used to deliver drugs through mucus (e.g., as a model for delivery through a mucus membrane, such as in drug formulations for oral delivery, pulmonary delivery, nasal or olfactory delivery, gastric delivery, vaginal delivery, etc.).

To test the delivery mechanism of an inclusion compounds containing MPEG-β-CD products, MPEG550-β-CD (made from tosylated MPEG550) was selected as an example or model to test delivery of the drug 1-fluoroadamantane (1-FA) in a MPEG550-β-CD complex. This inclusion compound is compared with the commercially available 2-hydroxypropyl-β-CD (2HP-β-CD).

Materials and Instruments 2-hydroxypropyl-β-CD (2-HP-β-CD, CAS #: 128446-35-5) and tetrahydrofuran (THF, CAS #: 109-99-9) were purchased from Sigma Aldrich. 1-Fluroroadamantane (1-FA, CAS number: 768-92-3) was supplied by TCI America. Deuterium oxide ($D_2O$, CAS #: 7789-20-0) was obtained from Cambridge Isotope Laboratories, Inc. The $^1H$ NMR and ROESY NMR spectra were acquired using a Bruker Avance™ II 400 MHz NMR spectrometer.

Model System to Study the Inclusion Properties of MPEG-β-CDs

1-Fluoroadamantane (1-FA) has an exact size to fit in the cavity of β-CD. If 1-FA forms inclusion compounds with MPEG-β-CDs, other drug molecules or sections of drug molecules that have the diameters, dimensions or volumes equal to or smaller than that of 1-FA will also be expected to form inclusion compounds with MPEG-β-CDs. Thus, 1-FA is useful as a model to prove that use of an ether linker to make MPEG-β-CDs preserves the inclusion properties of β-CD. Here, MPEG550-β-CD was used as an example or model.

1-Fluoroadamantane (1-FA) was dissolved in a water soluble organic solvent, THF (although other water soluble organic solvents may be used, such as DMSO). 2HP-β-CD (acting as the control) and MPEG550-β-CD were separately dissolved in deionized water. The 1-FA and the 2HP-β-CD or MPEG550-β-CD solutions were mixed together using a vortex device. The mixtures were then lyophilized to obtain the dried inclusion compounds (ICs). The molar ratio of 1-FA to 2HP-β-CD and MPEG550-β-CD is 1:1. The ICs were easily dissolved in water.

Figure 35:
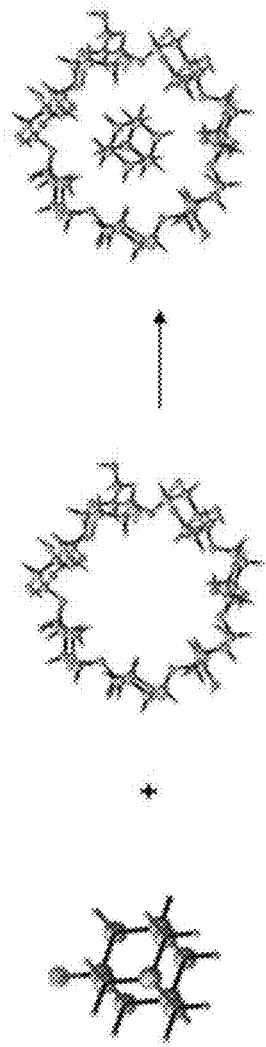
FIG. 35 shows the formation of complex between 1-FA and β-CD.

The scheme for the formation of an IC of 1-FA with β-CD (used as a model) is shown in FIG. 35. The 3D structure was made using the Gaussian 09 program. The optimized structures of 1-FA, β-CD and FA-β-CD were calculated using a semi-empirical MP3 method and/or software.

Results and Discussion

Figure 36:
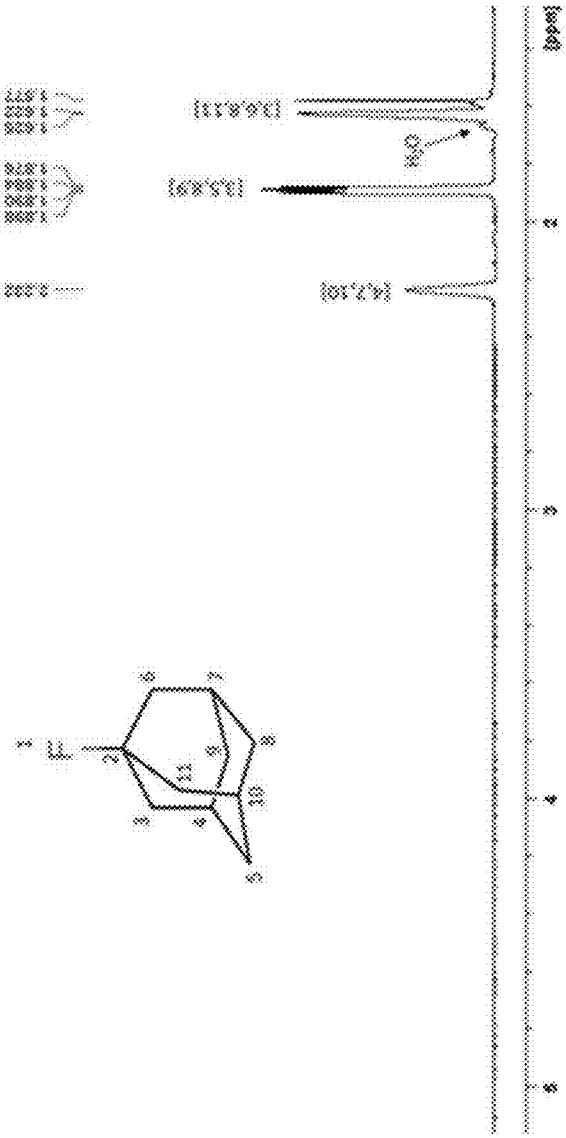
FIG. 36 is a $^1$H NMR spectrum of 1-FA dissolved in $CDCl_3$.
Figure 37:
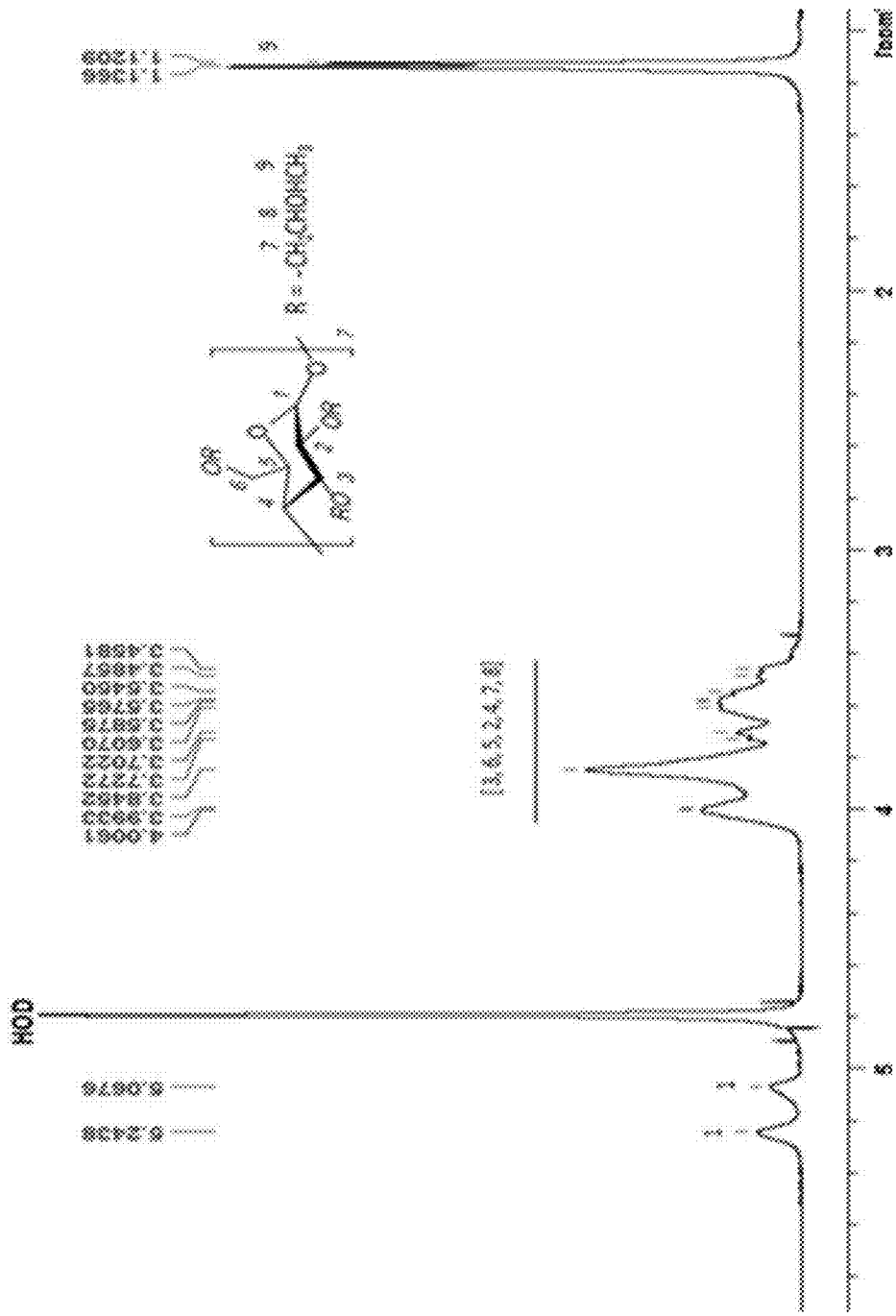
FIG. 37 is a $^1$H NMR spectrum of 2HP-β-CD dissolved in $D_2O$.
Figure 38:
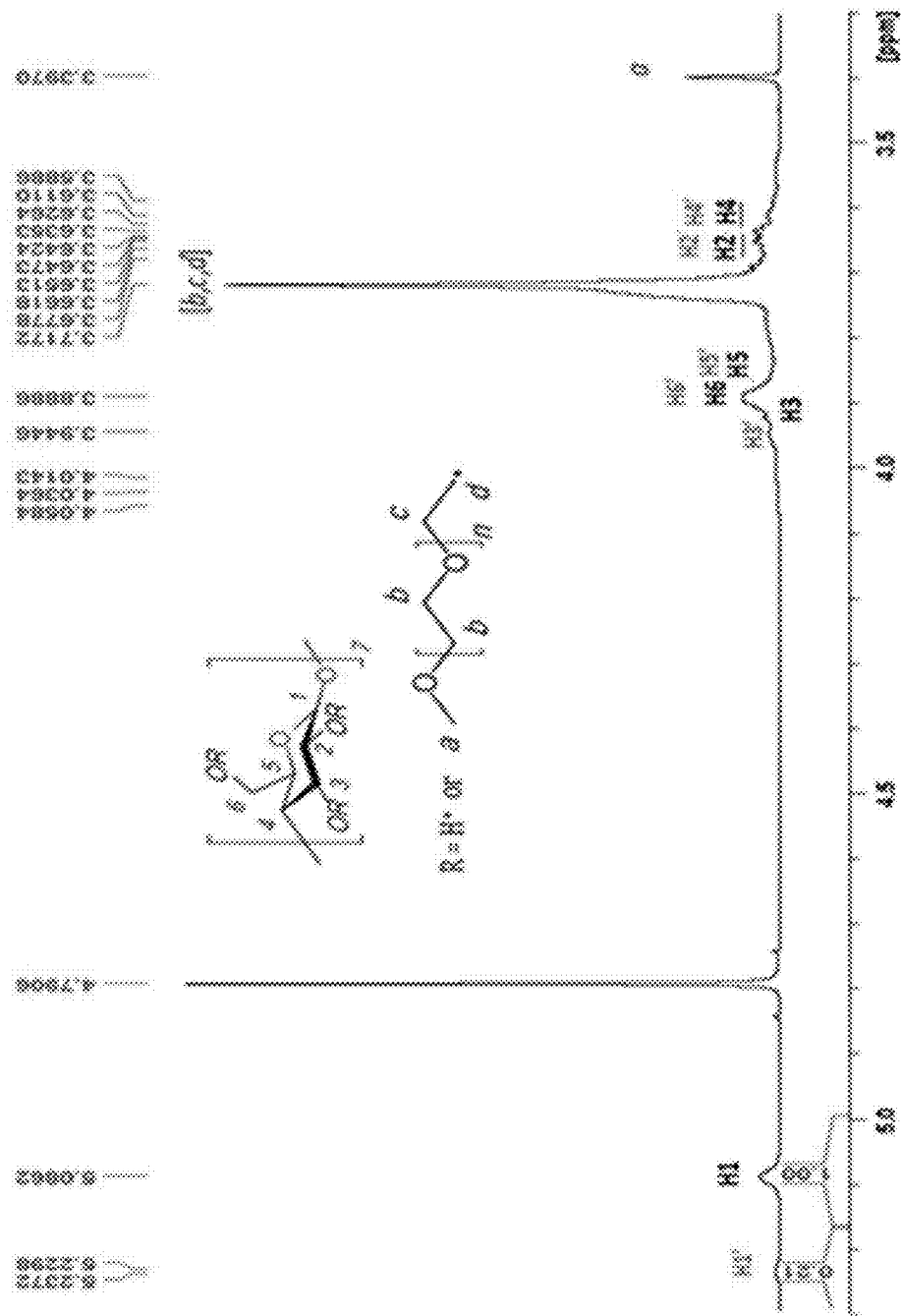
FIG. 38 is a $^1$H NMR spectrum of MPEG550-β-CD dissolved in $D_2O$.
Figure 39:
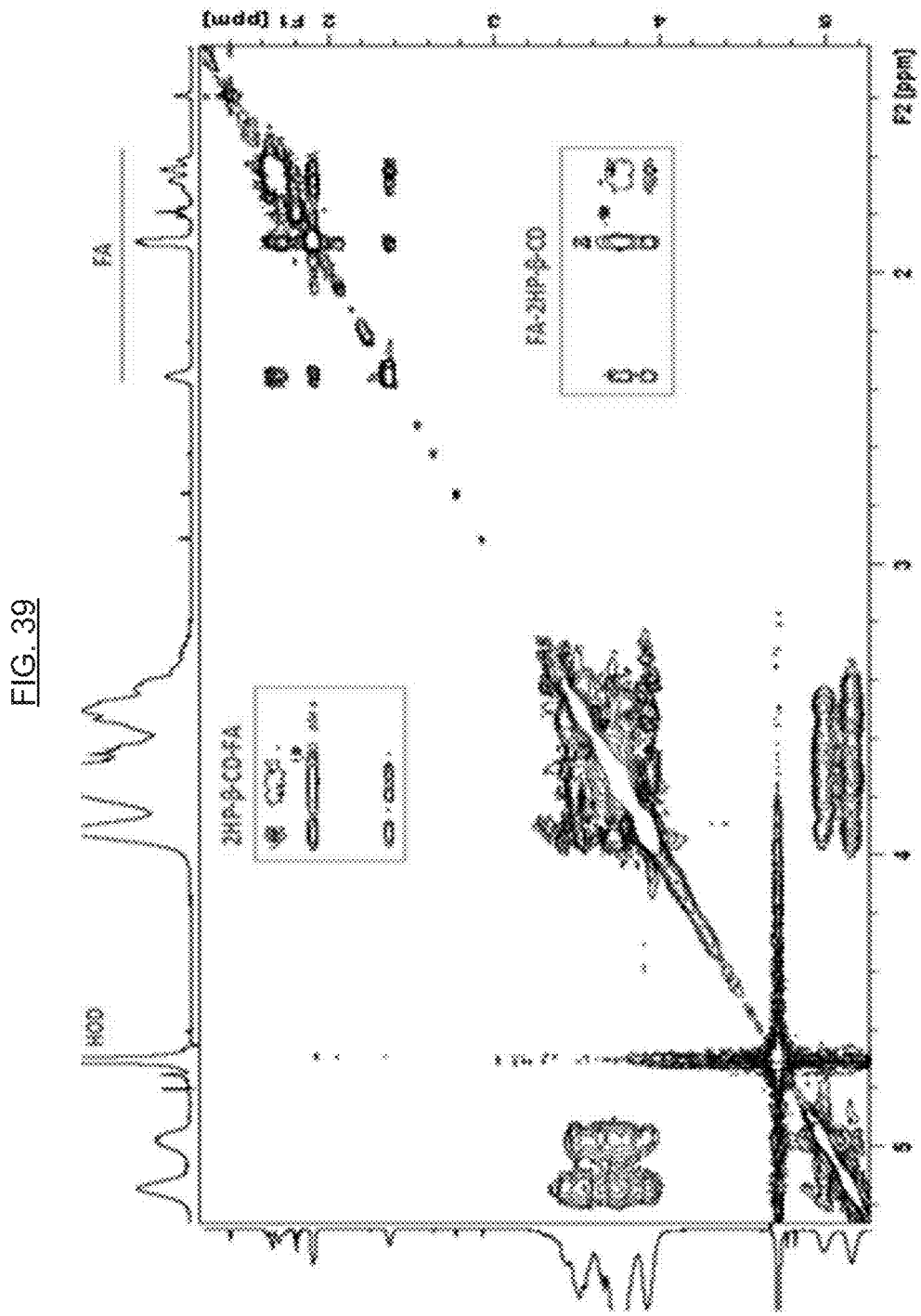
FIG. 39 is a ROESY spectrum of 1-FA-2HP-β-CD dissolved in $D_2O$.
Figure 40:
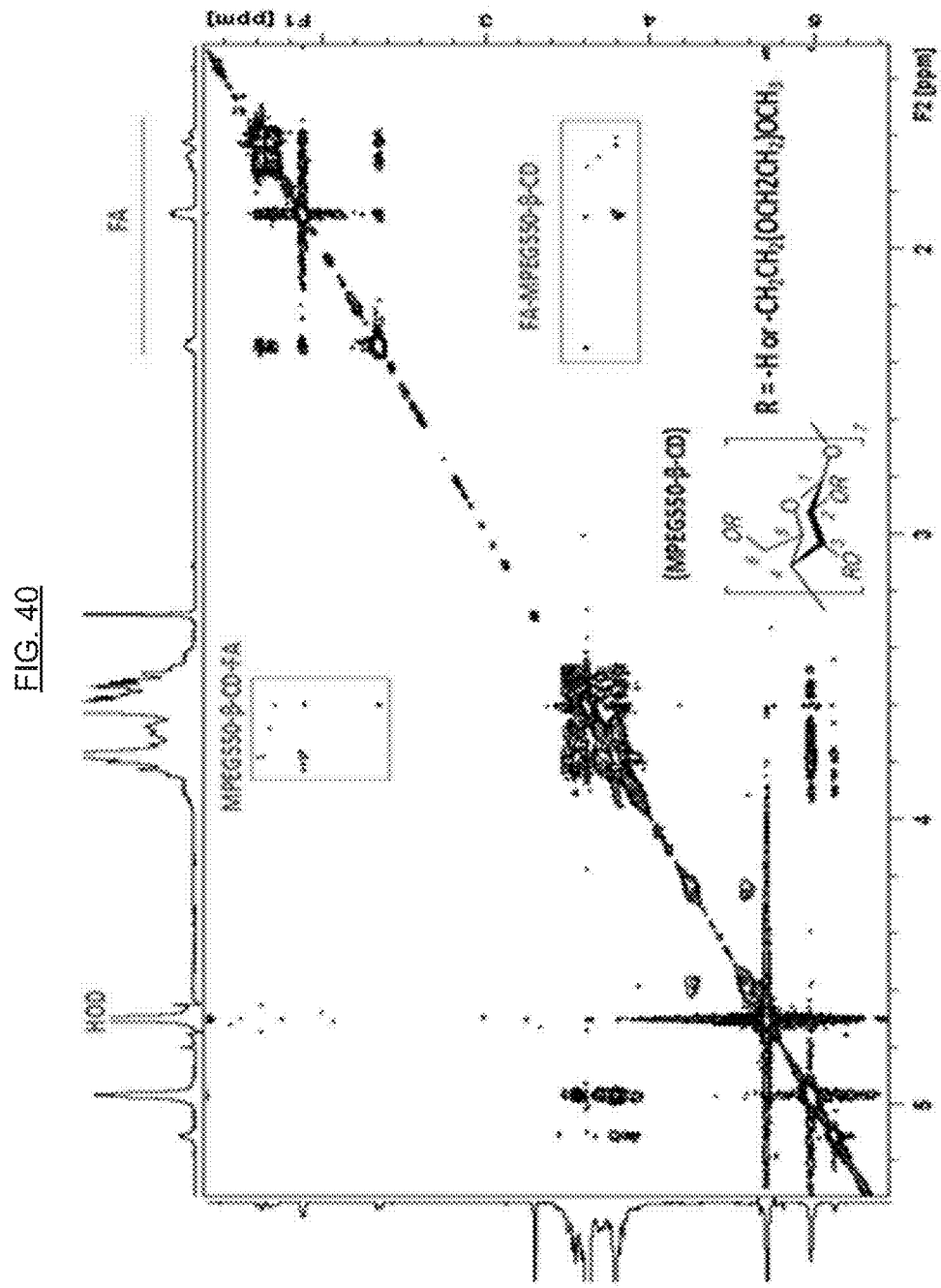
FIG. 40 is a ROESY spectrum of 1-FA-MPEG550-β-CD dissolved in $D_2O$.

The $^1H$ NMR spectra of 1-FA in $CDCl_3$, of 2HP-β-CD in $D_2O$ and of MPEG550-β-CD in $D_2O$ are shown in FIGS. 36, 37 and 38, respectively. The ROESY NMR spectra of the 1-FA-2HP-β-CDs and 1-FA-MPEG550-β-CDs are shown in FIG. 39 and FIG. 40, respectively. The correlations shown by the cross peaks were enclosed in the squares in the ROESY spectra of both of the ICs. The cross peaks indicate the formation of inclusion compounds. The results demonstrate that pegylated β-CDs preserve the inclusion property of the β-CD structure. Thus, pegylated CD products including pegylated β-CD produced by the methods disclosed herein can be used as a drug carrier.

Diffusion of MPEG-β-CDs in Mucus

An inclusion compound containing a MPEG-CD entity and a drug for delivery (e.g., to a patient in need thereof) will have decreased interaction with mucin, as compared to an inclusion compound containing a non-pegylated CD entity (e.g., β-CD) and a drug for delivery. The pegylated CD is believed to insulate the CD (e.g., β-CD) carrying the drug for delivery from direct contact with mucin. MPEG chains may be quite dynamic in water. Thus, they tend to dynamically surround the attached CD (e.g., β-CD) to prevent the CD from being exposed to mucin. MPEGs were found to decrease mucoadhesion, and thus improve pegylated CD entity penetration, through mucus. MPEGs are quite water soluble, which enables MPEGs to stay in the water phase, rather than stick with mucin in mucus.

Preparation of Mucinous and Inclusion Compound Solutions

Mucin from bovine submaxillary glands (BMS, CAS#: 84195-52-8, molecular weight ~400000) was purchased from Sigma Aldrich. A Rica phosphate buffer 0.43M (pH=7) was diluted to 0.043 M, and NaCl was added to obtain a buffer solution containing 36 mM NaCl. The mucinous solutions were made to have concentrations of 5.0, 10, 30, 50 and 100 mg BMS/mL in the Rica phosphate buffer. The concentrations of the inclusion complexes of 1-FA-2HP-β-CD, 1-FA-MPEG550-β-CD and 1-FA-MPEG2000-β-CD in the mucinous solutions were $6.0 \times 10^{-6}$. M. All of the inclusion compounds were made according to the method described above. The samples were freshly prepared and placed in 5 mL NMR tubes for running the diffusion experiments at 37° C. (human body temperature).

Diffusion NMR

Figure 41:
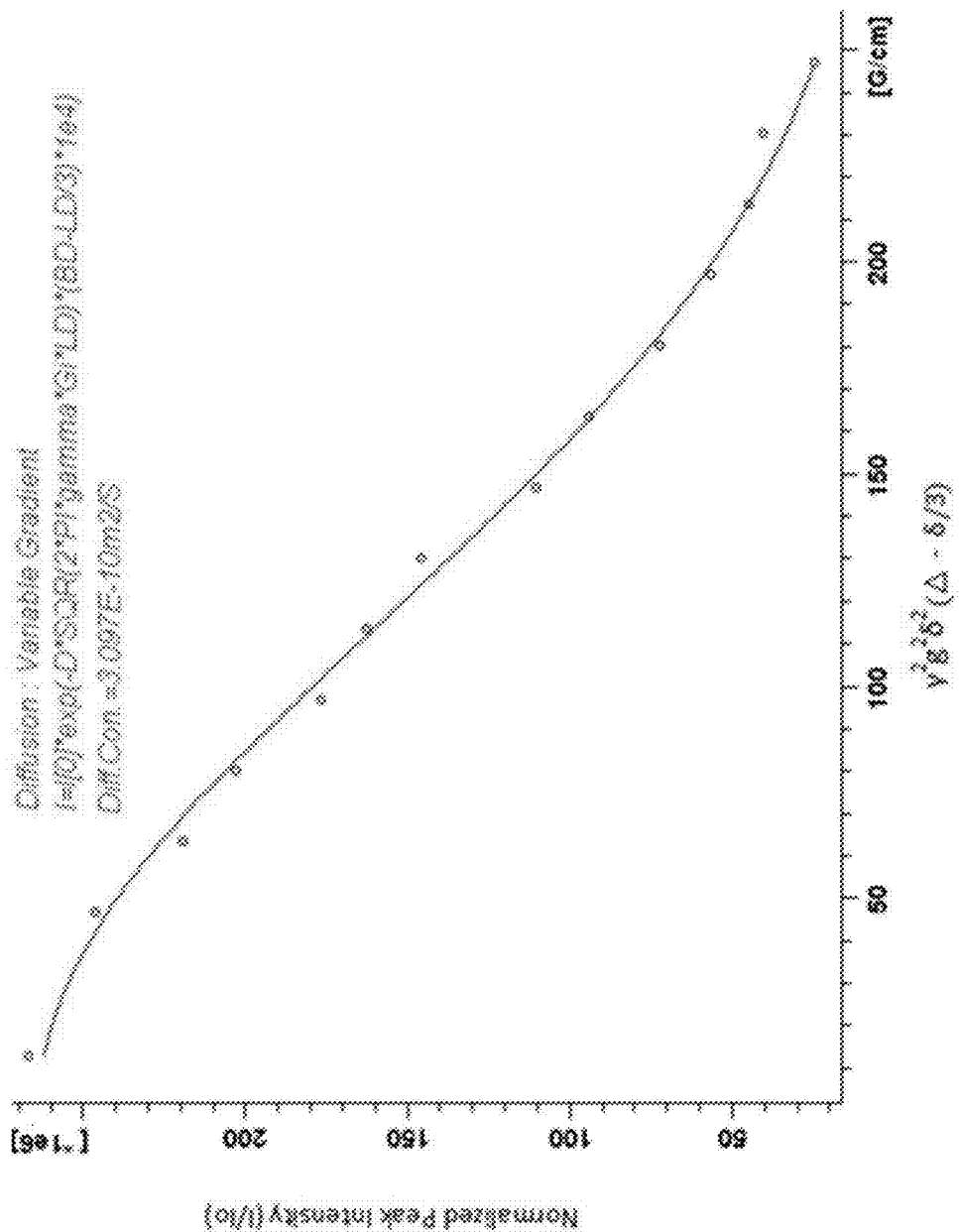
FIG. 41 is a typical $^{19}$F diffusion curve of FA-MPEG550-β-CD in 5.0 mg/ml mucinous solution.

The diffusion NMR experiments were based on the Pulsed Field Gradient Stimulated Echo (PFGSE) technique. The procedure results in a series of NMR spectra whose intensities decrease with the increased pulsed field gradient (PFG) according to Equation 1:

$$I = I_0 \text{Exp}(-D\gamma^2 g^2 \delta^2 (\Delta - \delta/3)) \quad (1)$$

where I and $I_0$ denote to the echo intensities with and without the PFG, D is the diffusion coefficient (also known as the diffusion constant), γ is the gyromagnetic ratio of the observed nuclei, δ is the length of the PFG, and Δ is the diffusion time. Typical $^{19}F$ experimental diffusion curves are shown in FIG. 41 for the inclusion compound of 1-FA-MPEG550-β-CD in 5.0 mg/ml mucinous buffer solution. The circles represent the experimental data and the solid line represents the theoretical fitting to Equation (1). The diffusion constant is $3.097 \times 10^{-10}$ $m^2/s$.

Results and Discussion

Figure 42:
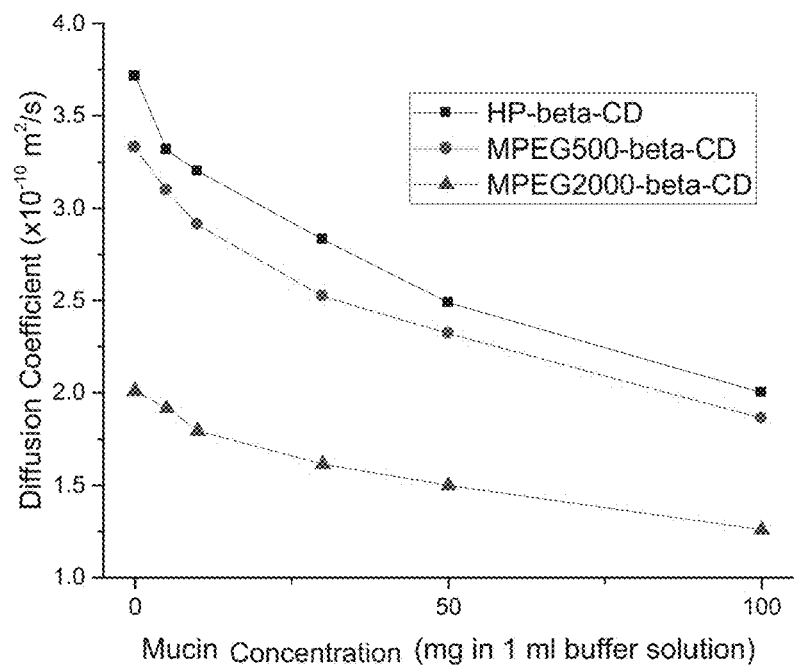
FIG. 42 is a graph of the diffusion coefficients of 1-FA-2HP-β-CD, 1-FA-MPEG550-β-CD and 1-FA-MPEG2000-β-CD versus mucin concentration.

Table 9 and FIG. 42 show the diffusion coefficients of the inclusion complexes of 1-FA-2HP-β-CDs, 1-FA-MPEG550-β-CD and 1-FA-MPEG2000-β-CD in the buffer solution and in the mucinous buffer solutions at different concentrations of mucin. Because the 1-FA molecules stayed in the cavities of β-CDs, the 1-FA molecules diffused together with the β-CDs (e.g., through the mucin). This is based on the fact that adamantane derivatives have β-CD association constants (Ka) on the order of $10^4$-$10^5$, and the validity of this method has been proven by the diffusions of 1-FA-β-CDs. The $^{19}$F diffusion coefficients reveal how the β-CDs diffuse in mucus. Table 9 shows that the diffusion coefficients decrease with an increase in the mucin concentration for all of the inclusion compounds, showing the increased hindrance of the mucin macromolecules when their concentrations are higher to the β-CDs. The diffusion constants decrease from 1-FA-2HP-β-CD to 1-FA-MPEG550-β-CD and to 1-FA-MPEG2000-β-CD at the same mucin concentration due to their increased molecular sizes, but not the interactions with mucin.

TABLE 9

Diffusion coefficients of inclusion complexes of 1-FA-2HPβ-CD, 1-FA-MPEG550-β-CD and 1-FA-MPEG2000-β-CD in the buffer solutions and the mucinous hydrogels at pH 7.0

| | Diffusion Coefficients ($\times 10^{-10}$ m$^2$/s) | | |
|---|---|---|---|
| FA-β-CD ICs | 2HP-β-CD | MPEG550-β-CD | MPEG2000-β-CD |
| 0 mg BMS/mL | 3.71 ± 0.01 | 3.33 ± 0.02 | 2.01 ± 0.01 |
| 5 mg BMS/mL | 3.32 ± 0.01 | 3.10 ± 0.02 | 1.92 ± 0.02 |
| 10 mg BMS/mL | 3.19 ± 0.01 | 2.91 ± 0.03 | 1.80 ± 0.01 |
| 30 mg BMS/mL | 2.83 ± 0.01 | 2.52 ± 0.02 | 1.62 ± 0.02 |
| 50 mg BMS/mL | 2.49 ± 0.02 | 2.32 ± 0.03 | 1.50 ± 0.03 |
| 100 mg BMS/mL | 2.00 ± 0.03 | 1.86 ± 0.03 | 1.26 ± 0.03 |

To see how the MPEG chains attached to the β-CD molecules alter the interactions of β-CD with mucin, normalized diffusion coefficients were calculated and used. These diffusion coefficients are defined as the ratio between the diffusion coefficient in mucus and the diffusion coefficient in water (buffer solution) (Dmucus/Dwater). Thus, the normalized diffusion coefficients take the size effect out of consideration.

Figure 43:
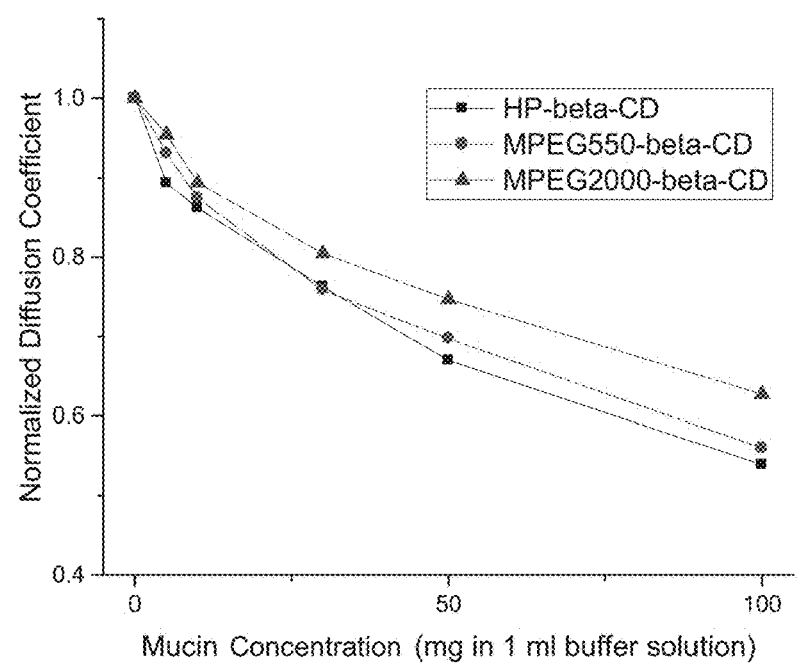
FIG. 43 is a graph of the normalized diffusion coefficients of 1-FA-2HP-β-CD, 1-FA-MPEG550-β-CD and 1-FA-MPEG2000-β-CD versus mucin concentrations.

The normalized diffusion coefficients are shown in Table 10 and plotted in FIG. 43. The results show that the normalized diffusion coefficients of 1-FA-2HP-β-CD are slightly smaller than those of 1-FA-MPEG550-β-CD at the same mucin concentrations. However, 1-FA-MPEG2000-β-CD shows significantly higher normalized diffusion coefficients at the same mucin concentrations. These results reveal that 2HP-β-CD has larger attractive interaction with mucin than pegylated β-CDs. In other words, MPEG chains can protect against adverse interactions of β-CD with mucin, which in turn indicates that drugs encapsulated in the pegylated β-CDs can be better protected in biological systems during their deliveries.

TABLE 10

Normalized diffusion coefficients ($D_{mucus}/D_{water}$) of the inclusion compounds 1-FA-2HPβ-CD, 1-FA-MPEG550-β-CD and 1-FA-MPEG2000-β-CD in mucinous hydrogels at pH 7.0

| | Normalized Diffusion Coefficients ($D_{mucus}/D_{water}$) | | |
|---|---|---|---|
| FA-β-CD ICs | 2HP-β-CD | MPEG550-β-CD | MPEG2000-β-CD |
| 0 mg BMS/mL | 1 | 1 | 1 |
| 5 mg BMS/mL | 0.893 | 0.931 | 0.954 |
| 10 mg BMS/mL | 0.862 | 0.875 | 0.894 |
| 30 mg BMS/mL | 0.763 | 0.758 | 0.805 |
| 50 mg BMS/mL | 0.670 | 0.697 | 0.747 |
| 100 mg BMS/mL | 0.539 | 0.560 | 0.627 |

Economic Potential/Commercial Applications for Pegylated CDs

β-CD and its derivatives have already found broad applications as drug carriers in the pharmaceutical industry. The use of cyclodextrins in pharmaceutical formulations are driven by the improved drug properties, such as aqueous solubility, drug stability and controlled drug release. About 30 different pharmaceutical products containing CDs have reached the worldwide market so far. Therefore, pegylated β-CDs with improved properties relative to β-CD and 2HP-β-CD are expected to have commercial applications in the pharmaceutical industry as well in other industrial sectors. For example, pegylated CDs may be useful for delivering a drug in the form of an inclusion compound comprising the drug and the pegylated cyclodextrin to a patient in need thereof through a mucus membrane by administering an effective amount of the drug in the inclusion compound to the patient through the membrane. An amount of the drug effective to treat or relieve a disease, illness, injury or trauma in or of the patient, or symptoms of such disease, illness, injury or trauma in the patient, may be administered to the patient.

CONCLUSION/SUMMARY

Thus, the present invention provides a compound comprising a cyclodextrin and a monoalkoxy polyethylene glycol linked thereto through an ether bond (a "pegylated cyclodextrin"), drug delivery vehicles and pharmaceutical formulations including the same, and methods for making the compound and the drug delivery vehicle and for delivering the drug to a patient in need thereof. The method of making includes the steps of creating either a tosylated monoalkoxy polyethylene glycol or a tosylated cyclodextrin, and either reacting the tosylated monoalkoxy polyethylene glycol with a deprotonated cyclodextrin, or reacting the tosylated cyclodextrin with a deprotonated monoalkoxy polyethylene glycol. The present pegylated cyclodextrin readily forms an inclusion compound with certain drugs to protect the drug against adverse interactions with mucin (e.g., in a mucus membrane).

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A compound comprising a beta-cyclodextrin and one or more monoalkoxy polyethylene glycols linked thereto through an ether bond, having the structure:

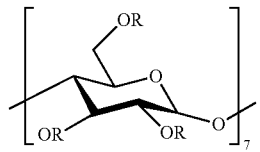

wherein one or two Rs in the compound is/are a monoalkoxy polyethylene glycol having the formula R'(OCH$_2$CH$_2$)$_n$—, R' is an alkyl group, the remaining Rs are H, and n is such that the group of the formula R'(OCH$_2$CH$_2$)$_n$— has a minimum molecular weight of 300 g/mol.

2. The compound of claim 1, wherein the monoalkoxy polyethylene glycol is a mono-C$_1$-C$_4$-alkoxy polyethylene glycol.

3. The compound of claim 2, wherein the mono-C$_1$-C$_4$-alkoxy polyethylene glycol is monomethoxy polyethylene glycol.

4. The compound of claim 1, wherein the monoalkoxy polyethylene glycol has a maximum molecular weight of 5000 g/mol.

5. The compound of claim 1, wherein the monomethoxy polyethylene glycol has a molecular weight of from 300 to 2000 g/mol.

6. A drug delivery vehicle comprising the compound of claim 1.

7. The compound of claim 1, wherein one R in the compound is the group of the formula R'(OCH$_2$CH$_2$)$_n$—.

8. A method of synthesizing a pegylated beta-cyclodextrin, the method comprising:
a) creating a tosylated monoalkoxy polyethylene glycol; and
b) reacting the tosylated monoalkoxy polyethylene glycol with a deprotonated beta-cyclodextrin to form the pegylated beta-cyclodextrin, the pegylated beta-cyclodextrin having the structure:

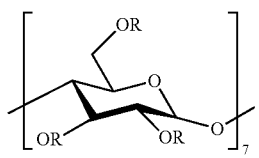

where each R is independently H or one of the one or more monoalkoxy polyethylene glycols, a plurality of the Rs are H, each of the one or more monoalkoxy polyethylene glycols has the formula R'(OCH$_2$CH$_2$)$_n$—, R' is an alkyl group, and n is such that the group of the formula R'(OCH$_2$CH$_2$)$_n$— has a minimum molecular weight of 200 g/mol.

9. The method of claim 8, wherein creating the tosylated monoalkoxy polyethylene glycol comprises:
a) reacting a monoalkoxy polyethylene glycol with a deprotonating agent to form a deprotonated intermediate, and
b) reacting the deprotonated intermediate with a toluenesulfonyl halide.

10. The method of claim 9, wherein the deprotonating agent comprises an alkali metal hydride.

11. The method of claim 10, wherein a molar ratio of the alkali metal hydride to the monoalkoxy polyethylene glycol is from 1:1 to 2:1.

12. The method of claim 8, wherein one or two Rs in the compound is/are the group of the formula R'(OCH$_2$CH$_2$)$_n$—, the remaining Rs are H, and the monoalkoxy polyethylene glycol has a molecular weight of 300 to 5000 g/mol.

13. A method of improving the water solubility of a beta-cyclodextrin, comprising:
a) linking a monoalkoxy polyethylene glycol to the beta-cyclodextrin through an ether bond to form a compound having the structure:

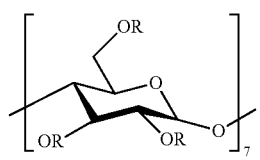

wherein one or of the one or more monoalkoxy polyethylene glycols, a plurality of the Rs are H, each of the one or two Rs in the compound is a monoalkoxy polyethylene glycol having the formula R'(OCH$_2$CH$_2$)$_n$—, R' is an alkyl group, the remaining Rs are H, and n is such that the group of the formula R'(OCH$_2$CH$_2$)$_n$— has a molecular weight of 300 to 5000 g/mol; and
b) dissolving the compound in water.

14. The method of claim 13, wherein said method improves the water solubility of the cyclodextrin by at least 30 times.

15. The method of claim 12, wherein one R in the compound is the group of the formula R'(OCH$_2$CH$_2$)$_n$—.

16. A method of synthesizing an inclusion compound containing a drug and a compound comprising a beta-cyclodextrin and one or more monoalkoxy polyethylene glycols linked thereto through an ether bond, having the structure:

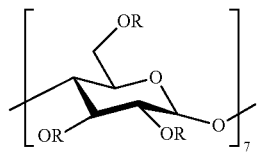

where each R is independently H or one of the one or more monoalkoxy polyethylene glycols, a plurality of the Rs are H, each of the one or more monoalkoxy polyethylene glycols has the formula R'(OCH$_2$CH$_2$)$_n$—, R' is an alkyl group, and n is such that the group of the formula R'(OCH$_2$CH$_2$)$_n$— has a minimum molecular weight of 200 g/mol, the method comprising:
a) dissolving the compound in deionized water or an aqueous buffer solution to form a solution; and
b) mixing the solution with the drug to form the inclusion compound.

17. The method of claim 16, further comprising dissolving the drug in an organic solvent that is miscible with water to form a separate solution prior to mixing the solution with the drug.

18. A method of delivering a drug to a patient in need thereof, comprising:
a) creating an inclusion compound comprising the drug and a compound comprising a beta-cyclodextrin and one or more monoalkoxy polyethylene glycols linked thereto through an ether bond, having the structure:

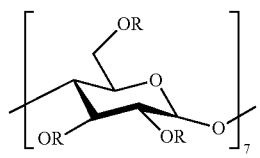

where each R is independently H or one of the one or more monoalkoxy polyethylene glycols, a plurality of the Rs are H, each of the one or more monoalkoxy polyethylene glycols has the formula $R'(OCH_2CH_2)_n-$, $R'$ is an alkyl group, and n is such that the group of the formula $R'(OCH_2CH_2)_n-$ has a minimum molecular weight of 200 g/mol; and b) administering an effective amount of the drug in the inclusion compound to the patient.

* * * * *